United States Patent
Fernandez Lima et al.

(10) Patent No.: US 10,386,372 B1
(45) Date of Patent: Aug. 20, 2019

(54) MATERIALS AND METHODS FOR SCREENING TOPOISOMERS

(71) Applicants: Francisco Fernandez Lima, Miami, FL (US); Kevin Jeanne Dit Fouque, Miami, FL (US)

(72) Inventors: Francisco Fernandez Lima, Miami, FL (US); Kevin Jeanne Dit Fouque, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 15/893,259

(22) Filed: Feb. 9, 2018

(51) Int. Cl.
*G01N 33/50* (2006.01)
*G01N 33/68* (2006.01)
*H01J 49/00* (2006.01)
*H01J 49/04* (2006.01)
*H01J 49/40* (2006.01)

(52) U.S. Cl.
CPC ...... *G01N 33/6848* (2013.01); *H01J 49/0031* (2013.01); *H01J 49/04* (2013.01); *G01N 2560/00* (2013.01); *H01J 49/40* (2013.01)

(58) Field of Classification Search
USPC ..................................................... 250/282
See application file for complete search history.

(56) References Cited

U.S. PATENT DOCUMENTS

| 7,838,821 | B2 * | 11/2010 | Clemmer | G01N 27/622 250/281 |
| 8,785,848 | B2 * | 7/2014 | Wu | G01N 27/622 250/281 |
| 9,797,866 | B2 * | 10/2017 | Carver | H01J 49/0031 |
| 10,001,456 | B2 * | 6/2018 | Campbell | G01N 27/624 |
| 2018/0246062 | A1 * | 8/2018 | Hofmann | G01N 33/6848 |

OTHER PUBLICATIONS

Hegemann, "Lasso Peptides: An Intriguing Class of Bacterial Natural Products", Acc. Chem. Res. 2015, 48, pp. 1909-1919.*
Adams, K. J. et al., "Isomer separation of polybrominated diphenyl ether metabolites using nanoESI-TIMS-MS." Int. J. Ion Mobil. Spec., 2016, 19: 69-76.
Badman, E. R. et al., "Monitoring Structural Changes of Proteins in an Ion Trap over ~10-200 ms: Unfolding Transitions in Cytochrome c Ions." Anal. Chem., 2001, 73: 6000-6007.
Baird, M. A., Shvartsburg, A. A., "Localization of Post-Translational Modifications in Peptide Mixtures via High-Resolution Differential Ion Mobility Separations Followed by Electron Transfer Dissociation." American Society for Mass Spectrometry, 2016, 27: 2064-2070.
Benigni, P. et al., "Analysis of Photoirradiated Water Accomodated Fractions of Crude Oils Using Tandem TIMS and FT-ICR MS." Environmental Science and Technology, 2017, 51: 5978-5988.
Benigni, P., Fernandez-Lima, F., "Oversampling Selective Accumulation Trapped Ion Mobility Spectrometry Couple to FT-ICR MS: Fundamentals and Applications." Analytical Chemistry, 2016, 88: 7404-7412.
Benigni, P. et al., "Targeted High-Resolution Ion Mobility Separation Coupled to Ultrahigh-Resolution Mass Spectrometry of Endocrine Disruptors in Complex Mixtures." Analytical Chemistry, 2015, 87: 4321-4325.
Benigni, P. et al., "Towards the analysis of high molecular weight proteins and protein complexes using TIMS-MS." Int. J. Ion Mobil. Spec., 2016, 19: 95-104.
Castellanos, S. et al., "Fast screening of polycyclic aromatic hydrocarbons using trapped ion mobility spectrometry-mass spectrometry." Anal. Methods, 2014, 6: 9328-9332.
Clowers, B. H., Hill, H. H. Jr., "Influence of cation adduction on the separation characteristics of flavonoid diglycoside isomers using dual gate-ion mobility—quadrupole ion trap mass spectrometry." J. Mass. Spectrom., 2006, 41: 339-351.
Dilger, J. M. et al., "A database of alkali metal-containing peptide cross sections: Influence of metals on size parameters for specific amino acids." International Journal of Mass Spectrometry, 2012, 330-332: 35-45.
Dit Fouque, K. J. et al., "Gas-phase conformations of capistruin—comparison of lasso, branched-cyclic and linear topologies." Rapid Commun. Mass Spectrom., 2015, 29: 1411-1419.
Dit Fouque, K. J., et al., "Ion Mobility-Mass Spectrometry of Lasso Peptides: Signature of a Rotaxane Topology." Analytical Chemistry, 2015, 87: 1166-1172.
Dit Fouque, K. J. et al., "Signatures of Mechanically Interlocked Topology of Lasso Peptides by Ion Mobility-Mass Spectrometry: Lessons from a Collection of Representatives." J. Am. Soc. Mass. Spectrom., Feb. 2017 28(2): 315-322.
Dodds, J. N. et al., "Correlating Resolving Power, Resolution, and Collision Cross Section: Unifying Cross-Platform Assessment of Separation Efficiency in Ion Mobility Spectrometry." Analytical Chemistry, 2017, 89: 12176-12184.
Domalain, V. et al., "Enantiomeric differentiation of aromatic amino acids using traveling wave ion mobility-mass spectrometry." Chem. Sci., 2014, 5: 3234-3239.
Domalain, V. et al., "Role of Cationization and Multimers Formation for Disastereomers Differentiation by Ion Mobility-Mass Spectrometry." J. Am. Soc. Mass Spectrom., 2013, 24: 1437-1445.
Fernandez-Lima, F. A. et al., "Gas-phase separation using a trapped ion mobility spectrometer." Int. J. ion Mobil. Spec., 2011, 14: 93-98.
Fernandez-Lima, F. A. et al., "Note:Integration of trapped ion mobility spectrometry with mass spectrometry." Review of Scientific Instruments, 2011, 82 (126106): 1-3.

(Continued)

*Primary Examiner* — Phillip A Johnston
(74) *Attorney, Agent, or Firm* — Saliwanchik, Lloyd & Eisenschenk

(57) ABSTRACT

The invention pertains to materials and methods for identifying and/or isolating isomers, particularly, of biomolecules, such as polypeptides and proteins. The methods of identifying and/or isolating isomers of a molecule according to the invention comprise subjecting a sample to ionization prior to IMS followed by MS. In some embodiments, the sample is subjected to metallization during the ionization step.

20 Claims, 51 Drawing Sheets
(42 of 51 Drawing Sheet(s) Filed in Color)
Specification includes a Sequence Listing.

(56) References Cited

OTHER PUBLICATIONS

Fernandez-Lima, F. A. et al., "On the Structure Elucidation Using Ion Mobility Spectrometry and Molecular Dynamics." J. Phys. Chem. A, 2009, 113: 8221-8234.

Flick, T. G. et al., "Structural Resolution of 4-Substituted Proline Diastereomers with Ion Mobility Spectrometry via Alkali Metal Ion Cationization." Analytical Chemistry, Feb. 2015, 87: 3300-3307.

Garabedian, A. et al., "Structures of the Kinetically Trapped i-motif DNA intermediates." Phys. Chem. Chem. Phys., 2016, 18: 26691-26702.

Garabedian, A. et al., "Towards Discovery and Targeted Peptide Biomarker Detection Using nano-ESI-TIMS-TOF MS." J. Am. Soc. Mass. Spectrom., 2017, 1-10.

Giles, K. et al., "Enhancements in travelling wave ion mobility resolution." Rapid Commun. Mass Spectrom., 2011, 25: 1559-1566.

Hegemann, J. D. et al., "Lasso Peptides: An Intriguing Class of Bacterial Natural Products." Accounts of Chemical Research, 2015, A-K.

Hernandez, D. R. et al., "Ion dynamics in a trapped ion mobility spectrometer." Analyst, 2014, 139: 1913-1921.

Ibrahim, Y. M. et al., "Ultrasensitive Identification of Localization Variants of Modified Peptides Using Ion Mobility Spectrometry." Analytical Chemistry, 2011, 83: 5617-5623.

Jia, C. et al., "Site-Specific Characterization of D-Amino Acid Containing Peptide Epimers by Ion Mobility Spectrometry." Analytical Chemistry, 2014, 86: 2972-2981.

Kaszycki, J. L., Shvartsburg, A. A., "A Priori Intrinsic PTM Size Parameters for Predicting the Ion Mobilities of Modified Peptides." J. American Society for Mass Spectrometry, 2017, 28: 294-302.

Lanucara, F. et al., "The power of ion mobility-mass spectrometry for structural characterization and the study of conformational dynamics." Nature Chemistry, Apr. 2014, 6: 281-294.

Lapthorn, C. et al., "Ion Mobility Spectrometry-Mass Spectrometry (IMS-MS) of Small Molecules: Separating and Assigning Structures to Ions." Mass Spectrometry Reviews, 2013, 32: 43-71.

Liu, F. C. et al., "On the structural denaturation of biological analytes in trapped ion mobility spectrometry-mass spectrometry." Analyst, 2016, 141: 3722-3730.

McKenzie-Coe, A. et al., "Lifetimes and stabilities of familiar explosive molecular adduct complexes during ion mobility measurements." Analyst, 2015, 140: 5692-5699.

Meier, F. et al., "Parallel Accumulation-Serial Fragmentation (PASEF): Multiplying Sequencing Speed and Sensitivity by Synchronized Scans in a Trapped Ion Mobility Device." Journal of Proteome Research, 2015, 14: 5378-5387.

Molano-Arevalo, J. C. et al., "Characterization of Intramolecular Interactions of Cytochrome c Using Hydrogen-Deuterium Exchange-Trapped Ion Mobility Spectrometry-Mass Spectrometry and Molecular Dynamics." Analytical Chemistry, 2017, 89: 8757-8765.

Molano-Arevalo, J. C. et al., "Flavin Adenine Dinucleotide Structural Motifs: From Solution to Gas Phase." Analytical Chemistry, 2014, 86: 10223-10230.

Paglia, G. et al., "Application of ion-mobility mass spectrometry for lipid analysis." Anal. Bioanal. Chem., 2015, 407: 4995-5007.

Pang, X. et al., "Structural Characterization of Monomers and Oligomers of D-Amino Acid-Containing Peptides Using T-Wave Ion Mobility Mass Spectrometry." J. Am. Soc. Mass Spectrom., 2017, 28: 110-118.

Pringle, S. D. et al., "An investigation of the mobility separation of some peptide and protein ions using a new hybrid quadrupole/travelling wave IMS/oa-ToF instrument." International Journal of Mass Spectrometry, 2007, 261: 1-12.

Pu, Y. et al., "Separation and Identification of Isomeric Glycans by Selected Accumulation-Trapped Ion Mobility Spectrometry-Electron Activated Dissociation Tandem Mass Spectrometry." Analytical Chemistry, 2016, 88: 3440-3443.

Rdgeway, M. E. et al., "Microheterogeneity within conformational states of ubiquitin revealed by high resolution trapped ion mobility spectrometry." Analyst, 2015, 140: 6964-6972.

Schenk, E. R. et al., "Direct Observation of Differences of Carotenoid Polyene Chain cis/trans Isomers Resulting from Structural Topology." Analytical Chemistry, 2014, 86: 2019-2024.

Schenk, E. R. et al., "Isomerization Kinetics of AT Hook Decapeptide Solution Structures." Analytical Chemistry, 2014, 86: 1210-1214.

Schenk, E. R. et al., "Kinetic Intermediates of Holo- and Apo-Myoglobin Studied Using HDX-TIMS-MS and Molecular Dynamic Simulations." J. Am. Soc. Mass. Spectrom., 2015, 26: 555-563.

Shliaha, P. V. et al., "Characterization of Complete Histone Tail Proteoforms Using Differential Ion Mobility Spectrometry." Analytical Chemistry, 2017, 89: 5461-5466.

Shvartsburg, A. A., Smith, R. D., "Fundamentals of Traveling Wave Ion Mobility Spectrometry." Anal. Chem., 2008, 80: 9689-9699.

Shvartsburg, A. A. et al., "High-Resolution Field Asymmetric Waveform Ion Mobility Spectrometry Using New Planar Geometry Analyzers." Anal. Chem., 2006, 78: 3706-3714.

Shvartsburg, A. A. et al., "Ion Mobility Separation of Variant Histone Tails Extending to the 'Middle-Down' Range." Analytical Chemistry, 2012, 84: 4271-4276.

Shvartsburg, A. A. et al., "Separation and Classification of Lipids Using Differential Ion Mobility Spectrometry." J. Am. Soc. Mass Spectrom., 2011, 22: 1146-1155.

Shvartsburg, A. A. et al., "Separation of a Set of Peptide Sequence Isomers Using Differential Ion Mobility Spectrometry." Analytical Chemistry, 2011, 83: 6918-6923.

Silveira, J. A. et al., "High Resolution Trapped Ion Mobility Spectrometery of Peptides." Analytical Chemistry, 2014, 36: 5624-5627.

Soyez, D. et al., "Experimental strategies for the analysis of D-amino acid containing peptides in crustaceans: A review." Journal of Chromatography B, 2011, 879: 3102-3107.

Tolmachev, A. V. et al., "Characterization of Ion Dynamics in Structures for Lossless Ion Manipulations." Analytical Chemistry, 2014, 86: 9162-9168.

Yang, H. et al., "Identification of structurally closely related monosaccharide and disaccharide isomers by PMP labeling in conjunction with IM-MS/MS." Scientific Reports, 2016, 6 (28079): 1-9.

Zheng, X. et al., "Distinguishing D- and L-aspartic and isoaspartic acids in amyloid β peptides with ultrahigh resolution ion mobility spectrometry." Chem. Commun., 2017, 53: 7913-7916.

Zhong, Y. et al., "Ion mobility-mass spectrometry for structural proteomics." Expert Rev. Proteomics, 2012, 9 (1): 47-58.

* cited by examiner

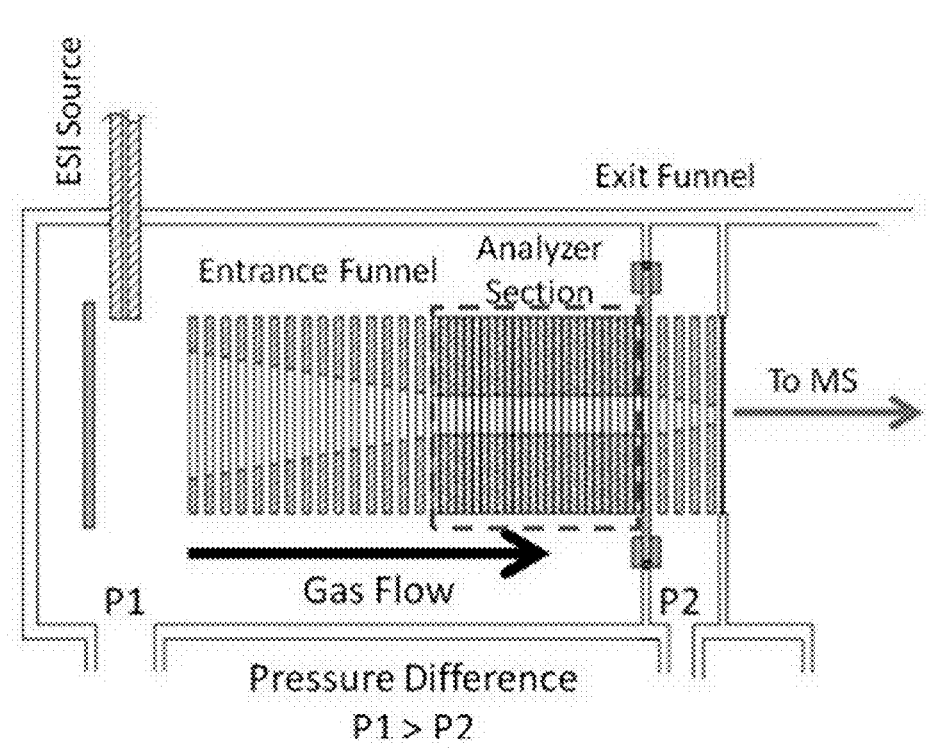
FIG. 3
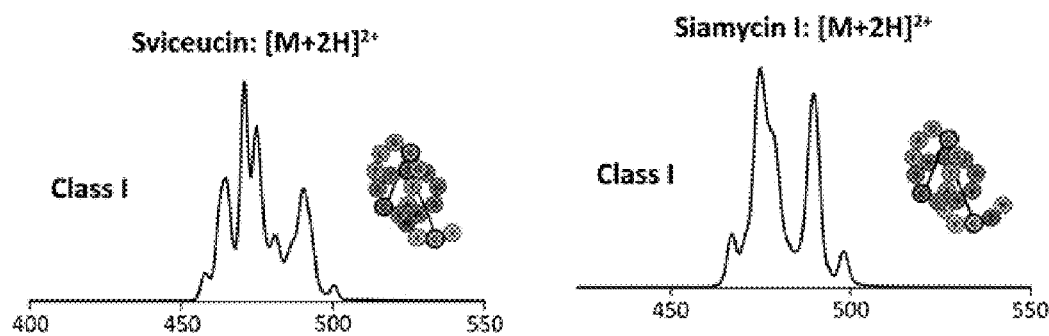
FIG. 4A
FIG. 4B

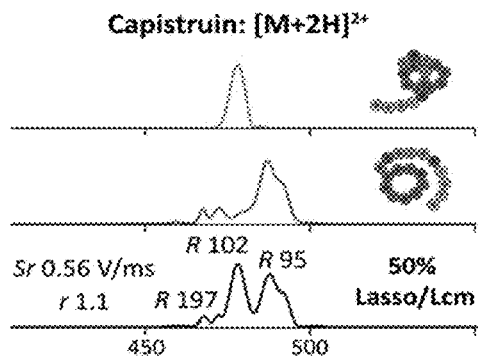
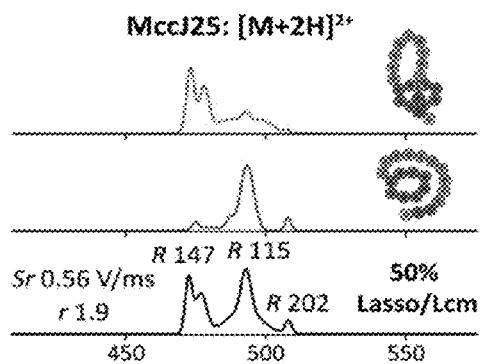
FIG. 8A                FIG. 8B
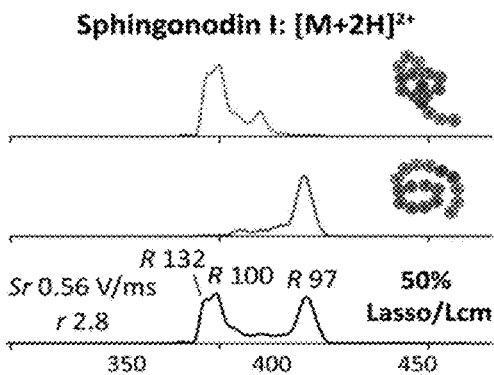
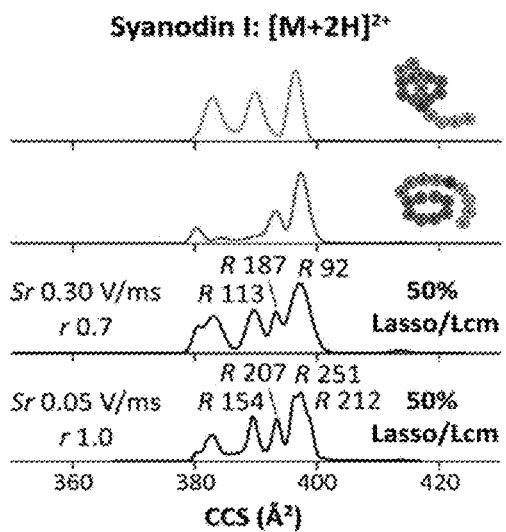
FIG. 8C                FIG. 8D

MATERIALS AND METHODS FOR SCREENING TOPOISOMERS

GOVERNMENT SUPPORT

This invention was made with government support under GM106414 awarded by the National Institutes of Health and CHE1654274 awarded by the National Science Foundation. The government has certain rights in the invention.

The Sequence Listing for this application is labeled "SEQList-Feb9-ST25.txt", which was created on Feb. 9, 2018, and is 8 KB. The entire content is incorporated herein by reference in its entirety.

BACKGROUND

Natural products play important roles in drug development. Ribosomally synthesized and post-translationally modified peptides (RiPPs) present a broad structural diversity, typically restricting conformational flexibility to allow better target recognition and to increase chemical, physical and proteolytic stability augmenting chemical functionality. For example, lasso peptides are a structural class of RiPPs exhibiting enzyme inhibitory, receptor antagonistic, antimicrobial or antiviral properties. Lasso peptides have unique mechanically interlocked topology in which the C-terminal tail is threaded through and trapped within an N-terminal macrolactam ring generated by an isopeptidic bond between the amino group of a glycine, alanine, serine or cysteine residue at position 1 and the side-chain carboxyl group of a glutamate or aspartate residue at position 7, 8 or 9 (FIG. 1). This threaded fold is maintained in the C-terminal tail region by steric hindrance, mediated by bulky side-chains above and below the ring, named plugs, and/or by disulfide bonds leading to a compact rotaxane type structure. As a consequence of their compact and interlocked structures, lasso peptides often display strong resistance against chemical and proteolytic degradation as well as, in many cases, thermally-induced unthreading.

More than 40 lasso peptides are now found in actinobacteria, proteobacteria, and firmicutes. Their size ranges from 13 to 24 residues, and are divided into three classes depending on the absence (class II) or presence of one (class III) or two (class I) disulfide bonds that can further stabilize the lasso structure (FIG. 1). Many lasso peptides were discovered through genome mining approach. The extraordinary mechanically interlocked topology of lasso peptides, together with their panel of biological activities makes them a promising scaffold for next generation drug design. These structures have not been reproduced using synthetic methods. However, unthreading of the C-terminal tail has been reported for several lasso peptides, yielding their corresponding (mostly) biologically inactive branched-cyclic topoisomers. The discovery and search for new lasso peptides as potential drug candidates requires high throughput analytical tools capable of differentiating them from their unthreaded branched-cyclic topoisomers.

Metal ions play a vital role in many biological processes. They act in a variety of important functions in protein systems including enzyme catalysis, protein folding, assembly, structural stability and conformational change. The presence or absence of a specific metal ion is crucial to the conformational space and/or chemical functionality of over one third of all proteins. Several structural studies aimed to determine the binding site locations, the nature of metal ion coordination, and the role of metal-ligand interactions on structure and function. Interactions between metal ions and biomolecules have been investigated using well established techniques such as circular dichroism, nuclear magnetic resonance (NMR) spectroscopy, and x-ray crystallography. Furthermore, the structures of metal-containing peptides and proteins in the gas-phase have been reported using mass spectrometry equipped with soft ionization sources such as electrospray ionization (ESI). Interestingly, the addition of metal ions often influences the fragmentation patterns upon activation. In addition, the potential of metal ions to differentiate isomer species, which present the same fragmentation pattern, has been shown using tandem mass spectrometry. All these results suggest the existence of highly-specific metal-binding sites. The interaction of peptides and proteins with metal ions has been a subject of considerable interest in ion mobility spectrometry coupled to mass spectrometry (IMS-MS) since the pioneering work of Clemmer and Jarrold. These studies showed the potential of IMS-MS to provide a more detailed understanding of the basic interactions that occur and represent an important step in the conformational engineering of peptides and proteins. Research on metal-peptide systems provides a basis for understanding metal interactions occurring in biochemically relevant systems.

Nearly all biomolecules have one or more chiral centers (typically on the C atoms) with geometries often crucial to their function. In enantiomeric pairs, all symmetry centers are inverted to form the mirror images. In particular, all $\alpha$-amino acids (aa) except glycine have four different groups attached to the $\alpha$-carbon, which allows left-handed (L) and right-handed (D) forms. From these, one can assemble peptides of any length comprising just L- or D-enantiomers and both forms (diastereomers or epimers). A species can have only one enantiomer, but numerous diastereomers with single or multiple D/L-substitutions in different positions.

No natural D-aa containing peptides (DAACPs) or proteins were known (except in bacterial walls) until the discovery of dermorphin in frog skin. About forty DAACPs are now found in eukaryotes such as arthropod, molluscan, and vertebrate. These peptides range from four to over fifty residues, and are epimers of all-L peptides with D-aa often located in the $2^{nd}$ position from the N-terminus.

Such species have different conformations, resulting in distinct interactions with both chiral and non-chiral partners. Hence, DAACPs bind to receptors with different selectivity and affinity than the L-analogs, dramatically altering the biological function. For example, NdWFa enhances the heartbeat of sea slugs at $10^{-10}$ M whereas the L-analog NWFa is inactive even at $10^{-6}$ M. Many DAACPs were discovered by comparing the biological activities of natural and synthetic L-analog peptides. The unnatural stereochemistry of D-residues commonly renders DAACPs resistant to proteolytic degradation, making them a promising scaffold for next-generation drug design. Fundamentally, understanding the prevalence, substitution patterns, synthesis pathways, properties, and biomedical roles of DAACPs may help grasping the origin of extraordinary preference for L-aa across biology that is likely central to the genesis of life on Earth.

The number, abundance, and biomedical importance of DAACPs may be profoundly underestimated because of the paucity of analytical techniques for their detection and characterization. Unlike most post-translational modifications (PTMs), D/L-substitutions cause no mass shift for peptides or their fragments. Therefore, the standard mass spectrometry (MS) approach to PTM analysis (finding the precursors with mass shifts and tracking those for dissociation products to locate the PTM site) would not work for DAACP detection.

As the tools for identification and quantification of mature proteins, proteomics is focused on the characterization of proteoforms and revealing the activity-modulating impacts of distinct patterns of post-translational modifications (PTMs). Many proteoforms feature different number or type of PTMs, detectable by MS based on the mass increment. Others are isomers with identical PTMs on different amino acid residues. Such "localization variants" are individually distinguishable by unique fragments in tandem MS, particularly employing electron transfer dissociation (ETD) that severs the protein backbone while retaining weaker PTM links. The conundrum is that multiple variants frequently coexist in cells, but MS/MS cannot disentangle mixtures of more than two as those with PTMs on internal sites yield no unique fragments. This calls for separation of protein (and peptide) variants at least to binary mixtures before the MS/MS step. Dedicated liquid chromatography (LC) methods could resolve some variants for peptides in the "bottom-up" mass range (<2.5 kDa) usual for tryptic digests, but not larger "middle-down" peptides (2.5-10 kDa) or intact proteins. Splitting proteins into peptides using sequence-specific proteases precludes global PTM mapping by obliterating the proteoform-specific connectivity information between the modified peptides.

This problem is most prominent for histone proteins that combine exceptional importance to life with great diversity of PTM types and sites. Histones (H2A, H2B, H3, and H4) consisting of ~100-140 residues are nucleosome core particles—the spools that store the DNA in cell nuclei and apparently regulate chromatin structure and function through dynamic reversible PTMs including methylation (me), dimethylation (me2), trimethylation (me3), acetylation (ac), phosphorylation (p), and others. Permuting their order and modulating the site occupation levels in this "histone code" may drastically alter the activity of whole genome, defined chromatin domains, genomic regions, and/or individual genes. Nearly all PTMs in histones are on the enzymatically cleavable N-terminal domains ("tails") protruding from the nucleosome. The H3 tail of ~50 residues (~5.5 kDa) is cleavable by the endoproteinase Glu-C, and its characterization approaches that of intact histone.

Given the presence of natural isomers, such as, topoisomers, epimers, and proteoforms of biomolecules and their importance in biological processes, methods of identifying and purifying such isomers are desired.

BRIEF SUMMARY

The invention provides materials and methods for identifying and/or isolating isomers, particularly, of biomolecules, such as small peptides and proteins. The methods of identifying and/or isolating isomers of a molecule according to the invention comprise subjecting a sample to ionization prior to IMS followed by MS. In some embodiments, the sample is subjected to metallization during the ionization step.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 3 shows schematics of a trapped ion mobility spectrometry (TIMS) cell.

FIGS. 4A-4M show typical high resolution TIMS spectra of lasso peptides using native nESI-TIMS-MS for the doubly protonated species. Schemes highlight the macrolactam rings in green, the loops in blue, the plugs in red and the C-terminal tails in orange. The disulfide bonds are represented by black lines. The proposed plugs are colored in purple.

FIGS. 8A-8D show typical high resolution IMS spectra for $[M+2H]^{2+}$ ions of (A) capistruin, (B) MccJ25, (C) sphingonodin I and (D) syanodin I (blue traces) with their branched-cyclic topoisomers (red traces) using nESI-TIMS-MS. The R, r, and scan rate values are given.

DETAILED DESCRIPTION

Traditional condensed-phase separations are nowadays increasingly complemented or replaced by faster, gas-phase separations (e.g., ion mobility spectrometry-mass spectrometry, IMS-MS). IMS-MS is used in a variety of bioanalytical applications (e.g., small molecules, lipidomics, proteomics, and structural biology) because of its high speed, higher selectivity and increase peak capacity.

Figure 1:
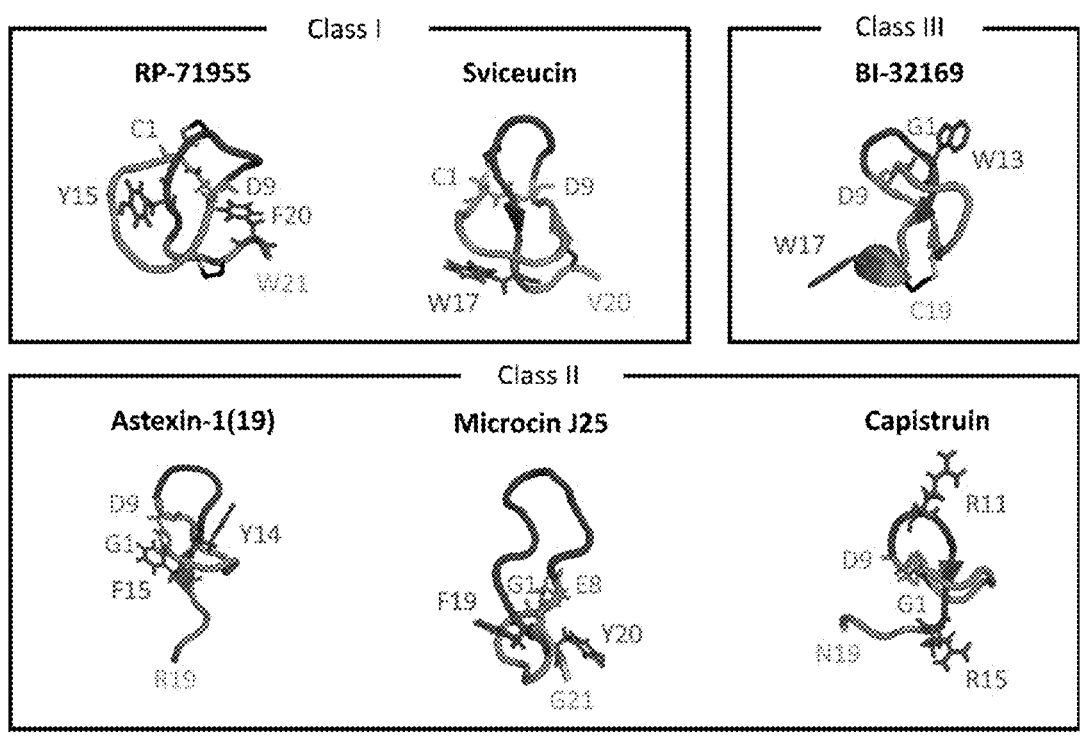
FIG. 1 shows general classification criteria for lasso peptides. The lasso topology of RP-71955, sviceucin (class I, two disulfide bonds), astexin-1(19), MccJ25, capistruin (class II, no disulfide bond) and BI-32169 (class III, one disulfide bond) are shown. Tridimensional structures display the macrolactam rings in green, the loops in blue, the plugs in red and the C-terminal tails in orange. The disulfide bonds are shown by black lines.
Figure 2:
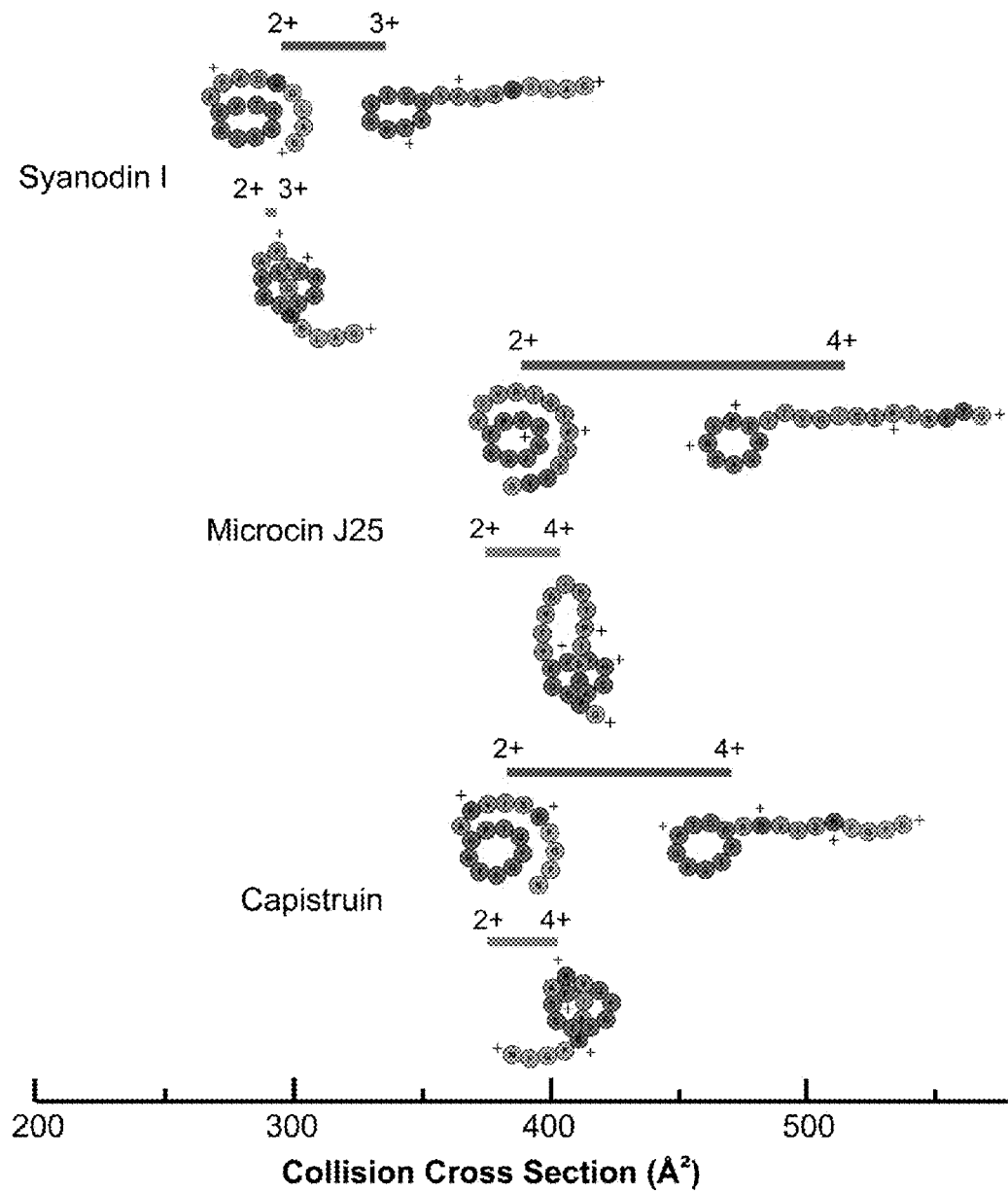
FIG. 2 shows CCS range observed for the multiply protonated species of capistruin, MccJ25 and syanodin I (blue traces) and their corresponding branched-cyclic (red traces) topoisomers using travelling wave ion mobility (TWIMS).
Figure 4C:
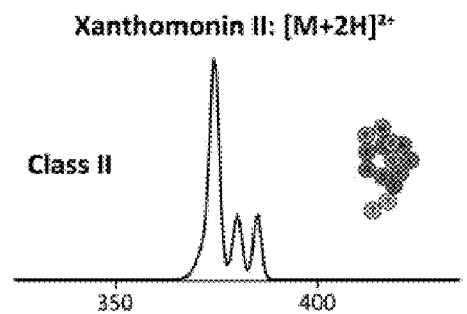
Figure 4D:
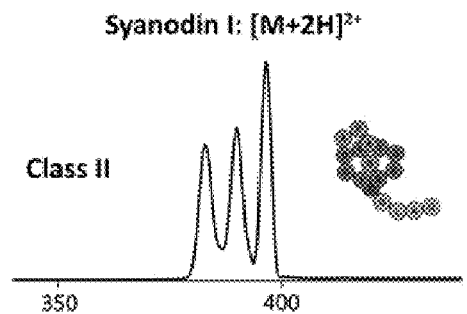
Figure 4E:
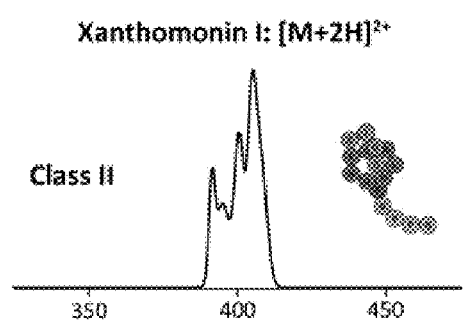
Figure 4F:
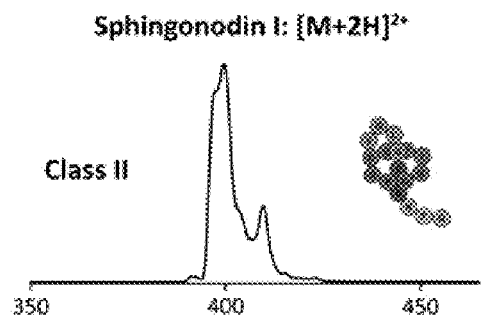
Figure 4G:
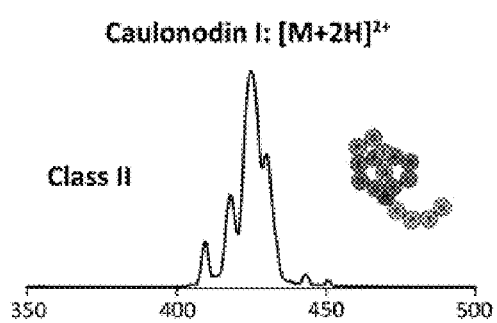
Figure 4H:
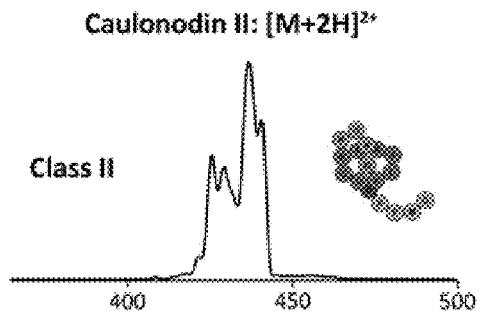
Figure 4I:
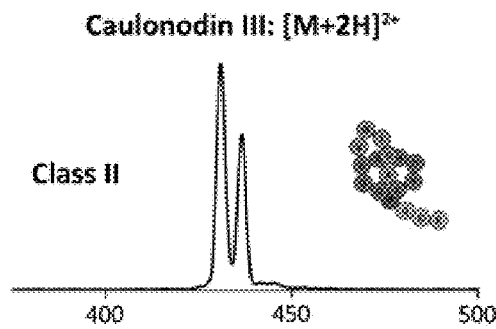
Figure 4J:
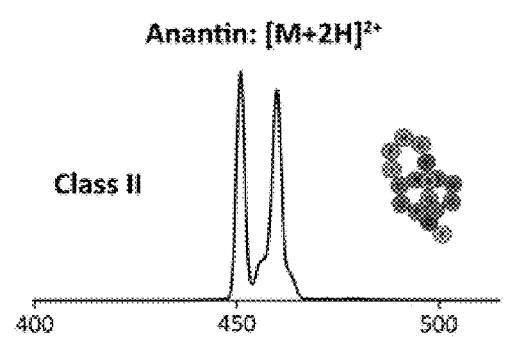
Figure 4K:
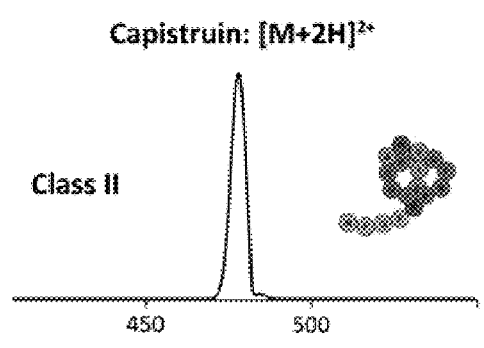
Figure 4L:
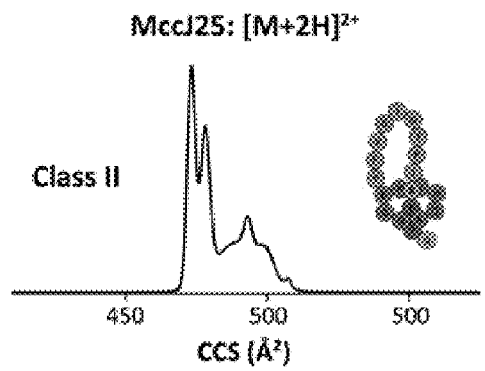
Figure 4M:
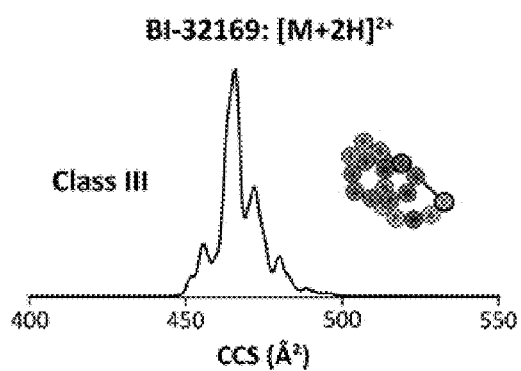

Few recent studies report the use of traveling wave IMS (TWIMS) for the characterization of lasso peptides. The modest resolving power of TWIMS with dynamic field (R~30-50 on the Ω scale), implemented in the Synapt G2 instrument (Waters), has permitted only partial (if any) separation between lasso and branched-cyclic topoisomers. Attempts to increase the TWIMS resolution has been reported using oligomers, shift reagents, metalation, or increasing the charge states in view of slower diffusion at equal mobility. For example, the use of sulfolane as a supercharging reagent permitted the differentiation of lasso and branched-cyclic topoisomers at high charge states not observed for lower charged species (FIG. 2).

Various forms of IMS devices can be typically classified as scanning (e.g., FAIMS, DMA, and transverse modulation IMS) or dispersive (e.g., drift-tube IMS, periodic focusing drift tube IMS, TWIMS, overtone mobility IMS, cyclic TWIMS, and SLIMS). In particular, the recent introduction of trapped IMS (TIMS) and its integration with MS analyzers, has found multiple applications in analytical workflows with high mobility resolving power (R up to ~400) in a compact geometry. TIMS-MS devices have proven useful for rapid separation and structural elucidation of biomolecules, for screening and targeted analysis of complex mixtures, tracking the isomerization kinetics, characterizing the conformational spaces of peptides, separation of D-amino acid containing peptides, DNA, proteins, and macromolecular complexes in native and denatured states.

While DAACPs and L-analogs yield the same fragments in collision-induced dissociation (CID), electron capture/transfer dissociation (EC/TD), and radical-directed dissociation (RDD), the ratios of the peak intensities ($r_{i,j} = a_i/a_j$ for species i and j) generally differ. Hence, one can distinguish DAACPs and quantify them in binary epimer mixtures using standards. The quantification accuracy and fractional limits of detection ($f_{LOD}$) and quantification ($f_{LOQ}$) depend on the chiral recognition factor $R_{CH}$ (relative difference between $r_{i,j}$ involved). In ergodic CID, ions are first heated to transition states that typically reduce or obliterate the structural distinctions between isomers. Direct mechanisms like EC/TD and RDD "instantly" fragment ions from initial geometries and thus are more sensitive to subtle structural differences. Indeed, typical $R_{CH}$ increase from 1-18 (mean of 5) in CID to 5-30 (mean of 21) in RDD, reducing $f_{LOD}$ from ~5-10% to ~1-2%. Still, $R_{CH}$ and thus $f_{LOD}$ and $f_{LOQ}$ vary across D/L-peptide pairs widely and unpredictably, and $f_{LOQ}$ much under 1% is needed to truly explore the DAACP complement in global proteomes. Exceptional specific activity of DAACPs necessitates isomer quantification with dynamic range of $>10^4$ ($f_{LOQ}<0.01\%$), which is not achieved by existing MS/MS techniques. The MS/MS methods also cannot disentangle mixtures of more than two epimers or pinpoint the D-aa position(s).

Certain embodiments of the invention provide methods for the identification and isolation of isomers, particularly, of biomolecules such as small peptides and proteins. For example, the methods of the invention can be used to separate and isolate topoisomers of peptides, such as lasso peptides from the corresponding branched cyclic peptide isomers based on differences in the mobility space under native physiological conditions. Certain methods of the invention can also be used to separate and isolate epimers of peptides containing D amino acids based on differences in the mobility space. Further methods of the invention can be used to separate and isolate proteins post-translationally modified at different locations.

The high mobility resolving power of TIMS allows separation of lasso peptides and their branched-cyclic topoisomers with the average R value of about 150, and the least R value of about 85. In specific embodiments, alkali metalation reagents, such as alkali (Na, K and Cs), alkaline earth (Mg and Ca) and transition (Co, Ni and Zn) salts, are used to metalize the topoisomers. The charge state and cationization with such metalation provide additional separation dimensions.

A set of thirteen lasso peptides, including ten class II, two class I and one class III representatives (Table 1) are differentiated using native nESI-TIMS MS. A branched-cyclic analog was available for four class II lasso peptides (underlined in Table 1). Using IMS, for example, TIMS, in combination with MS for high throughput screening of peptide topoisomers at physiological conditions is demonstrated.

TABLE 1

Summary of lasso peptides sorted by class and mass. The macrolactam rings are highlighted in bold, the loops are bolded and italicized, the plugs are underlined, and the C-terminal tails are underlined and italicized. The C-terminal parts of lasso peptides, for which the 3D structures have not been determined, are double underlined. Lasso peptides for which a corresponding branched-cyclic peptide was obtained are underlined in the peptide column.

| Peptide | Sequence | SEQ ID NO: | Molecular weight (Da) | Class |
|---|---|---|---|---|
| Sviceucin | CVWGGDCTD*FLGCGTA*<u>W</u>_ICV_ | 6 | 2084.41 | Class I |
| Siamycin I | CLGVGSCND*FAGCGYA*<u>I</u>_VCFW_ | 7 | 2163.51 | Class I |
| Xanthomonin II | GGPLAGE*EMGG*<u>ITT</u> | 8 | 1271.40 | Class II |
| <u>Syanodin I</u> | GISGGTVD<u>APAGQ</u>GLAG | 9 | 1409.50 | Class II |
| Xanthomonin I | GGPLAGE*EIGG*<u>FNVPG</u> | 10 | 1452.57 | Class II |

TABLE 1-continued

Summary of lasso peptides sorted by class and mass. The macrolactam rings are highlighted in bold, the loops are bolded and italicized, the plugs are underlined, and the C-terminal tails are underlined and italicized. The C-terminal parts of lasso peptides, for which the 3D structures have not been determined, are double underlined. Lasso peptides for which a corresponding branched-cyclic peptide was obtained are underlined in the peptide column.

| Peptide | Sequence | SEQ ID NO: | Molecular weight (Da) | Class |
|---|---|---|---|---|
| Sphingonodin I | GPGGITGDVGLGENNFG | 11 | 1542.61 | Class II |
| Caulonodin I | GDVLNAPEPGIGREPTG | 12 | 1660.78 | Class II |
| Caulonodin II | GDVLFAPEPGVGRPPMG | 13 | 1677.92 | Class II |
| Caulonodin III | GQIYDHPEVGIGAYGCE | 14 | 1789.92 | Class II |
| Anantin | GFIGWGNDIFGHYSGDF | 15 | 1870.97 | Class II |
| Capistruin | GTPGFQTPD4R*VIS*R*FGFN* | 16 | 2049.25 | Class II |
| MccJ25 | GGAGHVPEYF*VGIGTPIS*FYG | 17 | 2107.32 | Class II |
| BI-32169 | GLPWGCPSDI*PG*W*NTPW*AC | 18 | 2037.29 | Class III |

In certain embodiments, the use of nESI-TIMS-MS for high throughput screening of peptide topoisomers is provided for analyzing topoisomers of biomolecules, such as lasso peptides and their branched-cyclic analogs. The high resolving power (R~90-250) of the TIMS analyzer provides a "fingerprint" of the conformational space (e.g., multiple IMS bands) and baseline separation of the topoisomers. The analysis of three exemplary topoisomer mixtures at physiological conditions according to the instant methods shows that CCS differences of 0.8-3% are sufficient for effective separation of topoisomers. For all the tested lasso peptides, the branched-cyclic peptides had higher CCS, confirming that the C-terminal part of branched-cyclic peptides are more unfolded than for lasso peptides trapped into the macrolactam ring. The C-terminal chain length and amino acid composition also affects the IMS profiles of the lasso peptides.

The added analytical advantages of metalation to the nESI-TIMS-MS workflow were illustrated for the case of syanodin I topoisomers, where the difference in the IMS profiles can be enlarged by using alkali metal adducts (e.g., Na, K and Cs). Different IMS profiles for the topoisomers are obtained as a function of the metal ions for the same charge state, suggesting that the size of the metal ion plays an important role on the conformational space and type of intramolecular interactions that stabilize the conformational motifs.

Further investigation using alkali (Na, K and Cs), alkaline earth (Mg and Ca) and transition (Co, Ni and Zn) metal ions showed that the most abundant conformation of the doubly charged species generally increase in CCS upon metal ion adduction. A correlation between the lengths of the loop and the C-terminal tail with the conformational space of lasso peptides becomes apparent upon addition of metal ions. It was shown that the steric stabilization of the C-terminal region inside of the macrolactam ring in lasso peptides allows only for distinct interactions of the metal ion with either residues in the loop or tail region. This limits the size of the interacting region and apparently leads to a bias of metal ion binding in either the loop or tail region, depending whichever section is larger in the respective lasso peptide. For branched-cyclic peptides, the non-restricted C-terminal tail allows metal coordination by residues throughout this region, which can result in gas-phase structures that are sometimes even more compact than the lasso peptides. The added analytical advantages of metalation using the doubly cesiated species to the nESI-TIMS-MS workflow were illustrated with the formation of a preferential conformer, which results in a better analytical separation and discrimination between lasso and branched-cyclic topologies.

IMS, which is based on the ion transport in gases driven by electric field, provide key benefits of speed and distinct (often superior) selectivity. Linear IMS measures the absolute ion mobility (K) at low field strength (E), whereas differential or field asymmetric waveform IMS (FAIMS) relies on the difference between K at high and low E elicited by an asymmetric waveform. That $\Delta K$ is less correlated to the ion mass (m) than K itself, rendering FAIMS more orthogonal to MS than linear IMS by about 4-fold for many biomolecular classes comprising peptides. Therefore, FAIMS commonly separates isomers better than linear IMS of same resolving power (R), including peptides with sequence inversions and localization variants with diverse PTMs. In particular, complete histone tails and their segments involving various PTMs and sites were uniformly resolved.

Linear IMS separations of such variants were limited to a few phosphopeptides under ~1.5 kDa. Expanding this capability to the middle-down range and smaller PTMs would be of interest as linear IMS platforms can be more sensitive than high-definition FAIMS. They also determine the collision cross section ($\Omega$) unavailable from FAIMS, which may help understanding and predicting the PTM-controlled differences in stability of peptide folds with implications for activity in vivo. In certain aspects, the invention uses linear IMS, such as commercial traveling wave (TWIMS) and trapped (TIMS) platforms in the separation of PTM localization variants for complete histone tails. The H3 tail variants investigated by FAIMS was used to directly compare performance and evaluate the orthogonality between two dimensions for middle-down proteoforms. The instrumental resolving power of TIMS can exceed 300, far over ~50 with TWIMS. However, R for proteins in linear IMS has been capped at ~30 by peak broadening due to conformational multiplicity. A critical advantage of TIMS is achieving for some protein conformers same peak width as for small peptides (like in FAIMS), perhaps via effective annealing upon rf field heating over extended separation time (~100 ms).

Accordingly, certain embodiments of the invention provide methods of identifying and/or isolating two or more isomers of a molecule in a sample. In certain embodiments, the method of identifying two or more isomers of a molecule in a sample comprises subjecting the sample to a step of ionization followed by ion mobility spectrometry (IMS) and mass spectrometry (MS).

The molecules that can be identified and/or isolated according to the methods described herein include biomolecules, such as peptides, proteins, antibiotics, antimicrobials, lipids, lipopeptides, carbohydrates, sugars, DNA, or RNA.

In preferred embodiments, the molecule is a polypeptide or a protein having, in its native state, i.e., without any modifications to the core amino acid sequence, a molecular weight between 400 Da to 1000 kDa which typically corresponds to a m/z range of 400-20,000.

The two or more isomers that can be separated according to the instant methods include epimers, topoisomers, or proteoforms. Additional isomers that can be identified and/or isolated according to the instant methods are known in the art and such embodiments are within the purview of the invention.

The epimers of a molecule, comprise one or more amino acids having a different optical configuration. For example, epimers of a peptide containing only L amino acids would contain one or more D amino acids.

Topoisomers of a molecule comprise different secondary structure. For example, topoisomers of a peptide having a straight chain of amino acids would contain secondary structure that changes the shape and size of the peptide. Typical examples of topoisomers of peptides are provided by lasso peptides and their corresponding branched-cyclic peptides.

Proteoforms refer to various molecular forms of proteins having an identical core amino acid sequence. Typical examples of proteoforms are provided by proteins and their phosphorylated, acetylated, or methylated versions.

The samples that can be analyzed according to the instant methods include an extract of a tissue from an animal or a plant, an extract of a microorganism, or an extract of cultured cells. A microorganism can be a bacterium, a virus, a fungus, or any combination thereof. In preferred embodiments, a sample is an extract of a microorganism that produces an anti-bacterial compound, such as an antibiotic.

The sample that can be analyzed according to the instant methods can also be a body fluid or a body secretion. Non-limiting examples of the body fluids which can be analyzed in the instant methods include amniotic fluid, aqueous humor, vitreous humor, bile, blood, cerebrospinal fluid, chyle, endolymph, perilymph, female ejaculate, lymph, mucus (including nasal drainage and phlegm), pericardial fluid, peritoneal fluid, pleural fluid, pus, rheum, saliva, sputum, synovial fluid, vaginal secretion, semen, blood, serum or plasma. Additional examples of body fluids are well known to a person of ordinary skill in the art and such embodiments are within the purview of the invention.

The sample that can be analyzed according to the instant methods can also be a fluid or a secretion from a plant or an extract of a plant or a plant tissue. Non-limiting examples of an extract of a plant tissue include an extract of root, stem, leaf, bud, and flower. Additional examples of plant secretions or plant tissue extracts are well known to a person of ordinary skill in the art and such embodiments are within the purview of the invention.

Various types of ionization sources are known in the art. A skilled artisan can determine an appropriate ionization source for use in the instant methods, for example, based on the sample to be analyzed and the molecule to be identified and/or isolated.

Similarly, various types of IMS are known in the art. Such types include traveling-wave IMS (TWIMS), trapped IMS (TIMS), or field asymmetric waveform ion mobility spectrometry (FAIMS). A skilled artisan can determine an appropriate IMS for use in the instant methods, for example, based on the sample to be analyzed and the molecule to be identified and/or isolated.

Various types of MS are known in the art. Such types include quadrupole (Q), time-of-flight (TOF), ion trap (IT), Orbitrap and Fourier transform ion cyclotron resonance (FT-ICR). A skilled artisan can determine an appropriate MS for use in the instant methods, for example, based on the sample to be analyzed and the molecule to be identified and/or isolated.

In some embodiments, the sample is subjected to a step of tandem mass spectrometry (MS/MS) before and/or after the step of IMS. Various types of MS/MS are known in the art, such as collision induced dissociation (CID), electron capture/detachment/transfer (ExD) and infrared multiphoton dissociation (IRMPD). A skilled artisan can determine an appropriate MS/MS for use in the instant methods, for example, based on the sample to be analyzed and the molecule to be identified and/or isolated.

In further embodiments, the sample is subjected to a step of metalation before the step of ESI. Metalation refers to a chemical reaction wherein a metal atom is bonded to a molecule to form a molecular complex ion with metal. Typically, metalation is performed by reacting a sample with a metal salt. In some embodiments, metalation is performed with alkali metals, such as sodium (Na), potassium (K) and cesium (Cs), alkaline earth metals, such as magnesium (Mg) and calcium (Ca), and transition metals, such as iron (Fe), cobalt (Co), Nickel (Ni), copper (Cu) and Zinc (Zn). In preferred embodiments, metalation is performed with Na, K, or Cs alkali metals. A skilled artisan can determine appropriate metal and/or metal salts for use in metalation in the instant methods based on, for example, the sample to be analyzed and the molecule to be identified and/or isolated.

In certain embodiments, the isomers of the molecules are separated and isolated upon the IMS step. The isomers separated and isolated in the instant methods can be further analyzed and characterized for beneficial biological activities of the isomers. Such activities include agonistic or antagonistic activities against target proteins, antibacterial activities, etc. As such, the instant methods can be used to identify and isolate novel biological molecules having beneficial activities.

Preferred embodiments of the invention provide methods for identifying and/or isolating two or more isomers of the polypeptide or protein, such as epimers, topoisomers, or proteoforms in a biological sample. Such methods of the invention comprise the steps of:

i) subjecting the sample to a step of ionization,
ii) optionally, before step i), subjecting the sample to a step of metalation with Na, K, or Cs,
iii) after step i), subjecting the sample to a step of IMS and MS,
iv) optionally, after step i), subjecting the sample to a step of IMS and MS/MS.

In certain such embodiments, the biological sample is an extract from an animal or a plant or a microorganism. In preferred embodiments, the biological sample is an extract of a microorganism, such as a bacterium, a virus, a fungus, or any combination thereof. In preferred embodiments, the sample is an extract of a microorganism that produces an anti-bacterial compound, such as an antibiotic.

In some embodiments, an isomer of a molecule is known to be present in a sample, particularly, a biological sample and the sample is screened for additional isomers of the known molecule. In such embodiments, the behavior of the known molecule in the IMS and/or MS steps is known. Therefore, other molecules from the sample that have similar but not identical behavior in the IMS and/or MS steps are identified and optionally, isolated. If isolated, such molecules could then be further characterized to confirm whether such molecules are indeed isomers of the known molecule. As such, certain embodiments of the invention provide methods of identifying and isolating unknown isomers of known molecules, particularly, unknown isomers of known biomolecules in biological samples.

Definitions

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%).

In the present disclosure, ranges are stated in shorthand, to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, and 0.7-1.0.

When ranges are used herein, combinations and sub-combinations of ranges (e.g., subranges within the disclosed range), specific embodiments therein are intended to be explicitly included.

Materials and Methods

Materials and Reagents for Lasso Peptide Analysis

MccJ25 was produced, from a culture of *Escherichia coli* MC4100 harboring the plasmid pTUC202, in M63 medium at 37° C. for 16 h. Anantin, BI-32169, capistruin, and siamycin I were produced by their respective native hosts (Table 2). Caulonodin I-III, sphingonodin I, syanodin I, and xanthomonin I-II, were produced heterologously in *E. coli* BL21 (DE3) under controlled conditions (Table 2). Sviceucin was produced heterologously in *Streptomyces coelicolor* transformed with the cosmid p4H7 by cultivation in GYM medium at 28° C. for 5 days. The experimental conditions are listed in detail in the Supporting Information (Table 2).

TABLE 2

Conditions for the production of lasso peptides.

| Peptide | Medium | Conditions for production | Producing Strain |
|---|---|---|---|
| Anantin | GYM | 30° C. for 2 days | *Streptomyces coerulescens* |
| BI-32169 | GYM | 28° C. for 5 days | *Streptomyces* sp. |
| Capistruin | M20 | 37° C. for 2 days | *Burkholderia thailandensis* E264 |
| Caulonodin I | M9 | 20° C. for 3 days | *E. coli* BL21 (DE3) transformed with pET41a construct |
| Caulonodin II | M9 | 20° C. for 3 days | *E. coli* BL21 (DE3) transformed with pET41a construct |
| Caulonodin III | M9 | 20° C. for 3 days | *E. coli* BL21 (DE3) transformed with pET41a construct |
| MccJ25 | M63 | 37° C. for 1 day | *E. coli* MC4100 transformed with pTUC202 |
| Siamycin I | GYM | 28° C. for 4 days | *Streptomyces* sp. |
| Sphingonodin I | M9 | 20° C. for 3 days | *E. coli* BL21 (DE3) transformed with pET41a construct |
| Sviceucin | GYM | 28° C. for 5 days | *S. coelicolor* transformed with the p4H7 cosmid |
| Syanodin I | M9 | 20° C. for 3 days | *E. coli* BL21 (DE3) transformed with pET41a construct |
| Xanthomonin I | M9 | 20° C. for 3 days | *E. coli* BL21 (DE3) transformed with pET41a construct |
| Xanthomonin II | M9 | 20° C. for 3 days | *E. coli* BL21 (DE3) transformed with pET41a construct |

The purification was started with centrifugation to separate cell pellets and culture supernatants. The lasso peptides produced by natural producers, except BI-32169 and siamycin I, were extracted from the culture supernatants by solid phase extraction using SepPak $C_8$ or $C_{18}$ reversed-phase cartridges (Waters). The elution was performed using water with 0.1% formic acid and acetonitrile mixtures with increasing content of acetonitrile, and the fractions of interest were then evaporated under reduced pressure. A second purification step was performed by reverse-phase high performance liquid chromatography (HPLC). The lasso peptides produced heterologously, BI-32169 and siamycin I, were isolated from cell pellets by extraction with methanol. The resulting extracts were directly subjected to HPLC purification steps as mentioned previously.

The branched-cyclic peptide of syanodin I was obtained by heating the lasso peptide at 95° C. for 3 h and was subsequently purified by reversed-phase HPLC. For capistruin, caulonodin III, MccJ25 and sphingonodin I, which are heat stable lasso peptides, topoisomeric variants were produced by solid-phase synthesis from Genepep (St Jean de Vedas, France). The carbonate salts of Na, K, Cs, Mg, Ca, Fe, Co, Ni, Cu and Zn were purchased from Sigma-Aldrich (St. Louis, Mo.) and Acros Organics (New Jersey, USA). The peptides were dissolved in 10 mM $NH_4Ac$ (native conditions) to 5 μM with or without 70 μM of a carbonate salt. The instrument was initially calibrated using the Tuning Mix from Agilent (Santa Clara, Calif.).

TIMS-MS Experiments

A custom nESI-TIMS unit coupled to an Impact Q-TOF mass spectrometer (Bruker, Billerica, Mass.) was employed in the methods described herein. The TIMS unit is run by custom software in LabView (National Instruments) synchronized with the MS platform controls. Sample aliquots (10 μL) were loaded in a pulled-tip capillary biased at 700-1200 V to the MS inlet. TIMS separation depends on the gas flow velocity ($v_g$), elution voltage ($V_{elution}$), ramp time ($t_{ramp}$) and base voltage ($V_{out}$). The mobility, K, is defined by:

$$K = \frac{v_g}{E} \approx \frac{A}{(V_{elution} - V_{out})} \quad (1)$$

The mobility calibration constant A was determined using known reduced mobilities of Tuning Mix components ($K_0$ of 1.013, 0.835, and 0.740 $cm^2/(V.S)$ for respective m/z 622, 922, and 1222). The scan rate ($Sr = \Delta V_{ramp}/t_{ramp}$) was optimized for every experiment. The buffer gas was $N_2$ at ambient temperature (T) with $v_g$ set by the pressure difference between the funnel entrance (P1=2.6 mbar) and exit (P2=1.1 mbar, FIG. 3). rf voltage of 200 $V_{pp}$ at 880 kHz was applied to all electrodes. The measured mobilities were converted into CCS ($Å^2$) using the Mason-Schamp equation:

$$\Omega = \frac{(18\pi)^{1/2}}{16} \frac{q}{(k_B T)^{1/2}} \left(\frac{1}{m} + \frac{1}{M}\right)^{1/2} \frac{1}{N} \times \frac{1}{K} \quad (2)$$

where q is the ion charge, $k_B$ is the Boltzmann constant, N is the gas number density, m is the ion mass, and M is the gas molecule mass. The resolving power R and resolution r are defined as $R = \Omega/w$ and $r = 1.18*(\Omega_2 - \Omega_1)/(w_1 + w_2)$, where w is the full peak width at half maximum (FWHM).

Materials and Reagents for DAACP Analysis 10 epimer pairs with 4-29 residues were tested (Table 3). The standards were selected to represent the relevant mass range while featuring single D-aa at different residues and locations, and include several cases prominent in biology. One pair (LHRH) comprises two DAACPs with one D-aa in different positions, namely pEHW$_D$SY$_D$WLRPG (SEQ ID NO: 19) and pEHWS$_D$Y$_D$WLRPG (SEQ ID NO: 20). The Achatin-I pair was synthesized by UW Biotechnology Center. Other standards were Dermorphin 1-4, Deltorphin I, Somatostatin-14, and GRF from American Peptide (Sunnyvale, Calif.), and WKYMVM (SEQ ID NO: 4), LHRH, γ-MSH, and Neurotensins from Bachem (Torrance, Calif.). The peptides were dissolved in 50:50 $H_2O$:MeOH (nESI with Synapt or TIMS) and 50:49:1 $H_2O$/MeOH/MeCOOH (ESI/Synapt) to 2 μM (nESI/Synapt), 1 μM (nESI/TIMS), and 0.1 μM (ESI/Synapt). The peptide bradykinin 1-7 (756 Da, from Sigma Aldrich) was added as internal calibrant in lower concentration. Parts of those solutions were combined into isomolar binary mixtures. For GRF, mixtures were prepared with 5 μM of D-epimer and 0.012-5 μM of L-epimer. The instrument was initially calibrated using the Tuning Mix from Agilent (Santa Clara, Calif.).

TABLE 3

Presently studied DAACPs. The D/L-residues are underlined.

| Peptide | Sequence | MW, Da |
|---|---|---|
| Achatin-I | GFAD (SEQ ID NO: 1) | 408.41 |
| Dermorphin 1-4 | YRFG (SEQ ID NO: 2) | 541.60 |
| Deltorphin I | YAFDVVG (SEQ ID NO: 3) | 769.84 |
| WKYMVM | WKYMVM (SEQ ID NO: 4) | 857.09 |
| LHRH | pEHWSY$_D$WLRPG (SEQ ID NO: 21) | 1311.45 |
| γ-MSH | YVMGHFRWDRFG (SEQ ID NO: 22) | 1570.77 |
| Somatostatin-14 | AGCKNFFWKTFTSC (SEQ ID NO: 23) | 1637.88 |
| Tyr11-Neurotensin | pELYENKPRRPYIL (SEQ ID NO: 24) | 1672.92 |
| Trp11-Neurotensin | pELYENKPRRPWIL (SEQ ID NO: 25) | 1695.96 |
| GRF | YADAIFTNSYRKVLGQLSARKLLQDIMSR (SEQ ID NO: 26) | 3357.88 |

TWIMS-MS Experiments

Two Synapt G2 systems were employed, one with a nESI source and one with high flow ESI source to probe the stability of peptide conformations and thus their separations with respect to the source conditions. Samples were infused at 0.03 μL/min (nESI) and 20 μL/min (ESI). The nESI source was operated in the positive ion mode with capillary at 2.0 KV and sampling cone at 30 V. The gas flows were 0.5 L/min $N_2$ to the source (not heated), 0.18 L/min He to the gate, and 0.09 L/min $N_2$ to the drift cell (yielding the pressure of 2.6 Torr). The ESI system used similar conditions with slightly lower pressure (2.2 Torr). The traveling wave had the height of 40 V and velocity of 600 m/s (nESI) and 650 m/s (ESI), leading to slightly different arrival times ($t_A$) in the two platforms.

Data Processing

The IMS spectra from Synapt were aligned by linear scaling (within 1%) using the internal calibrant (redundant with TIMS given the epimer separation). The IMS peaks were fitted with Gaussian distributions using OriginPro 8.5. For TIMS, the resolving power R and resolution r are defined as $R = \Omega/w$ and $r = 1.18*(\Omega_2 - \Omega_1)/(w_1 + w_2)$, where w is the full peak width at half maximum (FWHM). Same metrics for Synapt were computed with $\Omega$ replaced by $t_A$. As those depend on $\Omega$ non-linearly (close to quadratically), the true R on $\Omega$ scale differs from the apparent value (and often is approximately double that). However, the key feature resolution remains the same.

Preparation of Post-Translationally Modified Histones

The 18 H3.1 tails (residues 2-51, monoisotopic mass 5,350 Da) were probed with PTMs (me, me3, ac, and p) in biologically pertinent positions (Table 4). These were fused by native chemical ligation from two 25-residue pieces assembled by Fmoc solid-state peptide synthesis involving modified amino acids, with the product purified by LC. Protonated peptides were generated by ESI. The IMS/MS spectra were acquired for each species individually, with separations verified using equimolar mixtures of two or more variants.

TABLE 4

PTM localizations in H3 tail (ART$^3$K$^4$Q T$^6$ARK$^9$S$^{10}$
TGGK$^{14}$A PRK$^{18}$QL ATK$^{23}$AA RK$^{27}$S$^{28}$AP ATGGV
K$^{36}$KPHR Y$^{41}$RPGT VALRE (SEQ ID NO: 27))

| PTM | Mass, Da | Positions |
|---|---|---|
| me | 14.016 | K4, K9, K23 |
| me3 | 42.047 | K4, K9, K23, K27, K36 |
| ac | 42.011 | K9, K14, K18, K27, K36 |
| P | 79.966 | T3, T6, S10, S28, Y41 |

ESI-TWIMS-MS Instrumentation

In TWIMS, ions "surf" along a stack of addressable electrodes that create an axially propagating wave with spatial period L and radially confining rf field. The Synapt G2 system was employed (Waters, Milford, Mass.), where exiting ions are injected into an orthogonal reflectron time-of-flight (ToF) stage (resolving power $R_{MS}$ of 20,000) and registered. As isobaric ions fly through MS vacuum at same velocity, their temporal separation at the detector equals the difference of transit times ($t_T$) through the IMS stage determined by mobility. Unlike with drift-tube (DT) IMS, the $t_T$(K) function is complex and not reducible to closed form. Hence extracting K (to deduce the ion geometries by matching calculations or preceding measurements) necessitates a multi-point calibration using standards and is especially challenging for macromolecules because variable source conditions and field heating prior to and during IMS separation affect the geometries of relevant standards. Still, over the last decade Synapt became the prevalent IMS/MS platform, especially for proteomics and structural biology. Here, the variant separations was gauged and compared without assigning structures, thus the $t_T$ scale was not converted into Ω terms. However, as in FAIMS, an internal calibrant—a peptide of similar mass (insulin, 5.8 kDa) was spiked in to validate consistency and assure accurate spectral comparisons. The spectra were linearly scaled (within 1%) to align the $t_T$ for calibrant peaks.

The key operating parameters of TWIMS are peak voltage (U), wave speed (s), and the buffer gas identity, pressure (P), and temperature (T). Separations are mainly governed by the ion drift velocity at wave front relative to its speed:

$$c = \frac{KU}{Ls} = \frac{K_0 P_0 TU}{PT_0 Ls} \quad (1)$$

where subscripts "0" denote quantities at STP (including the reduced mobility $K_0$). The resolution is maximized at some c, so the variants with unequal mobility (reflecting different geometries and/or charge states z involved) may separate best in differing regimes. However, said maximum is near-flat over c~0.3-0.8, allowing ~4-fold variation of K with little resolution loss. The mobilities of large peptides with z>3 depend on z weakly as charging induces unfolding (elevating Ω), and the mobility range for conformers at a given z is limited as well. Hence peptide isomer separations across charge states can often be run together. Ions in TWIMS are materially field-heated, which may isomerize flexible macromolecules with mobility shifting over time. As reducing c slows the ion transit, that effect may influence the variant resolution for large peptides apart from its dependence on c for fixed geometries. Therefore, the analyses were repeated over the useful c range. A convenient way to vary c is via one wave parameter: namely, s of 650, 1000, and 1900 m/s were tried at U=40 V with N$_2$ gas at P=2.2 Torr. The gas flows were 0.5 L/min N$_2$ to the source (at 100° C.), 0.09 L/min N$_2$ to the cell (at room 7), and 0.18 L/min He to the helium gate in front of it.

The ESI source with a 32-gauge steel emitter was run with the infusion flow rate of 20 μL/min, capillary at 2.8 kV, and sampling cone at 45 V. The geometries of protein and peptide ions from ESI may keep the memory of folding in solution and thus depend on the solvent, which might allow optimizing the variant resolution. To assess that, 0.1 μM peptide solutions were tested in solvent (i) 50:49:1 methanol/water/acetic acid (pH=3), solvent (ii) predominantly organic 90:9:1 methanol/water/acetic acid, or solvent (iii) extremely acidic 97:3 water/formic acid (pH=1.5), and solvent (iv) 99:1 isopropanol/acetic acid.

The apparent TWIMS resolving power was $R=t_T/w$, where w is the full peak width at half maximum. The true R equals that metric times the logarithmic derivative of $t_T(\Omega)$, which is ~2 over the practical c range where that function is approximately quadratic.

nESI-TIMS-MS Instrumentation

In TIMS, ions radially confined by rf field in a straight section of electrodynamic funnel are axially stratified by flowing gas and retarding longitudinal dc field E. As E is ramped down, the flow (due to vacuum suction) pushes ions in order of decreasing mobility to the MS stage—here, an Impact Q-ToF mass spectrometer (Bruker, Billerica, Mass.) with $R_{MS}$=30,000. Separations depend on the gas flow velocity ($v_g$), trapping voltage ($V_{in}$), base voltage ($V_{out}$), and ramp duration ($t_{ramp}$). Each isomer emerges at characteristic "elution voltage" ($V_{elution}$):

$$K = v_g/E \approx A/(V_{elution} - V_{out}) \quad (1)$$

where A is the constant determined using internal calibrants, here the Agilent Tuning Mix components with $K_0$ of 1.013, 0.835, and 0.740 cm$^2$/(V×s) for respective m/z of 622, 922, and 1222. All electrode voltages were managed by custom software in LabView (National Instruments) synchronized with the MS platform controls. The rf amplitude was 125 V at 880 kHz frequency. The typical dc voltages were: inlet capillary at 40 V, funnel entrance at 0 V, $V_{in}$=–(50-200) V, and $V_{out}$=60 V. Lower scan rates ($Sr=\Delta V_{ramp}/t_{ramp}$) improve the resolving power. Sr=0.3 V/ms was generally adopted. The buffer gas was N$_2$, with $v_g$ set by the difference between pressures at funnel entrance (2.6 Torr) and exit (1.0 Torr). Ions were generated by a pulled-tip nano-ESI emitter (biased at 700-1200 V) from 10 μL sample aliquots (0.5 μM in 50:50 methanol/water or water) and introduced into the TIMS device via an orthogonal unheated metal capillary.

The measured mobilities were turned into £ using the Mason-Schamp equation[64]

$$\Omega = \frac{3}{16}\left[\frac{2\pi}{(k_B T)}\left(\frac{1}{m}+\frac{1}{M}\right)\right]^{1/2}\frac{ze}{NK} \quad (2)$$

where z is the ion charge state, e is elementary charge, $k_B$ is the Boltzmann constant, N is the gas number density, and M is the gas molecule mass. The resolving power is defined as[52] $R=\Omega/w$.

Example 1—Native nESI-TIMS-MS Analysis of Lasso Peptides

Inspection of the MS spectra of the lasso peptide analyzed using native nESI showed mostly low charge state species, (e.g., [M+2H]$^{2+}$) in contrast to higher charge states observed using conventional ESI in denaturing conditions (e.g., [M+2H]$^{2+}$ and [M+3H]$^{3+}$). Typical, high resolution IMS spectra corresponding to the doubly protonated species of individual lasso peptides standards are presented in FIGS. 4A-4M and the measured collision cross sections (CCS) and R metrics are listed in Table 5.

could preserve a relatively tight folding of the flexible C-terminal tail around the macrolactam ring leading to a compact conformation. This folding could be stabilized though charge solvation and/or by the formation of intramolecular interactions implying hydrogen bonds between the macrolactam ring and the penetrating C-terminal tail. An alternative scheme could include protonation of the C-ter-

TABLE 5

TIMS experimental ion-neutral collision cross sections (CCS, Å$^2$), resolving power (R) and resolution (r) for the multiply protonated species of the studied DAACPs.

| Peptide | Ion | CCS (Å$^2$) | CCS ≠ (%) | R | r |
|---|---|---|---|---|---|
| Sviceucin | [M + 2H]$^{2+}$ | 458/464/471/474/481/489/500 | | 151/81/203/168/138/58/177 | |
| Siamycin I | [M + 2H]$^{2+}$ | 467/474/478/490/498 | | 221/148/158/113/151 | |
| Xanthomonin II | [M + 2H]$^{2+}$ | 374/380/385 | | 124/145/173 | |
| Syanodin I | [M + 2H]$^{2+}$ | 383/390/396 | 0.8 (H+) | 110/113/158 | |
| | [M + 2Na]$^{2+}$ | 377/390 | | 181/182 | 0.7 (H+) |
| | [M + 2K]$^{2+}$ | 385/393 | 3.5 (Na+) | 152/180 | 3.4 (Na+) |
| | [M + 2Cs]$^{2+}$ | 396 | | 102 | 1.8 (K+) |
| Syanodin I lcm | [M + 2H]$^{2+}$ | 380/385/390/393/397 | 2.0 (K+) | 201/101/88/187/147 | 1.5 (Cs+) |
| | [M + 2Na]$^{2+}$ | 404/411 | | 145/135 | |
| | [M + 2K]$^{2+}$ | 390/396/401/409/417 | 2.0 (Cs+) | 160/142/133/102/190 | |
| | [M + 2Cs]$^{2+}$ | 404/407 | | 195/108 | |
| Xanthomonin I | [M + 2H]$^{2+}$ | 391/395/401/405 | | 174/102/113/93 | |
| Sphingonodin I | [M + 2H]$^{2+}$ | 392/397/400/410/416/423 | 4.8 | 179/132/100/152/166/169 | 2.8 |
| Sphingonodin I lcm | [M + 2H]$^{2+}$ | 405/410/414/420 | | 102/113/119/97 | |
| Caulonodin I | [M + 2H]$^{2+}$ | 410/418/425/430/443/451 | | 150/119/81/89/187/249 | |
| Caulonodin II | [M + 2H]$^{2+}$ | 422/425/429/432/437/441 | | 115/164/108/195/95/174 | |
| Caulonodin III | [M + 2H]$^{2+}$ | 431/437 | | 176/190 | |
| Anantin | [M + 2H]$^{2+}$ | 451/456/460 | | 202/156/168 | |
| Capistruin | [M + 2H]$^{2+}$ | 478/484 | 1.8 | 102/194 | 1.08 |
| Capistruin lcm | [M + 2H]$^{2+}$ | 460/468/472/487/492/499 | | 105/197/129/95/117/144 | |
| MccJ25 | [M + 2H]$^{2+}$ | 473/478/493/507 | 3.0 | 147/104/137/130 | 1.91 |
| MccJ25 lcm | [M + 2H]$^{2+}$ | 475/488/493/508 | | 170/139/115/202 | |
| BI-32169 | [M + 2H]$^{2+}$ | 452/456/466/472/480/488 | | 125/139/84/93/83/93 | | lcm: branched-cyclic peptides

The high resolution IMS profiles exhibited a remarkably large variety of IMS bands, which was not expected according to the relatively compact lasso topology. Previous TWIMS experiments usually showed a single broad arrival time distribution for the doubly protonated species; moreover, when the same peptides are now analyzed using high resolution TIMS, a higher number of IMS bands and features can be observed providing additional information on the conformational space of lasso peptides. Higher conformational diversity observed during native nESI-TIMS can be a consequence of the soft conditions that lead to the observation of multiple conformational motifs and the high resolving power of the TIMS analyzer. Multiple IMS bands also suggest the possibility to stabilize the secondary structure using several combinations of intramolecular interactions. For example, different protonation schemes can lead to charge-driven intramolecular interactions and stabilization of the conformational motif that will define a particular lasso topology. Different from traditional peptides (e.g., linear peptides), the presence of the C-terminal part threaded into the macrolactam ring (highlighted in green in FIGS. 4A-4M), and potential disulfide bonds can add additional restrains to the conformational motifs of the lasso peptides: Class II lasso peptides (without disulfide bonds) are mainly mechanically constrained by the plugs with additional intramolecular interactions between the flexible C-terminal tail (highlighted in orange in FIGS. 4A-4M) and the macrolactam ring (green). Moreover, closer inspection of the IMS profiles suggests that the amino acid composition of the C-terminal tail can impose significant folding restrictions to the lasso topology. For example, one protonation scheme minal tail leading to coulombic repulsion which unfold the flexible C-terminal tail and promote a more extended conformation. These two scenarios can be correlated to the relative abundances of the IMS bands with the length and amino acid composition of the C-terminal tail. For example, in lasso peptides long C-terminal tails (>4 residues) result in higher abundance of the most extended conformation (e.g., syanodin I, xanthomonin I, caulonodin I, and caulonodin II, FIGS. 4A-4M), while short C-terminal tails (<5 residues) result in higher abundance of the IMS bands corresponding to the most compact conformation (e.g., xanthomonin II, sphingonodin I, caulonodin III, anantin, and MccJ25, FIGS. 4A-4M). The single IMS band observed for the case of capistruin (FIG. 4k) can be a consequence of the charge solvation on Arg15 by carbonyl group of Phe18 and Asn19, and by possible hydrogen bond formation between the C-terminal carboxyl group and backbone carbonyls near Arg11 leading to a tight folding of the C-terminal tail around the macrolactam ring. In addition, the class I/III lasso peptides can be additionally stabilized by disulfide bonds preventing the unfolding of the C-terminal tail. Nevertheless, inspection of the IMS profiles of sviceucin (FIG. 4A), siamycin I (FIG. 4B) and BI-32169 (FIG. 4M) shows multiple IMS bands. Therefore, while the disulfide bonds can add restrains to the lasso topology, the interaction of the C-terminal part with the macrolactam ring can results in a variety of closely related (in the CCS domain) lasso topologies.

Example 2—Influence of Metal Ions on Peptide Topoisomer Ion Conformation

Figure 5:
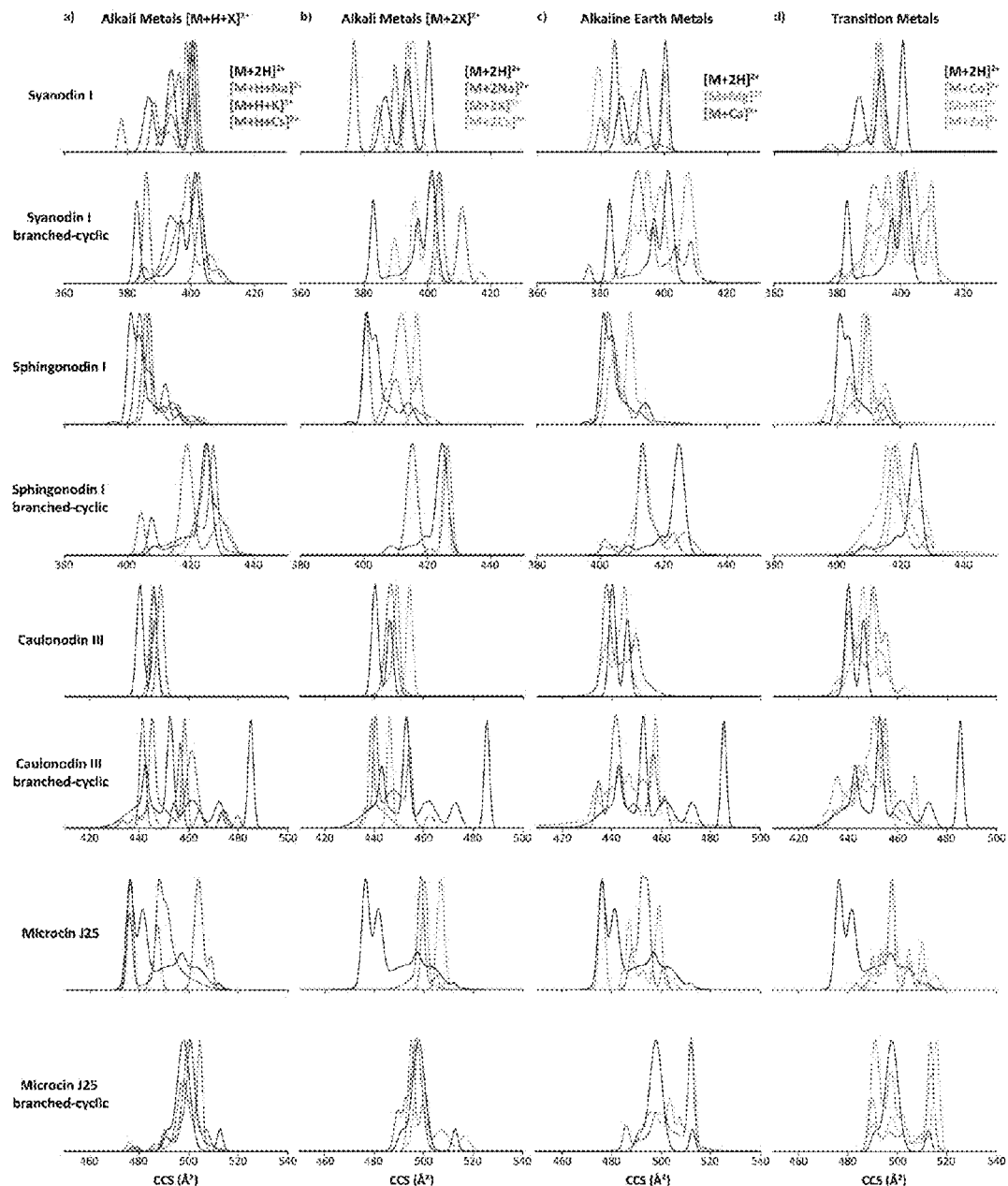
FIG. 5 shows typical TIMS spectra of lasso and branched-cyclic topoisomers of the protonated (black), sodiated (dark green and magenta), potassiated (dark and light blue), cesiated (red and orange), magnesiated (yellow), calciated (purple), cobaltiated (brown), nickelated (pink) and zincated (light green) species. A typical Sr of 0.56 V/ms was used.

The distribution of lasso and branched-cyclic peptide ions (either protonated, or containing metal ions) mostly displayed $[M+2H]^{2+}$, $[M+H+X]^{2+}$ and/or $[M+2X]^{2+}$ charge state species when using native nESI. Typical high resolution TIMS spectra for protonated and metalated forms of the individual lasso peptides (caulonodin III, microcin J25, sphingonodin I and syanodin I) and their corresponding unthreaded branched-cyclic topoisomers are shown in FIG. 5 and their collision cross sections (CCS) are listed in Table 6. As previously reported, the high resolution of TIMS permitted the separation of multiple IMS bands for the protonated lasso and branched-cyclic peptides (highlighted in black in FIG. 5). The observation of multiple compact and extended conformations suggested the presence of additional intramolecular charge-driven and/or hydrogen bond interactions, especially between residues in the flexible C-terminal tail and the macrolactam ring (Table 1). It is difficult to predict the charge localization as well as the effect of substituting protons for metal ions on the conformational space. In fact, a previous work has shown that replacing a proton by a sodium in polyalanine chains reduces the abundance of globular structures by promoting more extended conformations, while another different study reported a decrease in CCS leading to more compact structures. These results provide evidence that sodium ions interact more or less with functional groups of the peptide backbone and thereby are stabilizing the gas-phase conformation. We predict that the multiple interactions between the metal ions and the peptides under a given conformation will probably be stabilized through the electronegative groups.

TABLE 6

TIMS experimental ion-neutral collision cross sections (CCS, Å$^2$) for the doubly cationized species of syanodin I, sphingonodin I, caulonodin III and microcin J25 and its branched-cyclic topoisomer. The values involved in the resolution calculation are in bold characters.

| Peptide | Ion | CCS (Å$^2$), std. error of mean: ±0.04% | Resolution (r) |
|---|---|---|---|
| Syanodin I | $[M + 2H]^{2+}$ | 387/394/401 | 0.7 (2H) |
|  | $[M + H + Na]^{2+}$ | 378/391/394/399 |  |
|  | $[M + H + K]^{2+}$ | 394/400 | 0.2 (1Na) |
|  | $[M + H + Cs]^{2+}$ | 388/395/397/401 |  |
|  | $[M + 2Na]^{2+}$ | 377/390 | 0.5 (1K) |
|  | $[M + 2K]^{2+}$ | 384/394 |  |
|  | $[M + 2Cs]^{2+}$ | 395 | 1.7 (1Cs) |
|  | $[M + Mg]^{2+}$ | 379/384/391/395/400 |  |
|  | $[M + Ca]^{2+}$ | 380/384/390/398 | 3.4 (2Na) |
|  | $[M + Fe]^{2+}$ | 380/387/393 |  |
|  | $[M + Co]^{2+}$ | 378/382/390/392 | 1.8 (2K) |
|  | $[M + Ni]^{2+}$ | 394 |  |
|  | $[M + Cu]^{2+}$ | 379/386/392/396/401 | 1.5 (2Cs) |
|  | $[M + Zn]^{2+}$ | 378/385/389/393 |  |
| Syanodin 1 branched-cyclic | $[M + 2H]^{2+}$ | 383/389/394/397/401 | 2.2 (Mg) |
|  | $[M + H + Na]^{2+}$ | 397/399/406 |  |
|  | $[M + H + K]^{2+}$ | 385/393/397/402/409 | 1.3 (Ca) |
|  | $[M + H + Cs]^{2+}$ | 386/403 |  |
|  | $[M + 2Na]^{2+}$ | 404/411 | 2.2 (Co) |
|  | $[M + 2K]^{2+}$ | 390/396/401/409/417 |  |
|  | $[M + 2Cs]^{2+}$ | 404/407 | 1.6 (Ni) |
|  | $[M + Mg]^{2+}$ | 385/390/395/399/408 |  |
|  | $[M + Ca]^{2+}$ | 376/386/392/397/404/408 | 1.8 (Zn) |
|  | $[M + Co]^{2+}$ | 380/385/392/396/401/407/410 |  |
|  | $[M + Ni]^{2+}$ | 387/390/394/400/405/408 |  |
|  | $[M + Zn]^{2+}$ | 380/384/390/393/396/400/404/410 |  |
| Sphingonodin I | $[M + 2H]^{2+}$ | 396/401/404/414 | 2.8 (2H) |
|  | $[M + H + Na]^{2+}$ | 406/410/417/422 |  |
|  | $[M + H + K]^{2+}$ | 404/407/412/416/420 | 2.2 (1Na) |
|  | $[M + H + Cs]^{2+}$ | 407/411/416/423 |  |
|  | $[M + 2Na]^{2+}$ | 401/410/416/419 | 4.7 (1K) |
|  | $[M + 2K]^{2+}$ | 407/412/417 |  |
|  | $[M + 2Cs]^{2+}$ | 417 | 4.8 (1Cs) |
|  | $[M + Mg]^{2+}$ | 403/405/409/413 |  |
|  | $[M + Ca]^{2+}$ | 396/402/407/412 | 2.7 (2Na) |
|  | $[M + Fe]^{2+}$ | 401/409/412/418 |  |
|  | $[M + Co]^{2+}$ | 404/409/417 | 2.3 (2K) |
|  | $[M + Ni]^{2+}$ | 398/404/409/415 |  |
|  | $[M + Cu]^{2+}$ | 403/409/416 | 2.0 (2Cs) |
|  | $[M + Zn]^{2+}$ | 403/405/408/416 |  |
| Sphingonodin I branched-cyclic | $[M + 2H]^{2+}$ | 408/415/419/425 | 1.2 (Mg) |
|  | $[M + H + Na]^{2+}$ | 404/418/429 |  |
|  | $[M + H + K]^{2+}$ | 407/422/427 | 2.1 (Ca) |
|  | $[M + H + Cs]^{2+}$ | 423/425/428 |  |
|  | $[M + 2Na]^{2+}$ | 415 | 1.6 (Co) |
|  | $[M + 2K]^{2+}$ | 421/426 |  |
|  | $[M + 2Cs]^{2+}$ | 426 | 1.8 (Ni) |
|  | $[M + Mg]^{2+}$ | 402/414/427 |  |
|  | $[M + Ca]^{2+}$ | 400/404/413/423 | 2.1 (Zn) |
|  | $[M + Co]^{2+}$ | 408/418/428 |  |
|  | $[M + Ni]^{2+}$ | 409/413/416/418/424/427 |  |
|  | $[M + Zn]^{2+}$ | 408/419 |  |
| Caulonodin III | $[M + 2H]^{2+}$ | 440/446 |  |
|  | $[M + H + Na]^{2+}$ | 446 |  |
|  | $[M + H + K]^{2+}$ | 446 | 2.5 (2H) |
|  | $[M + H + Cs]^{2+}$ | 449 |  |
|  | $[M + 2Na]^{2+}$ | 446 | 2.6 (1Na) |
|  | $[M + 2K]^{2+}$ | 447/449 |  |
|  | $[M + 2Cs]^{2+}$ | 454 | 2.6 (1K) |
|  | $[M + Mg]^{2+}$ | 436/438/444/446 |  |
|  | $[M + Ca]^{2+}$ | 438/445/450 | 1.7 (1Cs) |
|  | $[M + Fe]^{2+}$ | 442/451 |  |
|  | $[M + Co]^{2+}$ | 440/447/451/455 | 1.4 (2Na) |
|  | $[M + Ni]^{2+}$ | 442/446/452 |  |
|  | $[M + Cu]^{2+}$ | 443/451/455/468 | 2.6 (2K) |
|  | $[M + Zn]^{2+}$ | 436/441/445/450/455/463 | 1.8 (2Cs) |
| Caulonodin III branched-cyclic | $[M + 2H]^{2+}$ | 438/443/453/461/472/485 |  |
|  | $[M + H + Na]^{2+}$ | 433/439/444/454/458 | 3.3 (Mg) |
|  | $[M + H + K]^{2+}$ | 441/454/457/465/473/480 |  |
|  | $[M + H + Cs]^{2+}$ | 441/445/448/461/474 | 0.6 (Ca) |
|  | $[M + 2Na]^{2+}$ | 437/441/448/454 |  |
|  | $[M + 2K]^{2+}$ | 439/444/462 | 0.8 (Co) |
|  | $[M + 2Cs]^{2+}$ | 446 |  |
|  | $[M + Mg]^{2+}$ | 434/438/440/444/448/453/458 | 1.5 (Ni) |
|  | $[M + Ca]^{2+}$ | 435/442/449/457/462 |  |
|  | $[M + Co]^{2+}$ | 436/440/444/447/451/455 | 1.6 (Zn) |
|  | $[M + Ni]^{2+}$ | 435/439/444/451/455 |  |
|  | $[M + Zn]^{2+}$ | 436/443/447/451/455/459/467 |  |
| Microcin J25 | $[M + 2H]^{2+}$ | 476/481/491/497/505/512 | 1.9 (2H) |
|  | $[M + H + Na]^{2+}$ | 477/484/487 |  |
|  | $[M + H + K]^{2+}$ | 476/488/491 | 1.7 (1Na) |
|  | $[M + H + Cs]^{2+}$ | 504/509 |  |
|  | $[M + 2Na]^{2+}$ | 497/499 | 2.5 (1K) |
|  | $[M + 2K]^{2+}$ | 500/505/509 |  |
|  | $[M + 2Cs]^{2+}$ | 507 | 0.5 (1Cs) |
|  | $[M + Mg]^{2+}$ | 476/485/487/493/500/505 |  |
|  | $[M + Ca]^{2+}$ | 488/492/494/501 | 0.3 (2Na) |
|  | $[M + Fe]^{2+}$ | 478/490/498/505/513 |  |
|  | $[M + Co]^{2+}$ | 483/489/494/498/504/511 | 1.0 (2K) |
|  | $[M + Ni]^{2+}$ | 483/488/493/498/505/510/515 |  |
|  | $[M + Cu]^{2+}$ | 491/499/507/512 | 2.1 (2Cs) |
|  | $[M + Zn]^{2+}$ | 490/494/498/505/510 |  |
| Microcin J25 branched-cyclic | $[M + 2H]^{2+}$ | 491/498/513 | 2.6 (Mg) |
|  | $[M + H + Na]^{2+}$ | 476/487/498/505 |  |
|  | $[M + H + K]^{2+}$ | 478/491/501/507 | 3.8 (Ca) |
|  | $[M + H + Cs]^{2+}$ | 479/490/500 |  |
|  | $[M + 2Na]^{2+}$ | 489/493/497 | 3.2 (Co) |
|  | $[M + 2K]^{2+}$ | 495/500 |  |
|  | $[M + 2Cs]^{2+}$ | 498/507/517 | 3.4 (Ni) |
|  | $[M + Mg]^{2+}$ | 497/504/508/513 |  |

TABLE 6-continued

TIMS experimental ion-neutral collision cross sections (CCS, Å$^2$) for the doubly cationized species of syanodin I, sphingonodin I, caulonodin III and microcin J25 and its branched-cyclic topoisomer. The values involved in the resolution calculation are in bold characters.

| Peptide | Ion | CCS (Å$^2$), std. error of mean: ±0.04% | Resolution (r) |
|---|---|---|---|
| | [M + Ca]$^2$ | 486/491/498/501/512 | 3.4 (Zn) |
| | [M + Co]$^2$ | 490/497/502/513 | |
| | [M + Ni]$^{2+}$ | 490/498/503/510/516 | |
| | [M + Zn]$^{2+}$ | 491/497/502/507/514 | |

Although solution conditions were designed to favor metalated peptide ions, protonated species were also observed. All of the metalated species studied here led to noticeable changes in the CCS distributions as compared to the protonated species (FIG. 5). CCS values generally increased upon incorporating metal ions for lasso peptides. For example, the singly cesiated species (highlighted in red in FIG. 5) of sphingonodin I, caulonodin III and microcin J25 led to a relative mobility increase of 2.7%, 2.0%, and 5.6%, respectively. In addition, the doubly alkali metalated species are shifted even more for these lasso peptides. For example, the doubly cesiated species (highlighted in orange in FIG. 5) of sphingonodin I, caulonodin III and microcin J25 led to a relative mobility increase of 5.0%, 3.1% and 6.1%, respectively. Conversely, the relative CCS appears to be smaller when replacing a proton by metal ions in syanodin I (FIG. 5). For example, the singly (highlighted in dark green in FIG. 5) and doubly (magenta) sodiated, calciated (purple) and zincated (light green) species lead to a relative mobility decrease of 0.5%, 6.0%, 4.2% and 2.0%, respectively. This suggests that syanodin I probably forms tighter binding interactions with these metals than sphingonodin I, caulonodin III and microcin J25.

In the case of the branched-cyclic peptides, the shifts of the metalated compared to protonated species are generally less pronounced than for the lasso peptides (FIG. 5). For example, the singly cesiated species (highlighted in red in FIG. 5) of the branched-cyclic form of sphingonodin I, caulonodin III and microcin J25 led to a relative mobility difference of 0.1%, 1.8%, and 0.4%, respectively (2.7%, 2.0%, and 5.6% for the corresponding lasso peptides). Furthermore, the relative mobility differences of the doubly alkali metalated species of the branched-cyclic peptides are less shifted than for the corresponding lasso peptides, as compared to the singly alkali metalated species (FIG. 5). For example, the doubly cesiated species (highlighted in orange in FIG. 5) of sphingonodin I, caulonodin III and microcin J25 led to a relative mobility increase of 0.3%, 0.2% and 0.4%, respectively (2.4%, 1.1% and 0.6% for the corresponding lasso peptides). All these features were not expected for the branched-cyclic peptides according to their unthreaded topology. This suggests that the metal ions probably bind more tightly with the flexible C-terminal part of the branched-cyclic peptides through stronger interactions involving in some cases to conformations that are more compact than the lasso structures (FIG. 5).

Figure 6A:
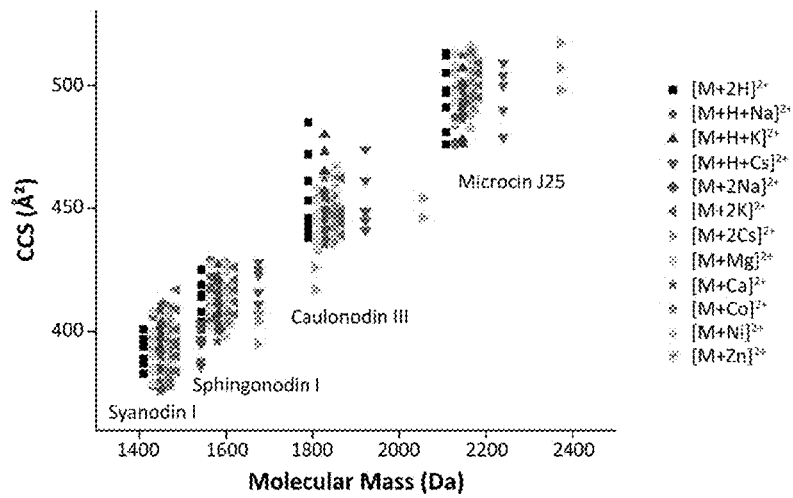
FIGS. 6A-6C show (A) CCS for all lasso and branched-cyclic peptides as a function of the molecular mass of the observed protonated (black), sodiated (dark green and magenta), potassiated (dark and light blue), cesiated (red and orange), magnesiated (yellow), calciated (purple), cobaltiated (brown), nickelated (pink) and zincated (light green) species. (B) Correlation of the <CCS> of the doubly protonated species of lasso (blue trace) and branched-cyclic (red trace) peptides as a function of the molecular mass. (C) Effect of the metalated species on the lasso (blue) and branched-cyclic (red) conformational spaces.
Figure 6B:
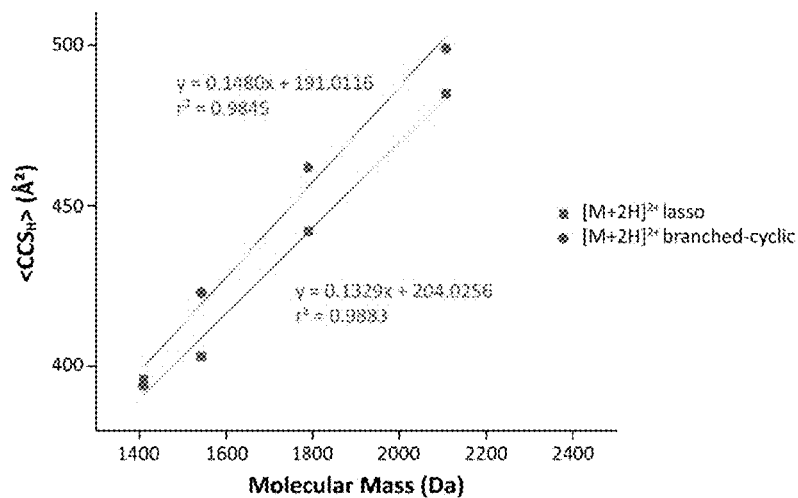

Understanding the CCS range for peptide species with similar masses provides information on the conformational spaces of different isomeric structures. A strong correlation of increasing CCS with the peptide mass is observed for syanodin I, sphingonodin I, caulonodin III and microcin J25 and their corresponding branched-cyclic topoisomers (FIG. 6A). Moreover, CCS also increase with the metal ion size and can result in rearrangements of the lasso and branched-cyclic structures. For lasso peptides, due to larger structural constraints in their secondary structure, it is expected that the interaction with the metal ion will have a lower effect than for the branched-cyclic peptides. That is, secondary structure elements of the mechanically interlocked lasso topologies may be preserved or stabilized upon metal ion binding while more changes are expected for the branched-cyclic topologies due to the unthreaded flexible C-terminal part. The relatively complex TIMS distribution (i.e., existence of multiple bands) makes it challenging to estimate the influence of metalated species on the conformational spaces of the lasso and branched-cyclic topologies. Therefore, determination of the average CCS (based on the position and intensity of all the CCS reported in Table 6) in order to get a <CCS> value for every doubly charged species proved to be a better approach. At first, we plotted the <CCS> values as a function of the molecular mass for the doubly protonated species as a way to assess the conformational trend (FIG. 6B). As observed in FIG. 6A, a strong correlation of increasing CCS with mass was obtained with a determination coefficient of 0.9883 and 0.9845 for lasso (blue trace) and branched-cyclic (red trace) peptides, respectively. In addition, these two correlations revealed that the branched-cyclic structures are more extended than the lasso ones regardless of the molecular mass (FIG. 6B).

Figure 6C:
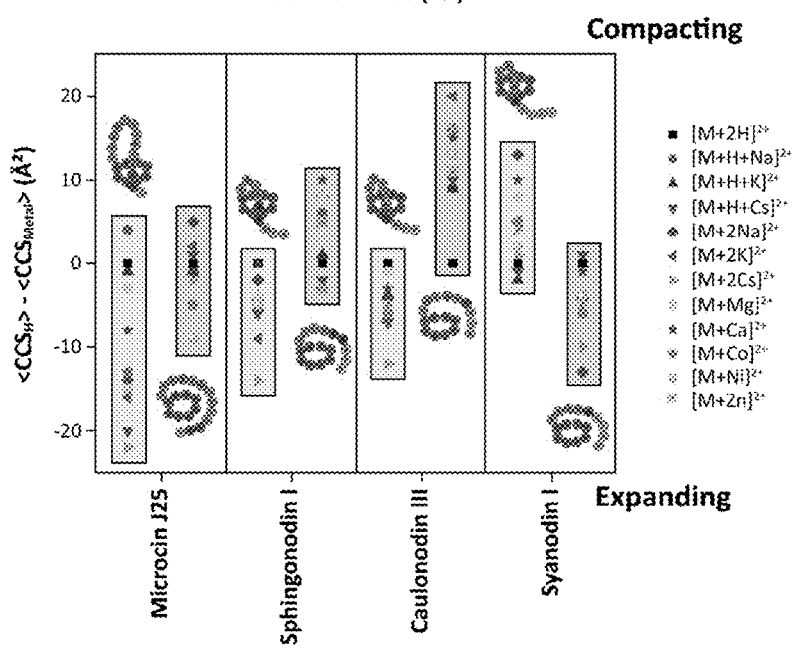

Comparison between the <CCS$_H$> and the <CCS$_{Metal}$> enables to efficiently illustrate the metalation effect on the conformational spaces of the lasso and branched-cyclic topoisomers (FIG. 6C). The lasso structures tend to expand with the metal ion adduction, as in the case of sphingonodin I, caulonodin III and microcin J25. However, this trend is not observed in the case of syanodin I where the <CCS$_{metal}$> is smaller relative to the <CCS$_H$>, suggesting a compacting behavior upon metalation (FIG. 6C). Further inspection of the lasso structures reveals that these observations are related to the lengths of the loop and the C-terminal tail of the lasso peptides. In fact, the steric stabilization of the C-terminal region inside of the macrolactam ring in lasso peptides allows only for distinct interactions of the metal ion with either residues in the loop or tail region. This limits the size of the interacting region and apparently leads to a bias of metal ion binding in either the loop or tail region, depending whichever section is larger in the respective lasso peptide. For example, the short loop (4 residues) and the long C-terminal tail (5 residues) of syanodin I suggest that the metal ions are interacting with the C-terminal tail, inducing a compacting of the flexible C-terminal tail. Conversely, for microcin J25, the larger loop (11 residues) and the shorter C-terminal tail (2 residues) indicate that the metal ions are probably interacting with the loop, implying an expansion of this region (FIG. 6C). For the unthreaded branched-cyclic peptides, incorporating a metal ion induces more or less compact/expanded structures. In fact, the branched-cyclic form of syanodin I and microcin J25 tended to expand with the metal ion adduction, while sphingonodin I and caulonodin III adopted a more compact structure. The latter behavior probably arises from the non-restricted flexible C-terminal tail that can form additional intramolecular binding interactions with the metal ions. In fact, the non-restricted C-terminal tail of the branched-cyclic topology allows metal coordination by residues throughout this region, which can result in gas-phase structures that are sometimes even more compact than the lasso peptides, for which the topology may be preserved or stabilized upon metal ion binding limiting their conformational changes.

Figures 7A, 7B:
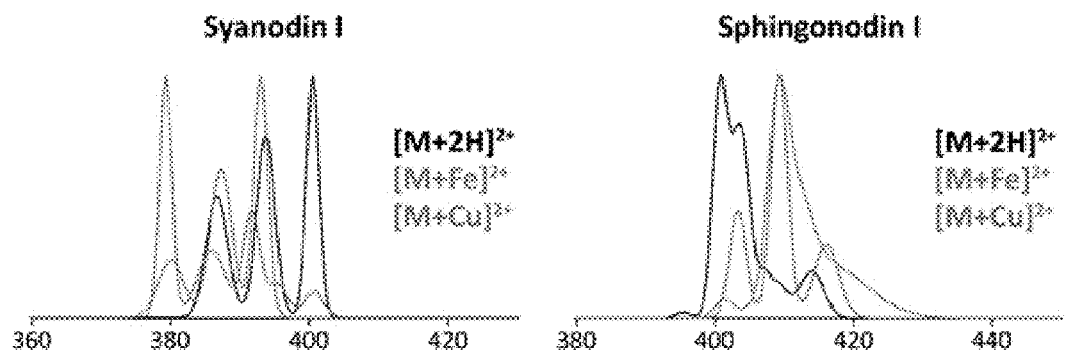
FIGS. 7A-7D show typical TIMS spectra for A) syanodin I, B) sphingonodin I, C) caulonodin III and D) microcin J25 cationized by protonated (black), ironated (red) and coppiated (green) species. A typical Sr of 0.56 V/ms was used.
Figures 7C, 7D:
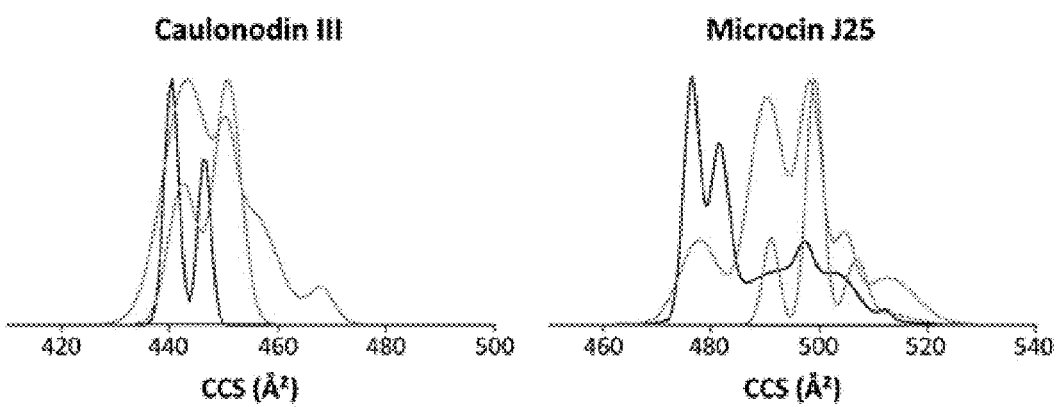
Figure 9A:
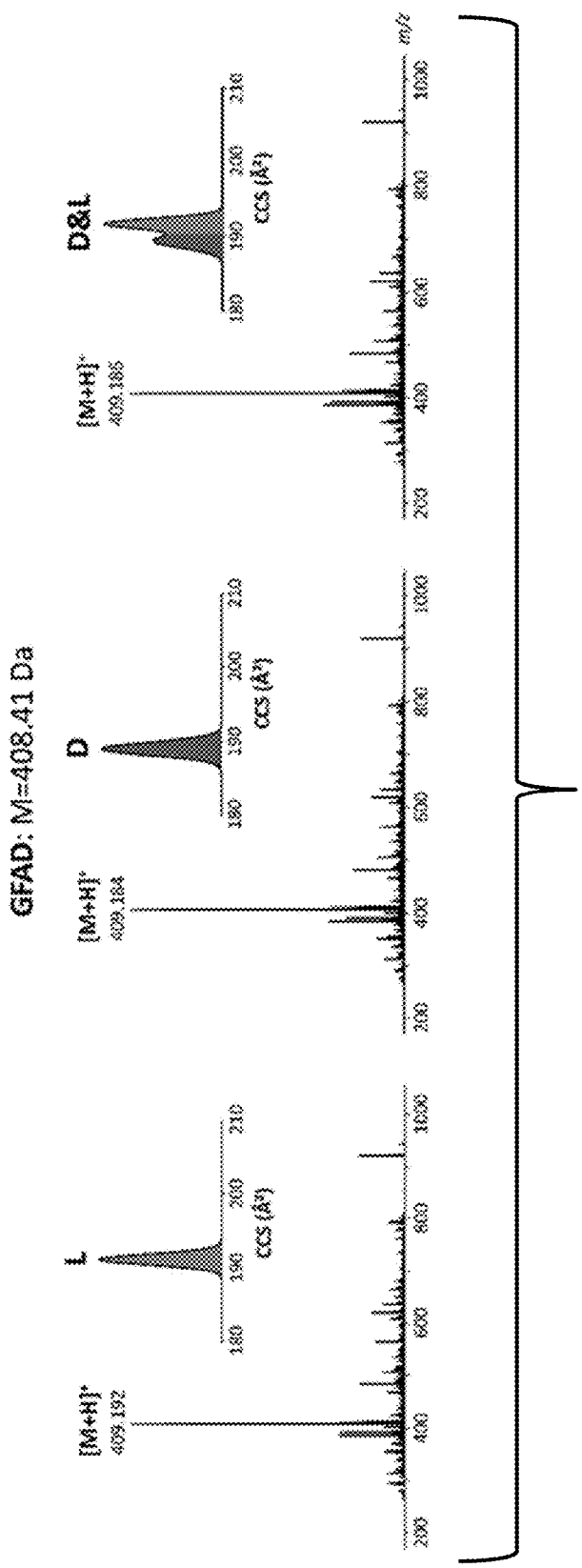
FIGS. 9A-9C show mass spectra and ion mobility profiles using TIMS of the smallest peptides A) GFAD (SEQ ID NO: 1), B) YRFG (SEQ ID NO: 2) and C) YAFDVVG (SEQ ID NO: 3). The D- and L-epimers are colored in red and blue, respectively.
Figure 9B:
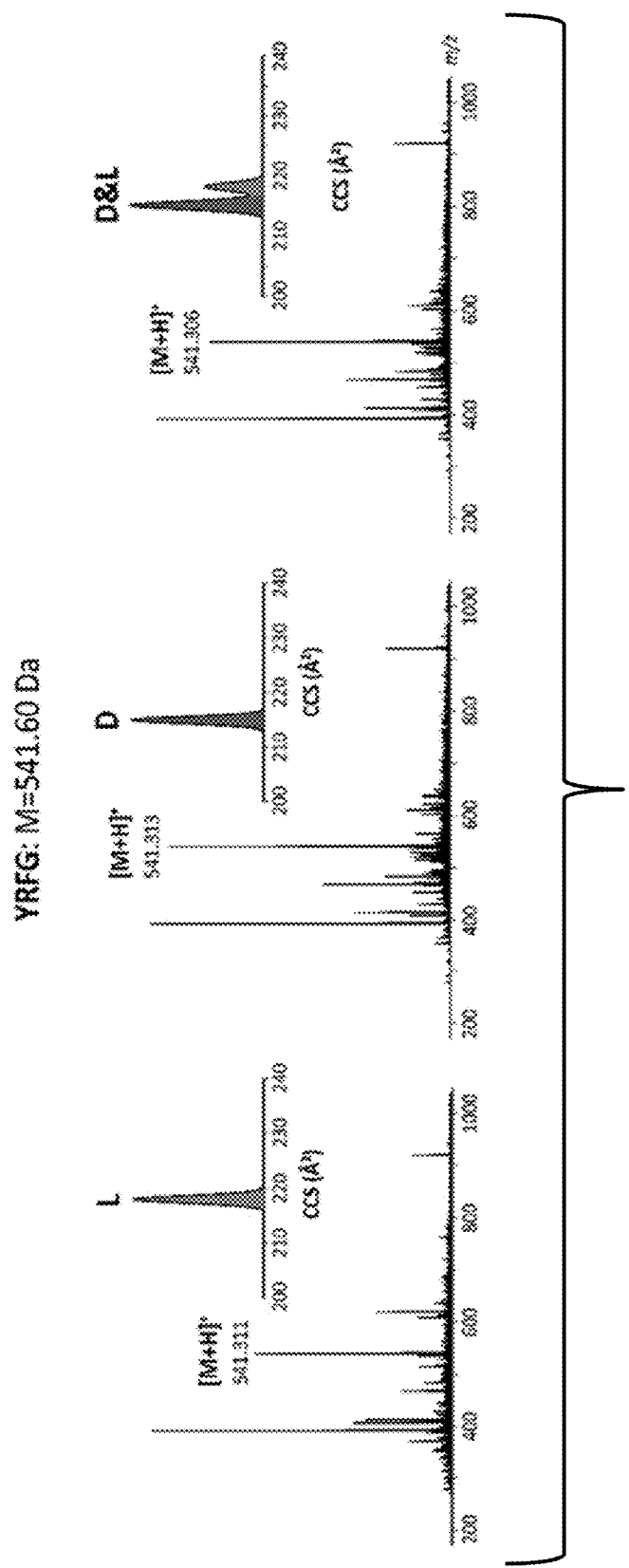
Figure 9C:
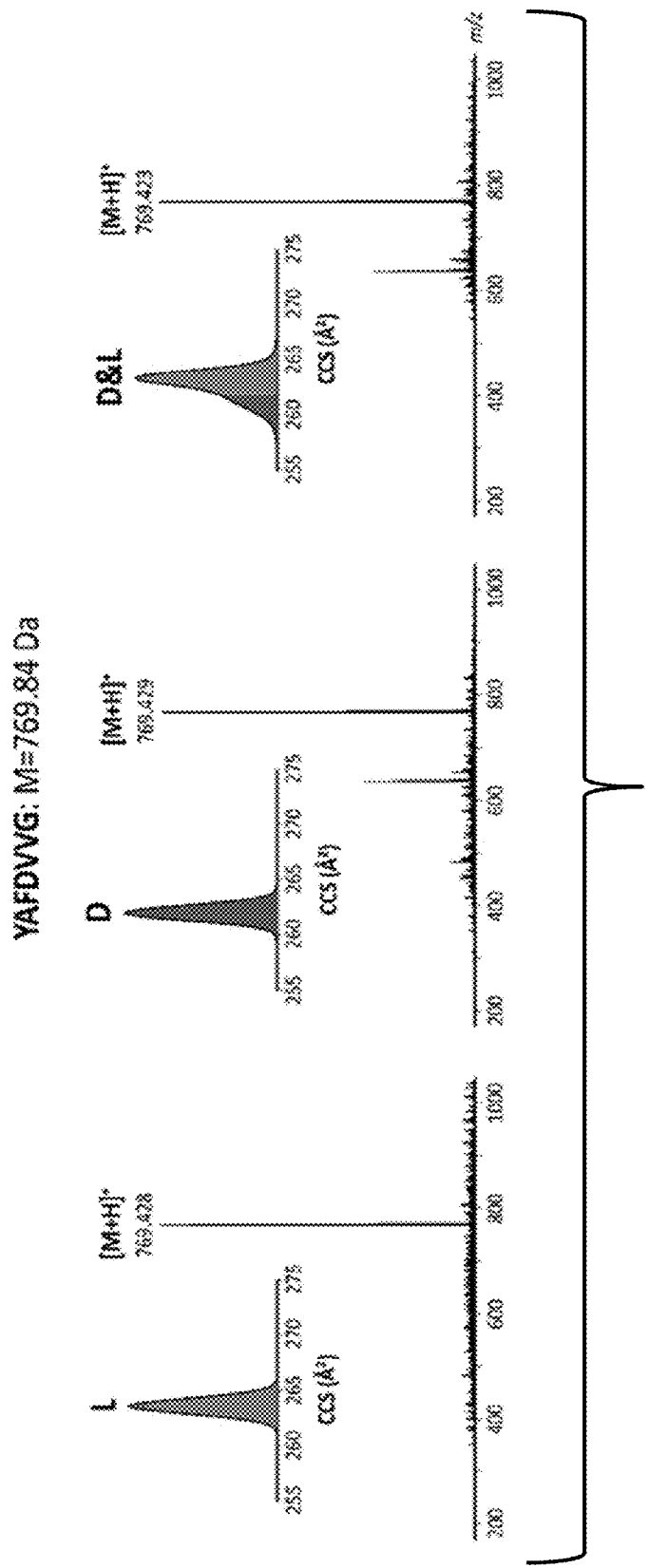
Figure 10A:
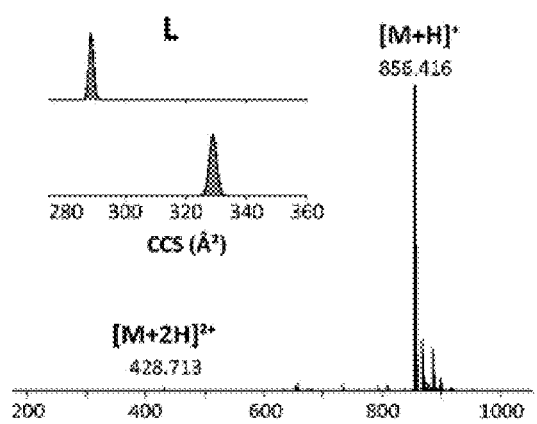
FIGS. 10A-10C show mass spectra and ion mobility profiles using TIMS of A) WKYMVM (SEQ ID NO: 4) (blue trace), B) WKYMVdM (SEQ ID NO: 5) (red trace) and C) in mixture (magenta trace).
Figure 10B:
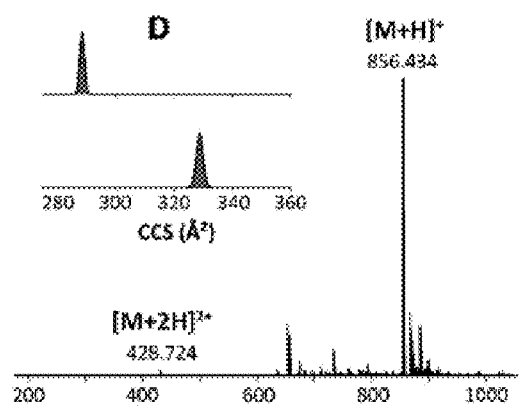
Figure 10C:
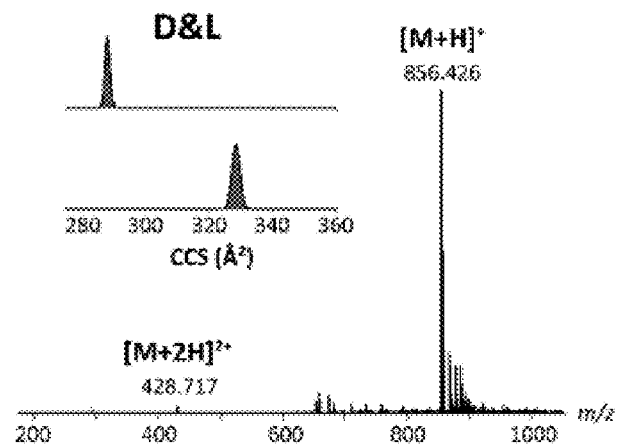

Previous reports hypothesized that lasso peptides might act like metallophores. That is, that they would act as scavenger molecules for certain metal ions, which would in turn be released upon lasso peptide isopeptidase-mediated degradation inside the cells. If this hypothesis would hold true for any lasso peptide tested in this study, a single distinct conformation would appear in the IMS distribution due to the specific interactions typical for metallophore-metal ion complexes. This was not observed with any of the tested metal ions including the typical metallophore targets as copper and iron metal ions, except for the single alkali (Na, K and Cs) species of caulonodin III and the nickelated species of syanodin I (FIGS. 5 and 7). In fact, multiple IMS bands with distinct CCS were observed in all these cases suggesting a non-specific interaction of the metal ions with the lasso peptides under these conditions.

Example 3—High Throughput Screening of Peptide Topoisomers, Epimers and Proteoforms Using nESI-TIMS-MS Separation of Lasso and Branched-Cyclic Topoisomers The potential of native nESI-TIMS-MS as a high throughput screening tool for peptide topoisomers was evaluated for capistruin, MccJ25, sphingonodin I and syanodin I, with their corresponding branched-cyclic topoisomers (FIGS. 8A-8D). Notice that while the lasso and their corresponding branched-cyclic topoisomers share the same primary amino acid sequence, they can be differentiate based on their secondary structure and fragmentation profile. However, characterizing the lasso topologies and differentiating them from their branched-cyclic topoisomers by collision induced dissociation (CID) appears quite challenging as the two topoisomers are not always clearly assigned. An alternative electron capture dissociation (ECD) technique allowed to differentiate the two topologies in their different extent of hydrogen migration (formation of $c_i^\bullet/z_j'$ from $c_i'/z_j^\bullet$). ECD appears powerful for the characterization of the lasso and branched-cyclic peptides but this approach is time-consuming as reflected by the low number of reported ECD data.

FIGS. 8A-8D show that using fast scan rates (Sr=0.3-0.56 V/ms), high mobility resolving power R of ~90-200 (with an average of ~130 required) was achieved that permitted the observation of several signature features in the IMS domain (i.e., fingerprint CCS profiles). The fast scan rates resulted in baseline separation of the sphingonodin I (r=2.8) and MccJ25 (r=1.9), nearly baseline resolution of the capistruin (r=1.1) and partial separation for syanodin I (r=0.7, FIGS. 8A-8D) topoisomers. In the case of syanodin I, slow scan rates (Sr=0.05 V/ms) are needed to resolve the topoisomers, leading to resolving powers of R~120-250 (with an average of ~190 required) and nearly baseline resolution (r~1.0) (FIG. 8C and Table 5). While previous attempts using TWIMS separations did not result in the separation of the topoisomers without the addition of chemical reagents, the high resolving power of the TIMS analyzer provided baseline analytical separation of the three lasso peptides topoisomers (Table 7). In addition to the high resolving power, accurate measurement of their relative ($\Delta\Omega_r$) and absolute ($\Delta\Omega$) CCS differences allowed clear topoisomeric differentiation: 1.8% (9 Å$^2$) for capistruin, 3.0% (15 Å$^2$) for MccJ25, and 0.8% (3 Å$^2$) for syanodin I (Table 5). FIGS. 8A-8D show that TIMS is effective for the differentiation of the lasso and branched-cyclic topologies with at least $\Delta\Omega_r$~0.8% differences.

TABLE 7

TIMS scanning rates (Sr = $\Delta V_{ramp}/t_{ramp}$, V · ms$^{-1}$) used for the doubly protonated species of the studied lasso and branched-cyclic peptides.

| Peptide | Ion | $T_{ramp}$ (ms) | $V_{ramp}$ (V) | $\Delta V_{ramp}$ (v) | Sr (V · ms$^{-1}$) | $V_{ramp}$ (V) | $\Delta V_{ramp}$ (V) | Sr (V · ms$^{-1}$) |
|---|---|---|---|---|---|---|---|---|
| Sviceucin | [M + 2H]$^{2+}$ | 500 | −200 to −50 | 150 | 0.3 | | | |
| Siamycin I | [M + 2H]$^{2+}$ | 500 | −200 to −50 | 150 | 0.3 | | | |
| Xanthomonin II | [M + 2H]$^{2+}$ | 500 | −280 to 0 | 280 | 0.56 | | | |
| Syanodin I | [M + 2H]$^{2+}$ | 500 | −200 to −50 | 150 | 0.3 | −135 to −110 | 25 | 0.05 |
|  | [M + 2Na]$^{2+}$ | 500 | −200 to −50 | 150 | 0.3 | | | |
|  | [M + 2K]$^{2+}$ | 500 | −200 to −50 | 150 | 0.3 | | | |
|  | [M + 2Cs]$^{2+}$ | 500 | −200 to −50 | 150 | 0.3 | | | |
| Syanodin I branched-cyclic | [M + 2H]$^{2+}$ | 500 | −200 to −50 | 150 | 0.3 | −135 to −110 | 25 | 0.05 |
|  | [M + 2Na]$^{2+}$ | 500 | −200 to −50 | 150 | 0.3 | | | |
|  | [M + 2K]$^{2+}$ | 500 | −200 to −50 | 150 | 0.3 | | | |
|  | [M + 2Cs]$^{2+}$ | 500 | −200 to −50 | 150 | 0.3 | | | |
| Xanthomonin I | [M + 2H]$^{2+}$ | 500 | −280 to 0 | 280 | 0.56 | — | — | — |
| Sphingonodin I | [M + 2H]$^{2+}$ | 500 | −200 to −50 | 150 | 0.3 | | | |
| Caulonodin I | [M + 2H]$^{2+}$ | 500 | −200 to −50 | 150 | 0.3 | | | |
| Caulonodin II | [M + 2H]$^{2+}$ | 500 | −200 to −50 | 150 | 0.3 | | | |
| Caulonodin III | [M + 2H]$^{2+}$ | 500 | −200 to −50 | 150 | 0.3 | | | |
| Anantin | [M + 2H]$^{2+}$ | 500 | −200 to −50 | 150 | 0.3 | | | |
| Capistruin | [M + 2H]$^{2+}$ | 500 | −280 to 0 | 280 | 0.56 | | | |
| Capistruin branched-cyclic | [M + 2H]$^{2+}$ | 500 | −280 to 0 | 280 | 0.56 | | | |
| MccJ25 | [M + 2H]$^{2+}$ | 500 | −280 to 0 | 280 | 0.56 | | | |
| MccJ25 branched-cyclic | [M + 2H]$^{2+}$ | 500 | −280 to 0 | 280 | 0.56 | | | |
| BI-32169 | [M + 2H]$^{2+}$ | 500 | −200 to −50 | 150 | 0.3 | | | |

Separation of DAACP Epimers

Separation of DAACP from its epimer containing L-aa is performed by the methods described herein. A complete separation of DAACP from its epimer would mean $R_{CH}$ capped only by the MS dynamic range, typically ~10$^5$. The DAACPs elute differently in non-chiral and chiral liquid chromatography (LC) and capillary electrophoresis (CE), and were revealed by discrepancy of retention times ($t_R$) between natural and synthetic peptides. However, those separations are slow, not always successful, and do not tell the number or location of D-aa (except by matching $t_R$ with exhaustive standard sets).

Condensed-phase separations are now increasingly complemented or replaced by ion mobility spectrometry (IMS) in gases that gained broad acceptance in proteomics thanks to speed and unique selectivity. All IMS approaches belong to two groups: linear (based on the absolute ion-molecule collision cross section or CCS, $\Omega$, at moderate electric field, E) and non-linear (based on the evolution of Q at high E). A fundamental challenge of linear IMS is the degree of orthogonality to MS, which particularly constrains the isomer resolution. Nonetheless, peptide isomers, including sequence inversions and PTM localization variants, were resolved by linear IMS using drift tubes with static uniform electric field.

Another linear IMS method is traveling-wave IMS (TWIMS) with dynamic field, implemented in Synapt quadrupole/IMS/time-of-flight MS instruments (Waters, Milford, Mass.). Even in the latest model (G2), a modest resolving power (R~30-50 on the $\Omega$ scale) has permitted only partial (if any) separation of D/L isomers for all pairs reported. While its capability for MS/MS prior to the IMS stage enables localizing D-aa by IMS of epimeric fragments, the power of that novel strategy was also limited by IMS resolution. Ionization of peptides at high concentration routinely produces oligomers. Their morphologies also differ between DAACPs and L-analogs, potentially more than those for monomers. While some epimers were easier to distinguish as multimers, the general utility of that path remains unclear. One can sometimes enhance IMS resolution using shift reagents that preferentially complex specific chemical groups, but the similarity of D- and L-aa makes that approach unlikely to succeed. However, metal cationization could improve or worsen separation of epimers by modifying their geometries in unequal ways.

In TIMS, a constant electric field component holds ions stationary against a moving buffer gas (making the effective drift length almost infinite) while a quadrupolar rf field radially confines them to avoid losses to electrodes. The TIMS devices provide R up to ~400 in a compact form and are readily integrated with various MS platforms, including time-of-flight (ToF) and Fourier Transform MS. The TIMS-MS systems have proven useful for rapid separation and structural elucidation of biomolecules, for example screening and targeted analysis of complex mixtures, tracking the isomerization kinetics, and characterizing the conformational spaces of peptides, DNA, proteins, and macromolecular complexes in native and denatured states.

This Example demonstrates the capability of linear IMS using TIMS to broadly resolve and identify D/L-peptide epimers, which commonly differ in mobility by just ~1%. The results are compared to separations of same species using the Synapt G2 platform under two different regimes.

As is normal with ESI, singly protonated species for peptides with up to seven residues were observed (FIGS. 9A-9C and 10A-10C) and multiply protonated species for longer sequences (FIGS. 11A-11E and 12A-12C). The IMS spectra were acquired for individual L- and D-stereoisomers and confirmed the result using mixtures. The measured $\Omega$ (from TIMS), $t_A$ (from Synapt), and R and r metrics for both are listed in Tables 8 and 9.

TABLE 8

TIMS experimental ion-neutral collision cross sections (CCS, Å$^2$), resolving power (R) and resolution (r) for the multiply protonated species of the studied DAACPs.

| Peptide | Ion | CCS (Å$^2$), standard error: ±0.001% | CCS ≠ (%) | R | r |
|---|---|---|---|---|---|
| Achatin-I | [M + H]$^+$ | 191.7 | 1.1 | 190 | 1.20 |
| (D-Phe2)-Achatin-I | [M + H]$^+$ | 189.6 | | 181 | |
| Dermorphin (1-4) | [M + H]$^+$ | 218.2 | 1.4 | 235 | 1.86 |
| (D-Arg2)-Dermorphin (1-4) | [M + H]$^+$ | 215.2 | | 222 | |
| Deltorphin I | [M + H]$^+$ | 263.5 | 0.6 | 223 | 0.90 |
| (D-Ala2)-Deltorphin I | [M + H]$^+$ | 262.0 | | 336 | |
| WKYMVM | [M + H]$^+$ | 288.9 | 0.03 (1+) | 301 | 0.07 |
|  | [M + K]$^+$ | 293.7 | | 237 | (1+) |
|  | [M + 2H]$^{2+}$ 329.0 | | 0.8 (K+) | 117 | 1.04 |
| WKYMVdM | [M + H]$^+$ | 288.8 | | 301 | (K+) |
|  | [M + K]$^+$ | 291.4 | 0.06 (2+) | 256 | 0.04 |
|  | [M + 2H]$^{2+}$ 328.8 | | | 124 | (2+) |
| (D-Ser4-D-Trp6)-LHRH | [M + 2H]$^{2+}$ 386.3 | | 2.2 | 149 | 2.03 |
| (D-Tyr5-D-Trp6)-LHRH | [M + 2H]$^{2+}$ 372.9/377.8 | | | 186/157 | |
| γ-MSH | [M + 2H]$^{2+}$ 398.4 | | 3.0 (2+) | 173 | 2.54 |
|  | [M + 3H]$^{3+}$ 469.2 | | | 156 | (2+) |
| (D-Trp8)-γ-MSH | [M + 2H]$^{2+}$ 410.7 | | 0.2 (3+) | 121 | 0.17 |
|  | [M + 3H]$^{3+}$ 468.3 | | | 140 | (3+) |
| Somatostatin-14 | [M + 2H]$^{2+}$ 432.0 | | 0.7 (2+) | 228 | 1.25 |
|  | [M + 3H]$^{3+}$ 463.2/470.9 | | | 179/124 | (2+) |
| (D-Trp8)-Somatostatin-14 | [M + 2H]$^{2+}$ 429.1 | | 0.04 (3+) | 226 | 0.04 |
|  | [M + 3H]$^{3+}$ 471.1 | | | 137 | (3+) |
| (L-Tyr11)-Neurotensin | [M + 2H]$^{2+}$ 426.7/434.4/438.8/447.0 | | 1.5 (2+) | 195/208/184/95 | 1.51 |
|  | [M + 3H]$^{3+}$ 491.8/496.1/525.2/531.4 | | | 175/145/66/139 | (2+) |
| (D-Tyr11)-Neurotensin | [M + 2H]$^{2+}$ 427.9/432.8/451.2 | | 0.3 (3+) | 144/62/58 | 0.23 |
|  | [M + 3H]$^{3+}$ 490.7/494.9/523.7/529.8 | | | 123/104/179/121 | (3+) |
| (L-Trp11)-Neurotensin | [M + 2H]$^{2+}$ 439.5/446.2/452.0/458.3/462.3 | | 2.3 (2+) | 96/114/168/249/251 | 1.58 |
|  | [M + 3H]$^{3+}$ 480.0/485.2/495.9/500.5/529.1/535.3 | | | 214/217/162/148/138/156 | (2+) |
| (D-Trp11)-Neurotensin | [M + 2H]$^{2+}$ 429.2/434.6/452.4/459.7 | | 0.6 (3+) | 131/107/115/102 | 0.44 |
|  | [M + 3H]$^{3+}$ 467.2/490.6/498.8/521.4/532.9 | | | 187/122/106/128/90 | (3+) |
| GRF | [M + 3H]$^{3+}$ 752.2 | | 2.2 (3+) | 184 | 2.40 |
|  | [M + 4H]$^{5+}$ 852.6 | | | 67 | (3+) |
|  | [M + 5H]$^{5+}$ 943.3 | | 0.11 (4+) | 147 | 0.05 |

TABLE 8-continued

TIMS experimental ion-neutral collision cross sections (CCS, Å$^2$), resolving power (R) and resolution (r) for the multiply protonated species of the studied DAACPs.

| Peptide | Ion | CCS (Å$^2$), standard error: ±0.001% | CCS ≠ (%) | R | r |
|---|---|---|---|---|---|
| (D-Ala2)-GRF | [M + 3H]$^{3+}$ | 736.0 | | 189 | (4+) |
| | [M + 4H]$^{5+}$ | 851.7 | 0.02 (5+) | 96 | 0.02 |
| | [M + 5H]$^{5+}$ | 943.5 | | 144 | (5+) |

TABLE 9

Synapt (ESI) experimental drift times (t$_D$, ms), resolving power (R) and resolution (r) for the multiply protonated species of the studied DAACPs.

| Peptide | Ion | Drift Time (ms) | t$_D$ ≠ (%) | R | r |
|---|---|---|---|---|---|
| Achatin-I | [M + H]$^+$ | 4.10 | 0.2 | 22 | 0.03 |
| (D-Phe2)-Achatin-I | [M + H]$^+$ | 4.09 | | 26 | |
| Deltorphin I | [M + H]$^+$ | 7.45 | 1.7 | 27 | 0.28 |
| (D-Ala2)-Deltorphin I | [M + H]$^+$ | 7.32 | | 28 | |
| WKYMVM | [M + H]$^+$ | 8.86 | 0.2 (1+) | 27 | 0.04 |
| | [M + 2H]$^{2+}$ | 3.27 | | 28 | (1+) |
| WKYMVdM | [M + H]$^+$ | 8.88 | 0.6 (2+) | 26 | 0.10 |
| | [M + 2H]$^{2+}$ | 3.29 | | 30 | (2+) |
| (D-Ser4-D-Trp6)-LHRH | [M + 2H]$^{2+}$ | 4.41 | 3.6 | 29 | 0.65 |
| (D-Tyr5-D-Trp6)-LHRH | [M + 2H]$^{2+}$ | 4.25 | | 30 | |
| γ-MSH | [M + 2H]$^{2+}$ | 5.17 | 0.8 (2+) | 22 | 0.12 |
| | [M + 3H]$^{3+}$ | 3.36 | | 35 | (2+) |
| (D-Trp8)-γ-MSH | [M + 2H]$^{2+}$ | 5.21 | 2.4 (3+) | 33 | 0.47 |
| | [M + 3H]$^{3+}$ | 3.28 | | 31 | (3+) |
| (L-Tyr11)-Neurotensin | [M + 2H]$^{2+}$ | 5.58 | 2.0 (2+) | 22 | 0.53 |
| | [M + 3H]$^{3+}$ | 3.84 | | 16 | (2+) |
| (D-Tyr11)-Neurotensin | [M + 2H]$^{2+}$ | 5.46/5.82 | 0.8 (3+) | 29/21 | 0.06 |
| | [M + 3H]$^{3+}$ | 3.62/3.86 | | 33/26 | (3+) |

Synapt and TIMS Separation for Protonated Peptides

Figure 13A:
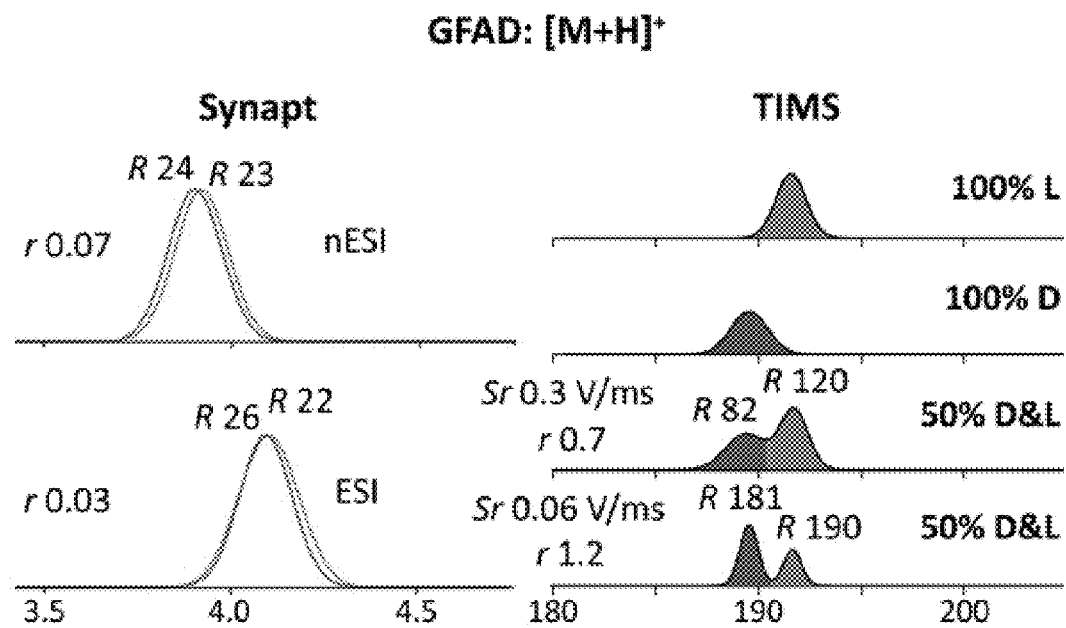
FIGS. 13A-13C show IMS spectra using Synapt (left) and TIMS (right) for small protonated peptides (A) GFAD (SEQ ID NO: 1), (B) YRFG (SEQ ID NO: 2) and (C) YAFDVVG (SEQ ID NO: 3). The epimers are colored in blue (L) and red (D). The TIMS spectra for mixtures employed different scan rates Sr as marked. The R and r values are given.
Figure 13B:
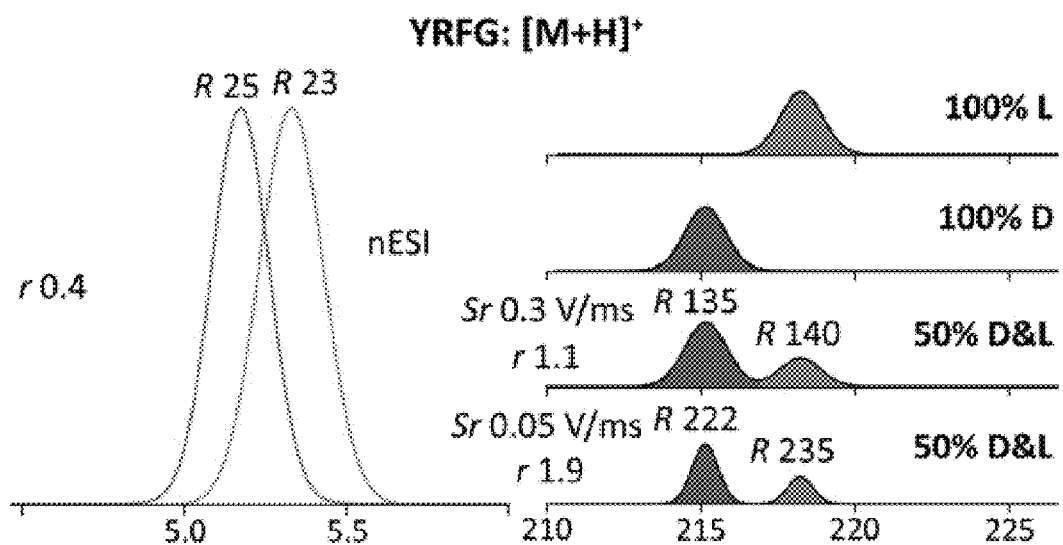
Figure 13C:
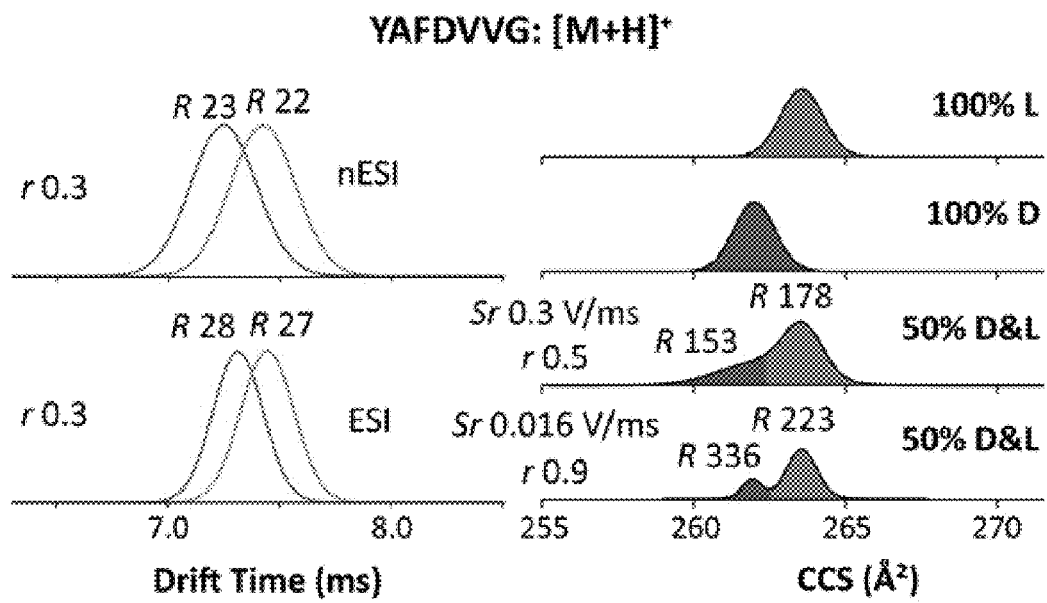

The smallest peptides GFAD (SEQ ID NO: 1), YRFG (SEQ ID NO: 2), and YAFDVVG (SEQ ID NO: 3) exhibit [M+H]$^+$ ions that yield a single peak in IMS spectra (FIGS. 13A-13C). With Synapt, the expected apparent R of ~25 allows very little (if any) epimer resolution: the features coincide for GFAD (SEQ ID NO: 1) (r<0.1) and just slightly differ for YRFG (SEQ ID NO: 2) (r=0.4) and YAFDVVG (SEQ ID NO: 3) (r=0.3). The two TWIMS instruments with dissimilar sources yield identical outcomes, showing excellent interlab reproducibility and pointing to thermalized peptide conformations in the IMS cell. The separation power of TIMS is drastically higher at any reasonable Sr (Tables 8 and 9). With fast scan rates [Sr=0.3 V/ms], R of ~120-180 (on average, ~140) was achieved for well-resolved features. This delivers nearly baseline resolution for YRFG (SEQ ID NO: 2) (r=1.1) and partial separation for GFAD (SEQ ID NO: 1) (r=0.7) and YAFDVVG (SEQ ID NO: 3) (r=0.5). Slow scan rates [Sr=0.016-0.06 V/ms] led to higher R~180-340 (on average, ~230), providing (nearly) baseline resolution (r~1-2) for all three pairs (FIGS. 13A-13C and Table 8). Hence the resolution advantage of TIMS over Synapt is 5-10 fold, depending on the Sr utilized.

Full resolution of epimers permits accurate measurement of their relative (ΔΩ$_r$) and absolute (ΔΩ) mobility differences: 1.1% (2.1 Å$^2$) for GFAD (SEQ ID NO: 1), 1.4% (3.0 Å$^2$) for YRFG (SEQ ID NO: 2), and 0.6% (1.5 Å$^2$) for YAFDVVG (SEQ ID NO: 3) (Table 8). Therefore, TIMS can baseline-resolve the epimers with ~1.5% difference using fast scan rates and half that with slow scan rates. The D-epimer has lower Ω in all cases. This qualitatively matches the results with Synapt, but ΔΩ$_r$ was significantly greater for GFAD (SEQ ID NO: 1) than YAFDVVG (SEQ ID NO: 3) with TIMS and conversely with Synapt. That must reflect a distinction between time-averaged peptide geometries in two separations, presumably due to the (i) unequal heating of ions by different rf fields in TIMS and Synapt cells, and/or (ii) conformational evolution of peptides during much longer separation in TIMS (~50-300 ms) vs. Synapt (~5-10 ms)—such transitions on the ~10-300 ms timescale have been noted in ion trap/IMS systems.

Figure 11A:
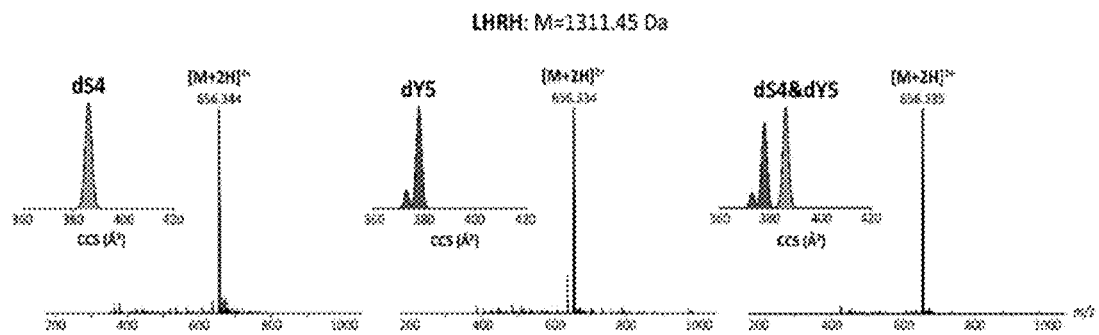
FIGS. 11A-11E show Mass spectra and ion mobility profiles using TIMS of the larger peptides A) LHRH, B) γ-MSH, C) somatostatin-14, D) Tyr11-neurotensin and E) Trp11-neurotensin. The D- and L-epimers are colored in red and blue, respectively.
Figure 11B:
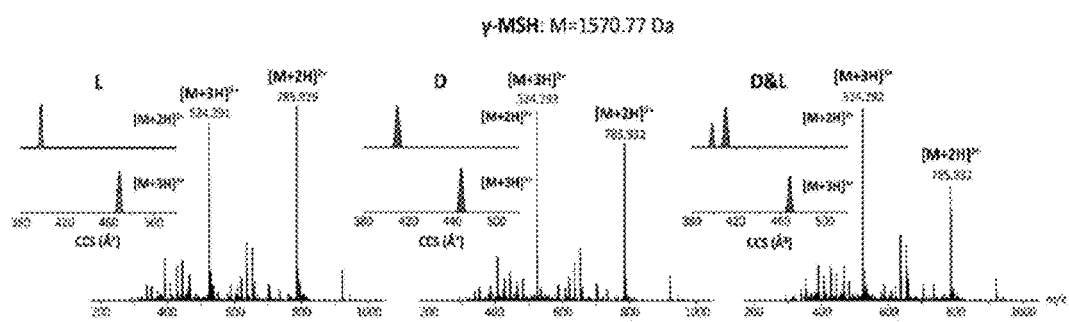
Figure 11C:
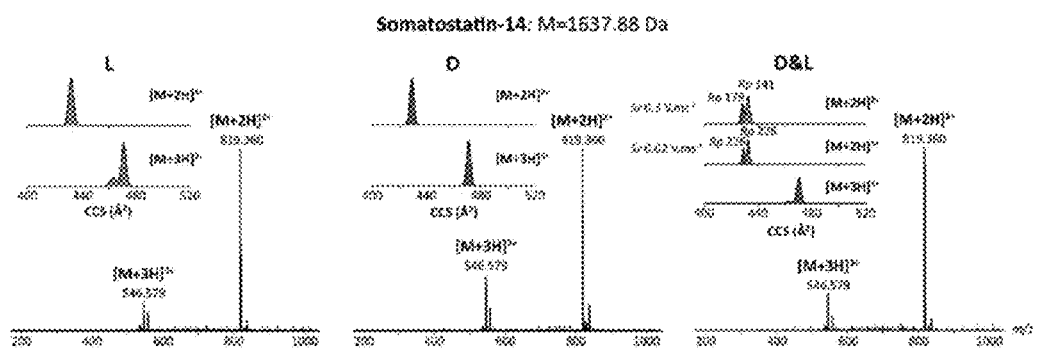
Figure 11D:
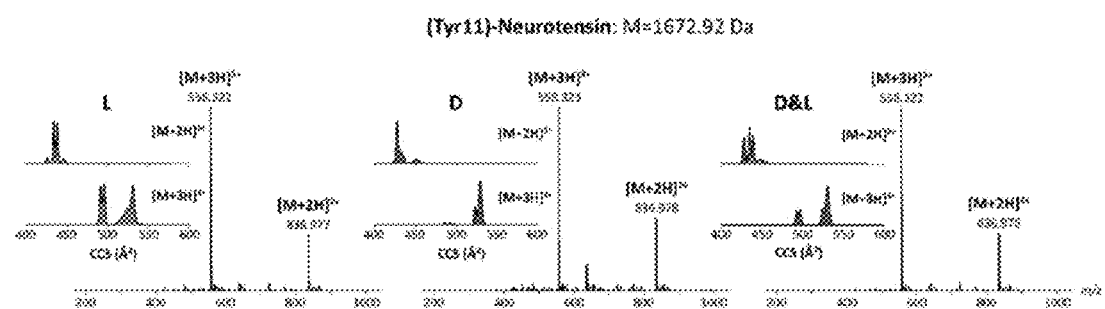
Figure 11E:
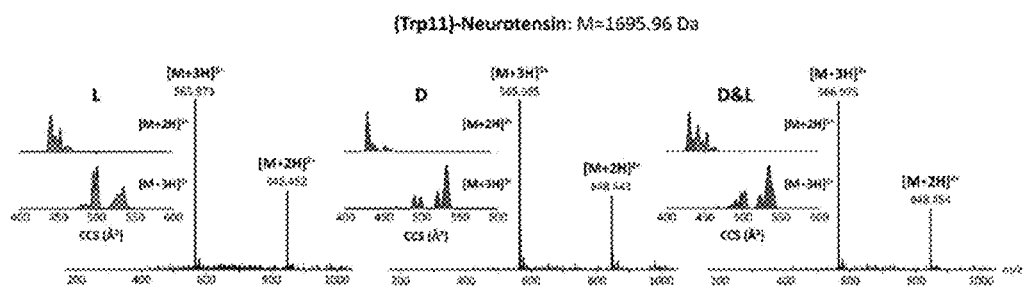
Figure 14A:
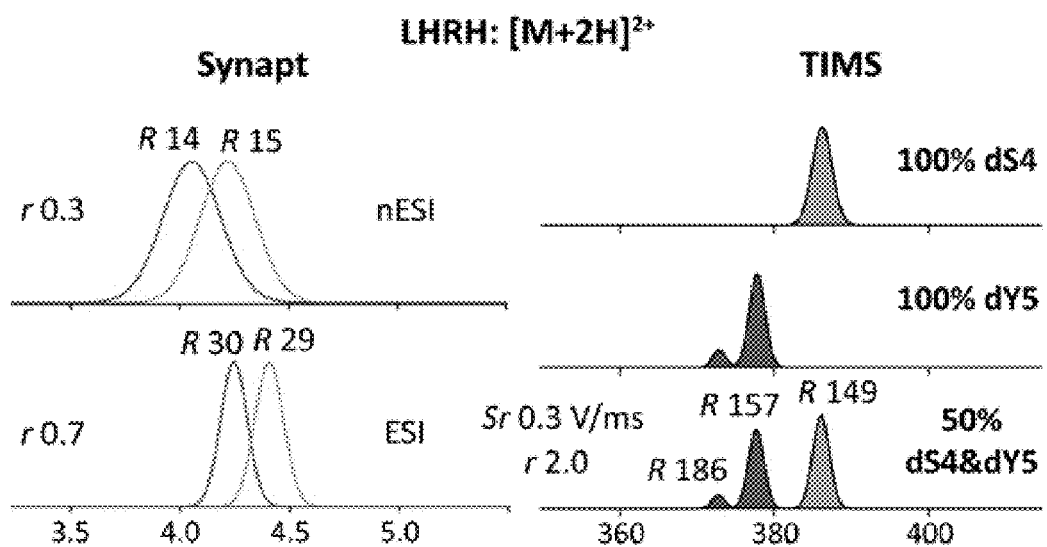
FIGS. 14A-14C show IMS spectra using Synapt (left) and TIMS (right) for larger $[M+2H]^{2+}$ peptides (A) LHRH, (B) γ-MSH, (C) Tyr11-neurotensin, for TIMS obtained using fast scan rates. The epimers are colored in blue (L) and red (D). The R and r values are given.
Figure 14B:
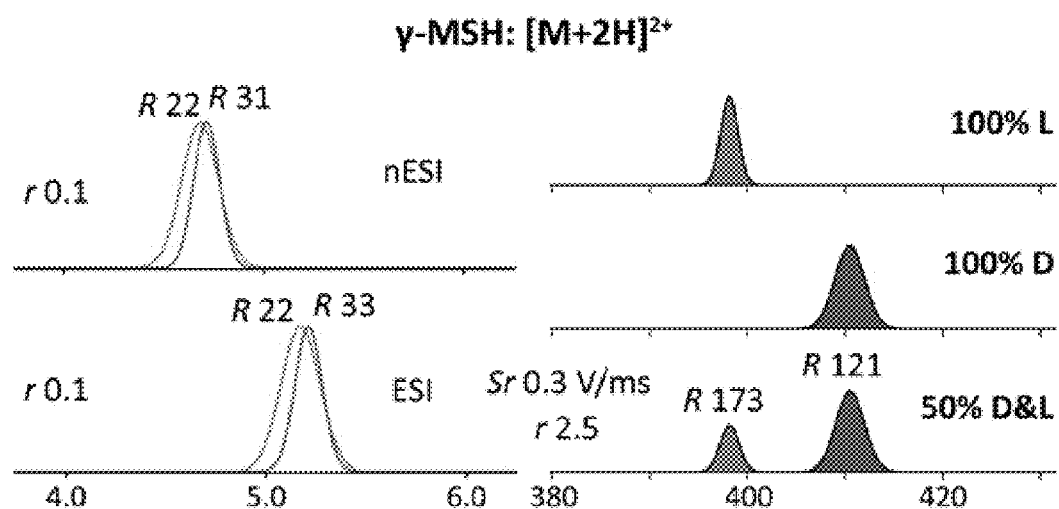
Figure 14C:
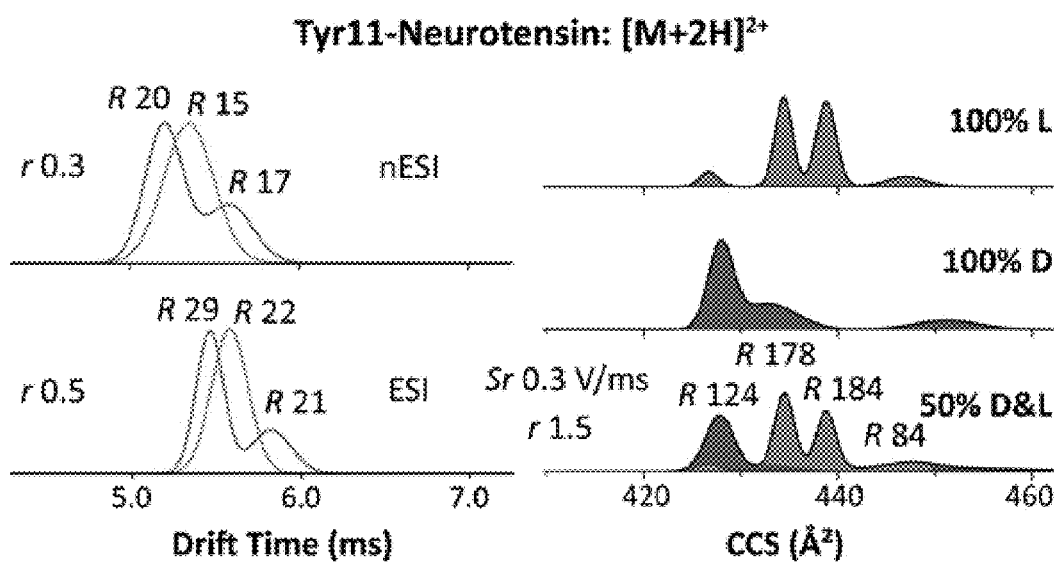

The outcomes for larger doubly protonated peptides LHRH, γ-MSH, somatostatin-14, and both neurotensins, are broadly similar (FIGS. 11A-11E and 14A-14C). The resolving power of all IMS methods goes up for higher charge states in view of slower diffusion at equal mobility. Indeed, the R values slightly increase for the [M+2H]$^{2+}$ ions (on average, to ~30 in Synapt and ~160 in TIMS with fast scan rates) while the relative advantage of TIMS remains at 5-6 times. The IMS spectra from two Synapt platforms stay consistent and show material differences between all epimers, but none suffices for baseline resolution. At best, r=0.7 for LHRH allows clean filtering of each isomer near its peak apex. The separation for other pairs (incl. the important γ-melanocyte stimulating hormone-MSH) is much worse. With TIMS, baseline resolution (r=1.5-2.5) is attained in all cases except somatostatin-14 already with the fast scan rate. While higher R helped, that is mostly due to greater ΔΩ compared to [M+H]$^+$ ions [2.2% (8.5 Å$^2$) for LHRH, 3.0% (12.3 Å$^2$) for γ-MSH, 1.5% (6.5 Å$^2$) for Tyr11-neurotensin, and 2.3% (10.3 Å$^2$) for Trp11-neurotensin]: the lowest 1.5% exceeds the highest for [M+H]$^+$ ions (FIGS. 13A-13C) where Sr=0.3 V/(ms) provided baseline separation. The doubling of mean ΔΩ$_r$ from 1.0% for [M+H]$^+$ ions to 2.2% for [M+2H]$^{2+}$ ions here probably reflects a greater diversity of folds accessible for larger peptides, which statistically expands the spread between epimer geometries. However, that diversity also tends to raise the number of populated conformers, which begin obstructing epimer resolution by taking up the separation space (FIGS. 14C and 11D-11E). For somatostatin-14, reducing Sr to 0.02 V/(ms) increased R to ~230 and resolution to near-baseline (r=1.3) with ΔΩ$_r$=0.7% (ΔΩ$_r$=0.9 Å$^2$, FIG. 11C). This small shift may ensue from the conformational constraint by the disulfide link, although ΔΩ$_r$ is yet smaller for WKYMVM (SEQ ID NO: 4) without one (below). With γ-MSH, the Ω value is much greater for D than L epimer (FIG. 14B).

Figure 15A:
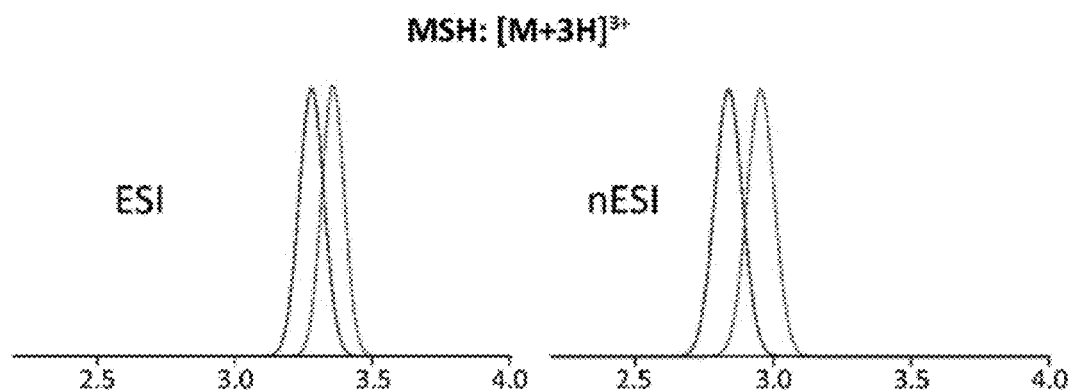
FIGS. 15A-15C show synapt profiles of the A) triply protonated γ-MSH, B) triply protonated Tyr11-neurotensin, and C) doubly protonated WKYMVM (SEQ ID NO: 4). L- and D-stereoisomers are colored in blue and red, respectively.
Figure 15B:
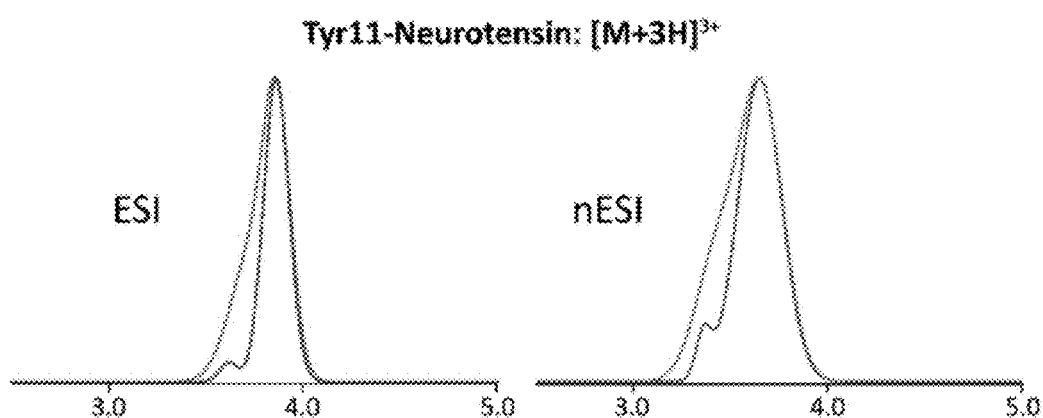
Figure 15C:
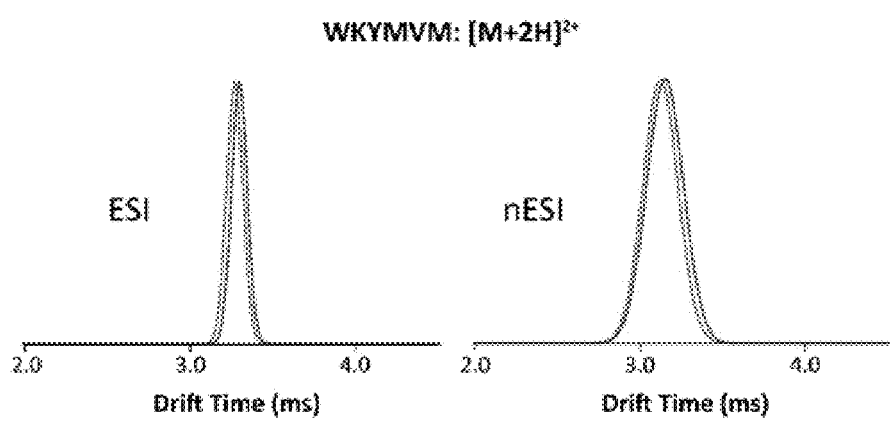

The γ-MSH, somatostatin-14, and neurotensins also exhibit [M+3H]$^{3+}$ ions. Since the [M+2H]$^{2+}$ ions of these epimers were baseline-separated in TIMS, no other conditions were explored (FIGS. 11A-11E). Under fast scan rates (Sr=0.3 V/(ms) and R~150), the Ω for D-epimer of γ-MSH is below that for L-epimer by 0.2% (0.9 Å$^2$), meaning no resolution (r=0.2). This order inversion compared to [M+2H]$^{2+}$ ions matches that found with Synapt (FIGS. 15A-15C), but ΔΩ$_r$ of >2% provides r=0.5 despite R of only ~30. For somatostatin-14, the main epimer peaks coincide, although L-epimer may be filtered out at its minor peak with lower by 1.7% (7.9 Å$^2$). For neurotensins, both epimers exhibit four to eight features occupying wide Ω ranges, and the shapes and widths of some indicate further merged conformers. This peak widening and multiplicity preclude good resolution. Here, lower Ω values broadly belong to the L-isomers. The spectra from Synapt overall agree with these findings (FIGS. 15A-15C).

Separations of Middle-Down Proteoforms

Comprehensive characterization of proteomes comprising same proteins with distinct post-translational modifications (PTMs) is a staggering challenge. Many such proteoforms are isomers (localization variants) that require separation followed by top-down or middle-down mass-spectrometric analyses, but condensed-phase separations are ineffective in those size ranges. The variants for "middle-down" peptides were resolved by differential ion mobility spectrometry, also known as field asymmetric waveform ion mobility spectrometry (FAIMS) relying on the mobility increment at high electric fields, but not previously by linear IMS based on the absolute mobility. This Example, using complete histone tails with diverse PTMs on alternative sites, demonstrates that high-resolution linear IMS, particularly, TIMS, broadly resolves the variants of ~50 residues fully or into binary mixtures quantifiable by tandem MS. Such resolution may be largely attributed to orthogonal separations across charge states. Separations using TWIMS and/or involving various timescales and electrospray ionization source conditions are similar (with lower resolution for TWIMS), showing the transferability of results across linear IMS instruments.

TWIMS Separations of Proteoforms

Using solvent (i), protonated ions with z=5-11 for all variants were observed. This range is lower than z=8-12 examined in nano-ESI/FAIMS experiments with same solvent, which reflects a different ion source and greater instrumental sensitivity that allows collecting IMS data for more states (although with low signal at z=5).

Figure 16:
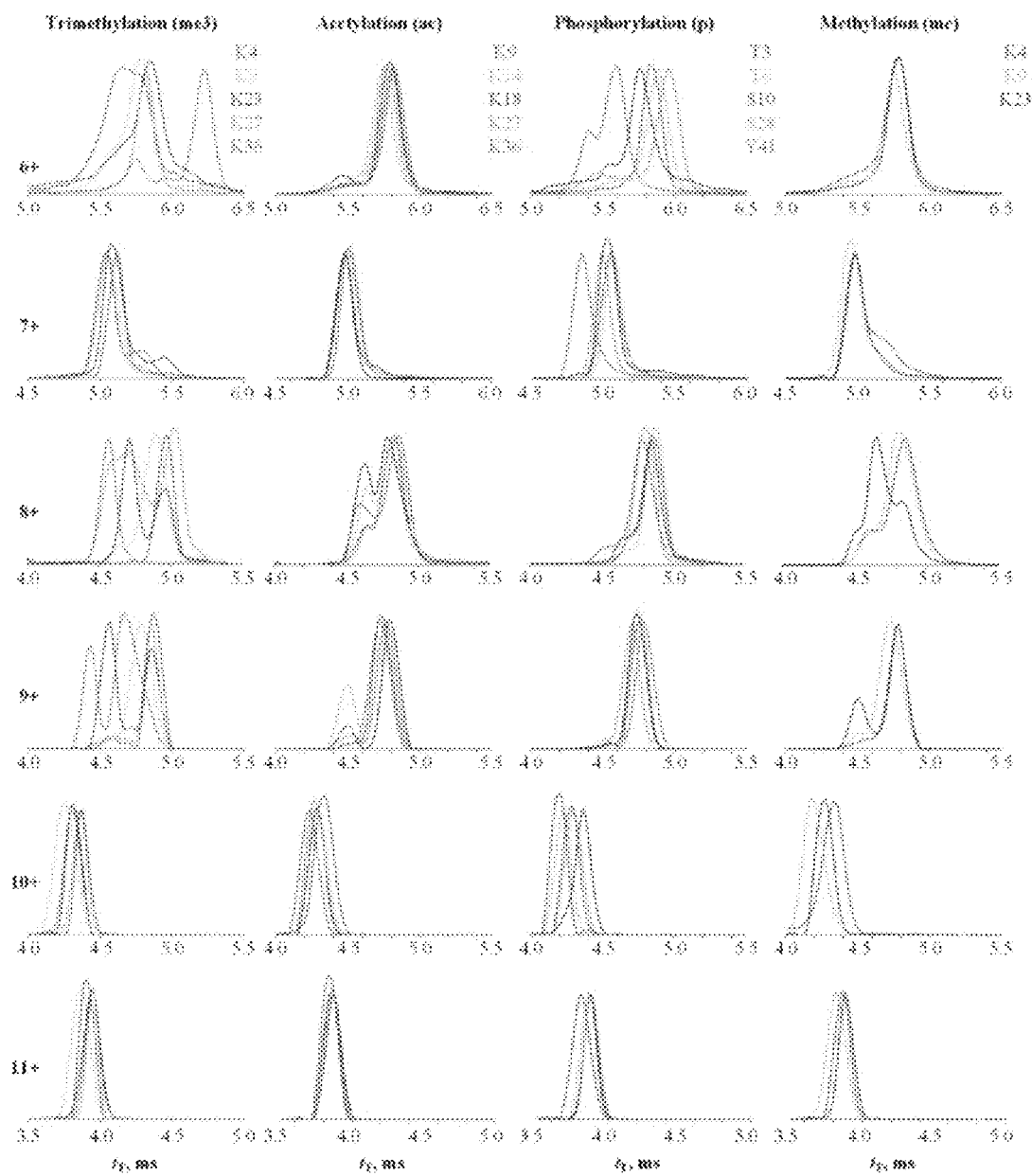
FIG. 16 shows TWIMS analysis of histone tail variants: spectra for z=6-11 measured in $N_2$ with solvent (i) using s=650 m/s.
Figure 17:
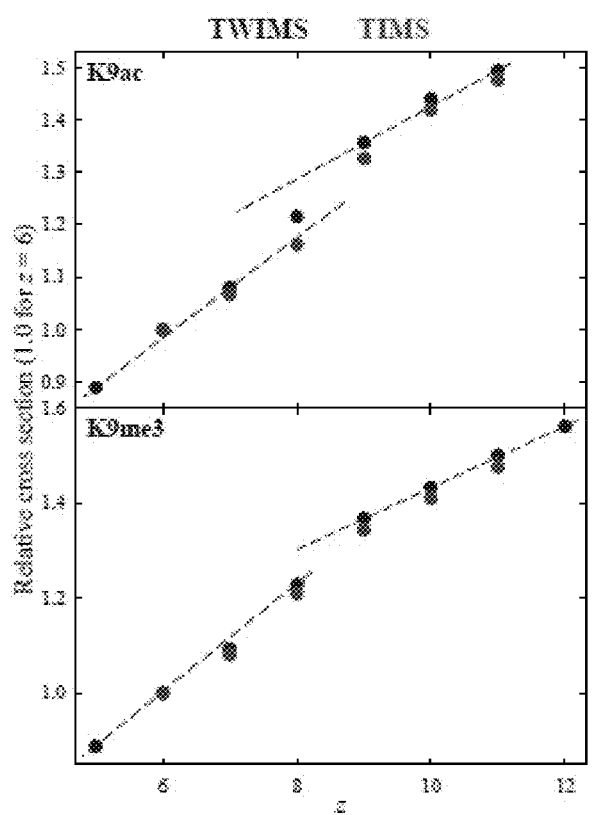
FIG. 17 shows Relative (approximate) cross sections for exemplary variants from FIG. 23 (dominant peaks). Dashed lines guide the eye through trends for charge states below and above the transition region.

Most IMS spectra were obtained using the default s=650 m/s (FIG. 16). Each variant exhibits one defined peak in z=10 and 11, but up to three (fully or partly resolved) ones in z=6-9. This suggests stepwise transition from compact conformers at low z to unfolded ones at high z over several intermediate charge states exhibiting rich structural heterogeneity, ubiquitous for proteins. As the scaling of $t_T$ as ~Ω$^2$ renders Ω about proportional to $z(t_T)^{1/2}$ over the practical $t_T$ range, relative Ω was estimated with no scale anchoring (FIG. 17). The S-shape of these plots with a jump between two trend lines for all variants confirms unfolding at intermediate states. The apparent R is 29-33 for all PTMs (average over variants and charge states) and 30-34 in z=7 and 9-11 (average over variants and PTMs). In z=8, the slightly wider peaks and lower R=27 likely reflect unresolved conformers broadening the peaks in unfolding region. Hence the performance is consistent across PTMs, their locations, and charge states.

The spectra for variants in many charge states significantly differ, but rarely enough for satisfactory resolution. The greatest separation is for me3 tails, proven using the mixtures of two-five variants (FIGS. 18A-18D). The best resolution is in z=6, 8, 9: at the peak apexes, the K23me3 is largely resolved from all but K27me3 as 8+ ions and all but K36me3 as 9+, K27me3 is largely resolved from all but K23me3 or K36me3 as 8+, and K36me3 is baseline-resolved from others as 6+ and 9+. The K9me3 is filtered from others in z=10 and 11 (not at the apex). As MS/MS can fully characterize binary variant mixtures, this partial resolution helps more than may seem: e.g., one can use 10+ or 11+ to detect and reasonably quantify K9me3, 8+ for K27me3 (in K27me3/K36me3 mix), and 9+ for K23me3 (in K23me3/K36me3 mix), while the K4me3 and K36me3 variants with PTMs on bookend sites need no separation. This strategy demands no prior knowledge of the IMS spectra for each variant, although that would accelerate analyses by revealing the optimum drift times and charge states. As such, me3 histones were separated.

Figures 18A, 18B, 18C:
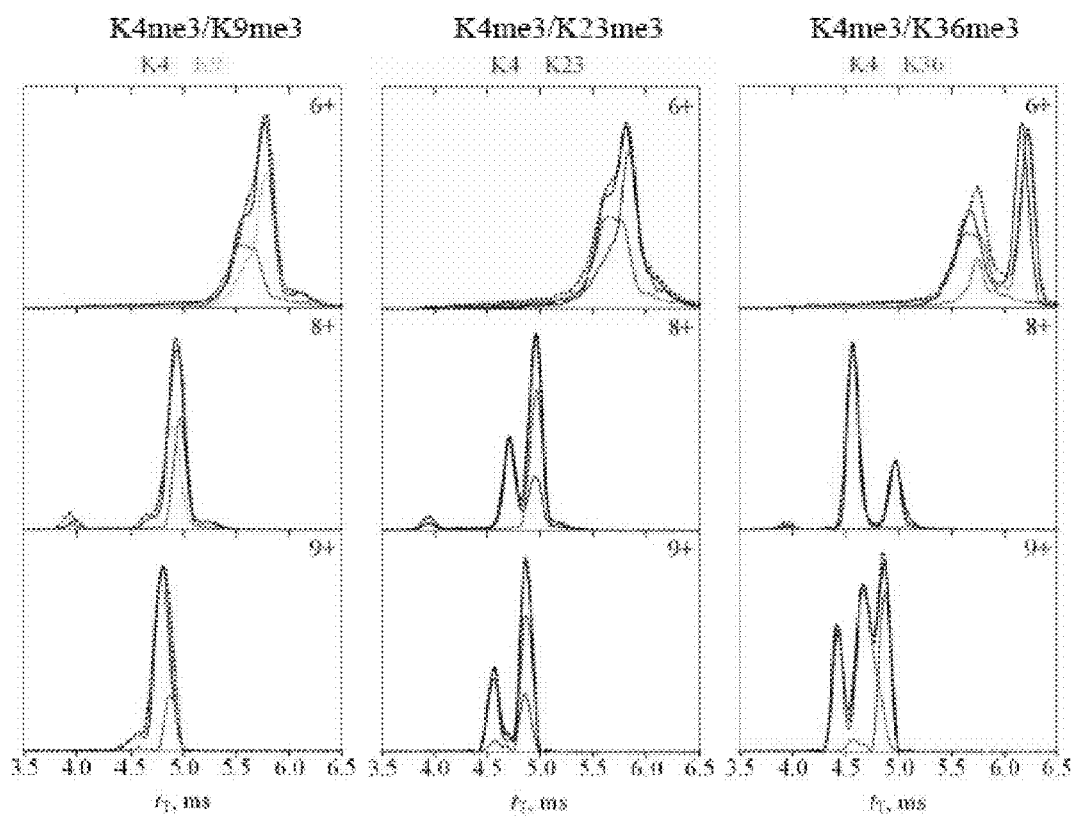
FIGS. 18A-18F show TWIMS spectra for selected mixtures of me3, p, and me variants measured in $N_2$ using solvent (i) (solid black lines) with fits by scaled individual traces from FIG. 16 (colored lines) and their computed additions (dotted lines).
Figures 18D, 18E, 18F:
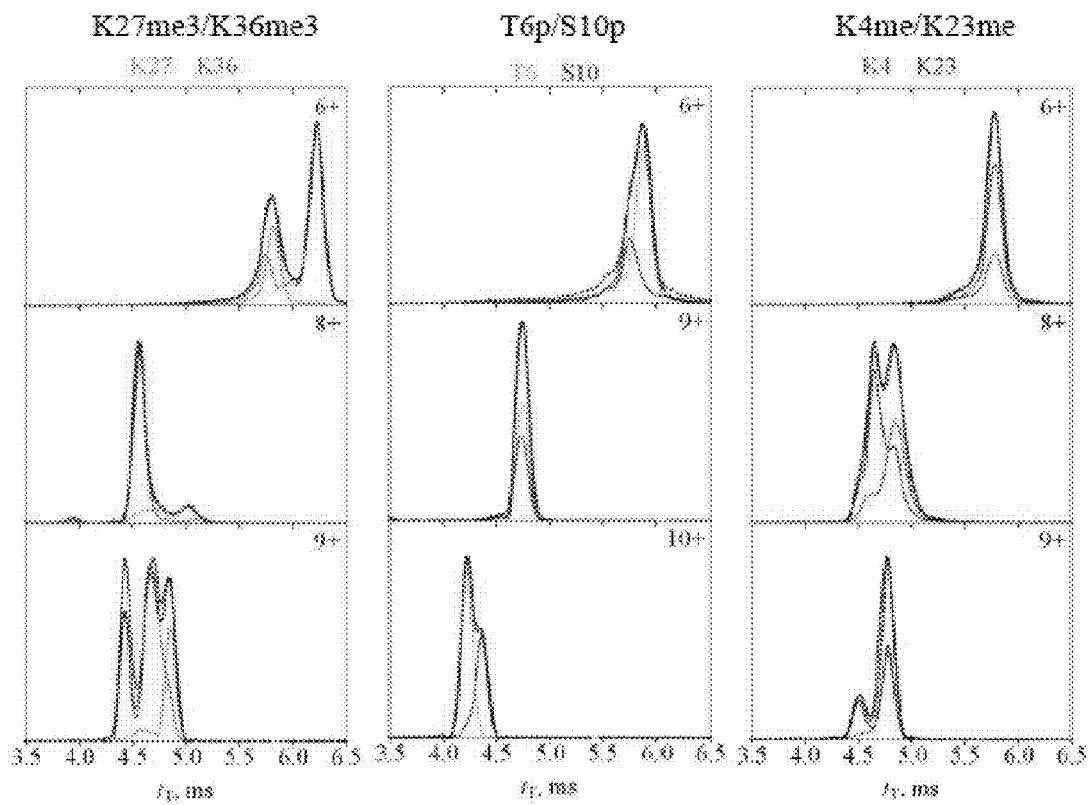

For isobaric acetylation, no variant is fully resolved in any state. The K9ac and K36ac are filtered in 10+ at the longest and shortest $t_T$ respectively (with large signal loss), but separating those "bookend" variants is not crucial. The K14ac is enriched at the lesser peak in 9+, but intense contamination by other variants makes that of little utility. The situation for phosphorylation is more promising. One can cleanly filter the Y41p variant at its peak apex in 7+ and T3p and S10p (away from apexes) in respectively 11+ and 10+, and T6p/S28p mix near the apex of S28p in 6+ (the S10p contribution there would not compromise the analysis for T6p and S28p with occupied external sites). For single methylation with just three variants here, the major task is separating K9me with PTM in the middle. That is feasible (a bit off apex) in 10+ and 11+, and the K4me variant can be filtered (away from the apex) in 10+. The profile for K23me differs from those for K4me and K9me in 8+ and 9+ substantially, but not enough for clean filtering. The separations for p and me variants are also verified using selected mixtures (FIGS. 18E-18F).

Figure 19:
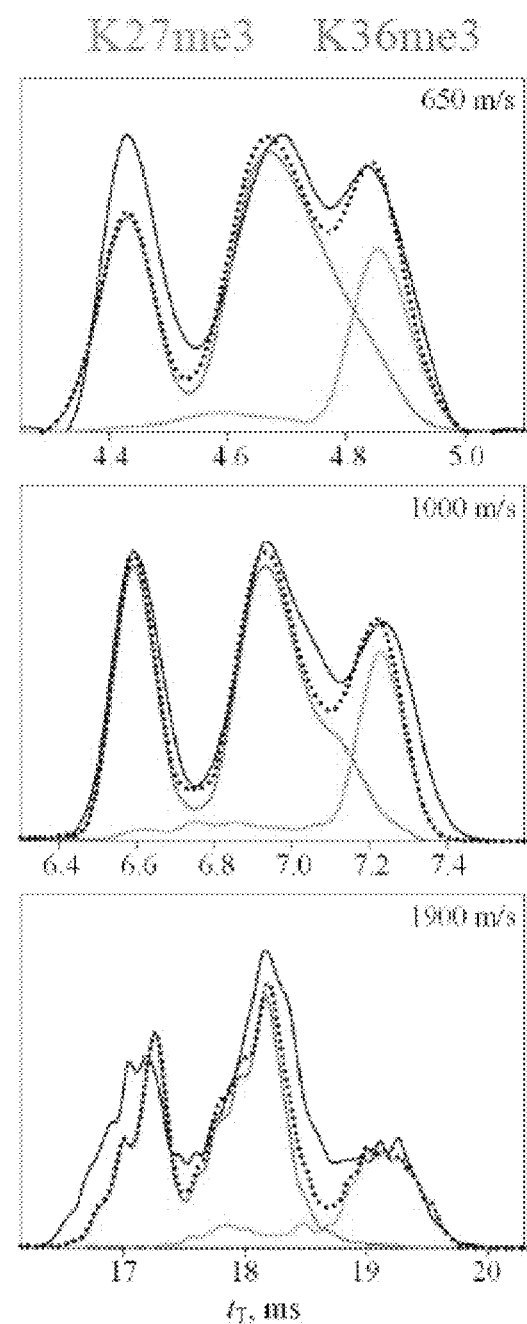
FIG. 19 shows TWIMS spectra for K27me3/K36me3 mix (z=9) measured in $N_2$ with solvent (i) depending on the waveform speed (solid black lines), with fits by scaled individual traces from FIG. 16 (colored lines) and their computed sum (dotted lines). Data for selected other mixtures are in FIG. 20.
Figure 20A:
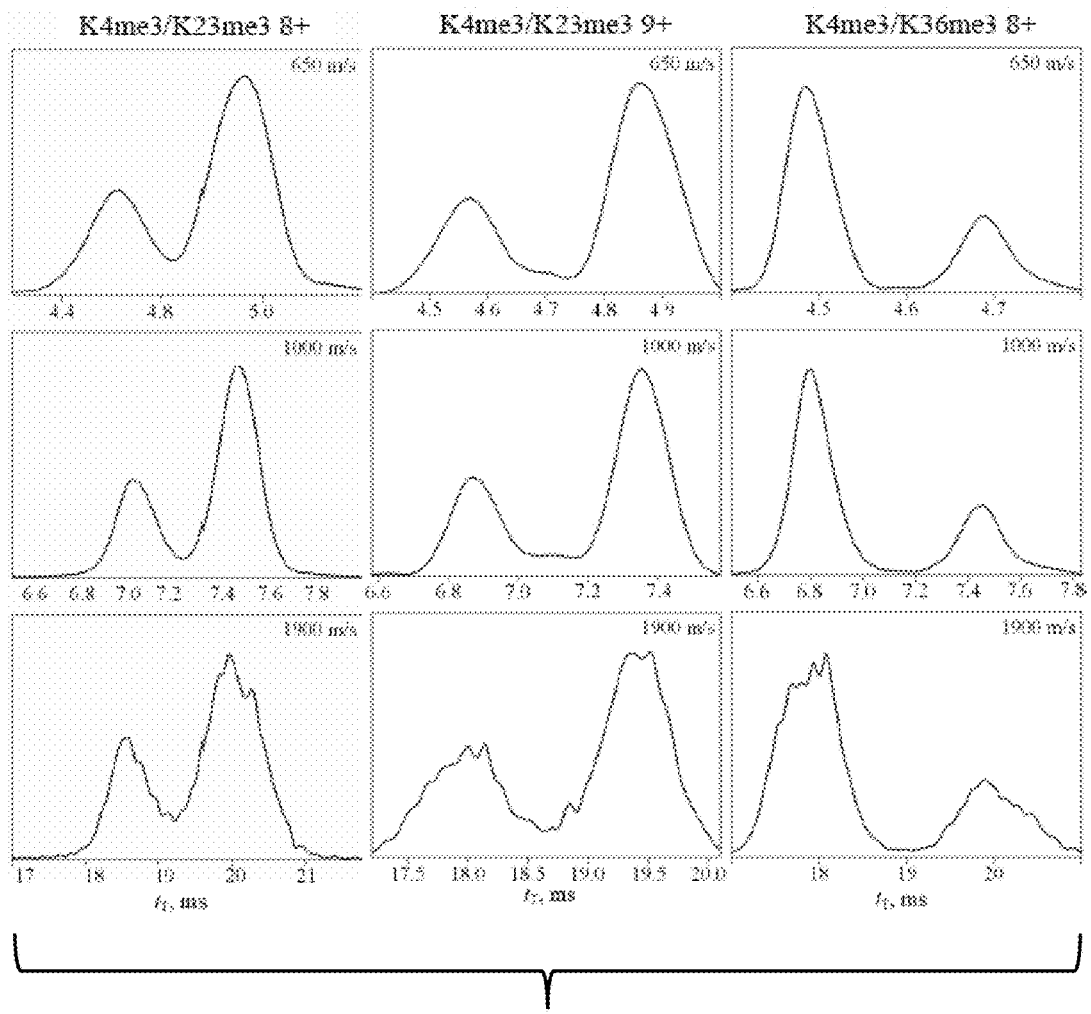
FIGS. 20A-20B show TWIMS spectra for selected variant mixtures measured in $N_2$ with solvent (i) using the traveling wave speeds of 650, 1000, and 1900 m/s.
Figure 20B:
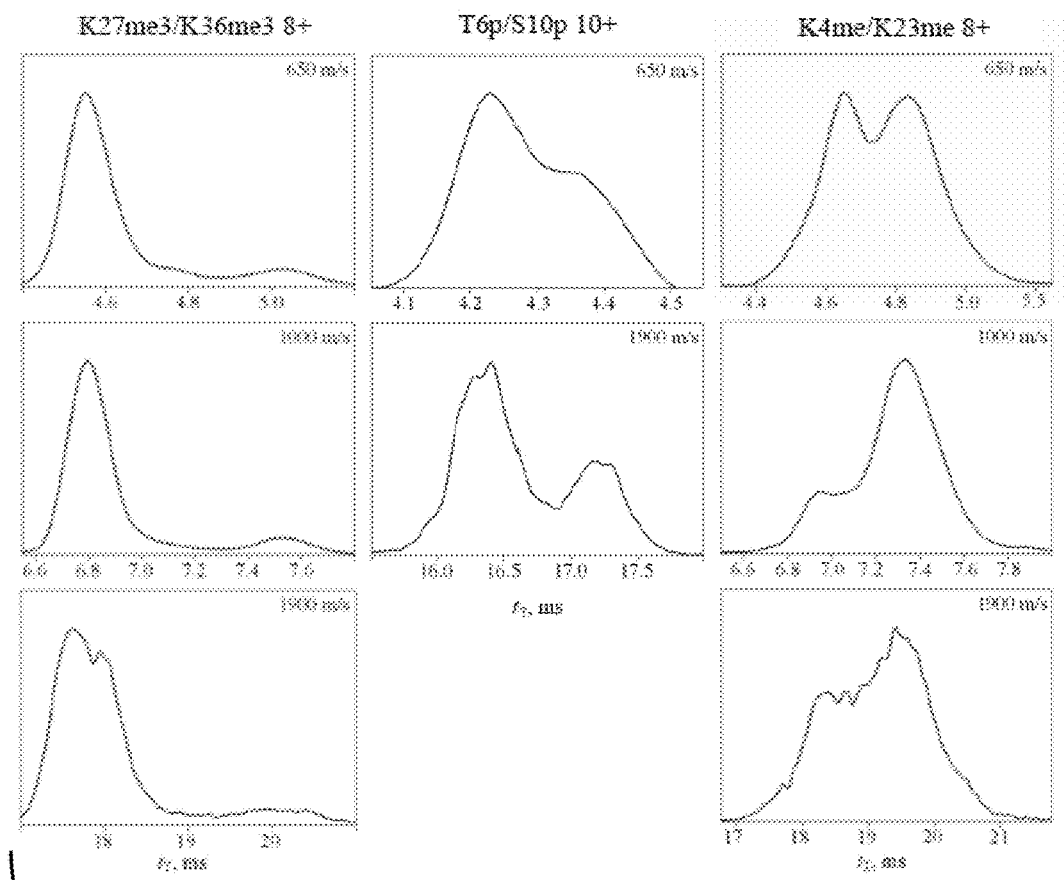
Figure 21:
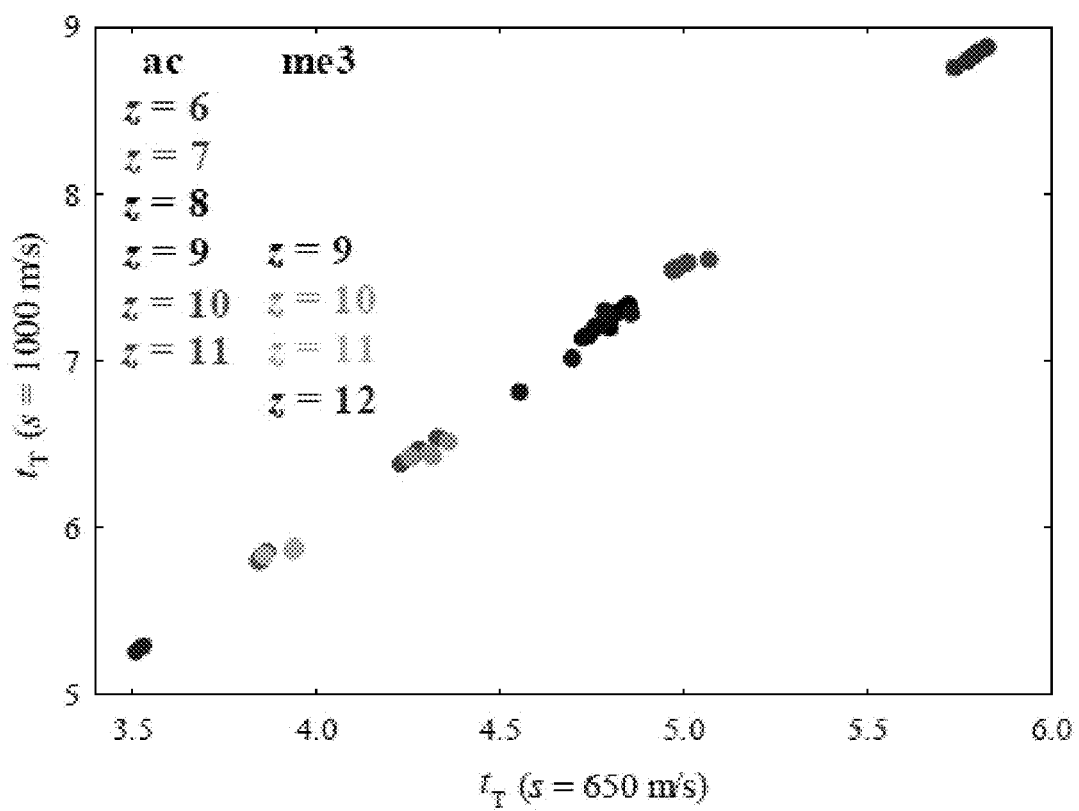
FIG. 21 shows pairwise linear correlations between transit times for ac and me3 variants at the traveling wave speeds of 650 and 1000 m/s. Variants with only three data points and p variants with partial data at s=1000 m/s are not included.

The peak pattern in FIG. 16 is consistent over the practical wave speed range: raising s from 650 to 1000 and 1900 m/s increases $t_T$ from 4-7 to 6-10 and 10-25 ms without significantly moving the relative peak positions (FIGS. 19 and 20A-20B). Quantitatively, the $t_T$ sets at s of 650 and 1000 m/s are correlated with r$^2$ (average over all charge states) of 0.95 for ac and 0.85 for me3 where the transitions between major conformers at some z interfere with correlation (FIG. 21). The respective values for pairs at s=1000 and 1900 m/s decrease to still high 0.90 and 0.79 (excluding a single outlier). Hence the ion geometries are largely conserved between ~5 and ~20 ms. The resolving power is unchanged at s=1000 m/s (apparent R of 29-35 in z=7 and 9-11 and R=25 in z=8 upon averaging over all me3 and ac variants), but drops at s=1900 m/s (to R=17-28 in z=7 and 9-11 and R=14 in z=8). Thus the variant resolution at s=1000 m/s is close to that at s=650 m/s, but deteriorates at s=1900 m/s outside the optimum range.

Figure 22A:
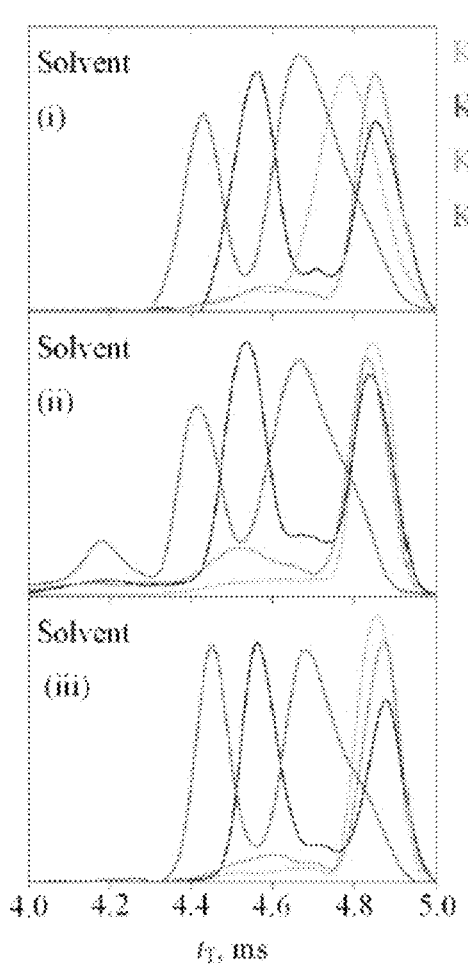
FIGS. 22A-22B show TWIMS spectra measured with different ESI solvents: (A) four me3 variants (z=9) with solvents (i, ii, iii), (B) K23me3 (z=8 and 9) with solvents (i, iv).
Figure 22B:
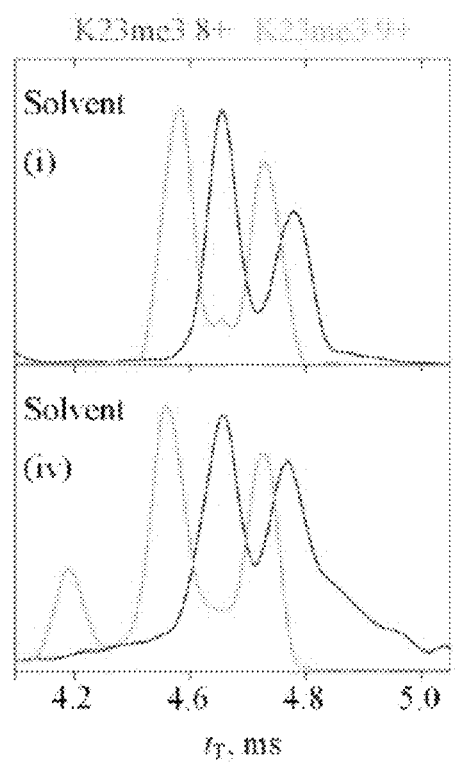
Figure 23:
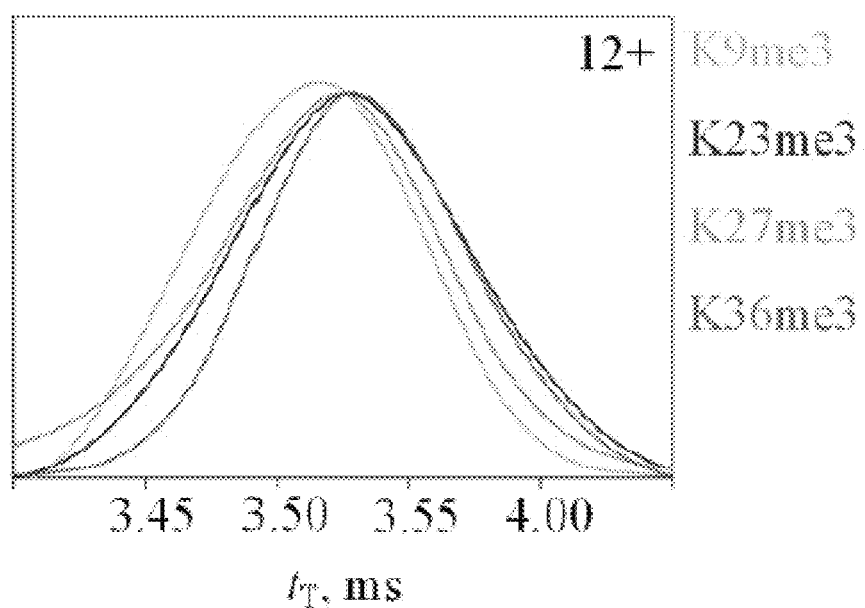
FIG. 23 shows TWIMS spectra for me3 variants in z=12 measured in $N_2$ using solvent (ii) and s=650 m/s.

Substitution of ESI solvent has minor effects on IMS spectra in any given charge state (FIGS. 22A-22B). This agrees with the analyses of unmodified histone tails using Synapt G2, where the mobilities at fixed z were same with solvent pH of 2 and 6.5. More acidic or organic media favor higher z as anticipated, and solvents (ii) and (iii) produced me3 variants in z=12 observed in FAIMS. However, no significant variant resolution for 12+ ions was observed (FIG. 23).

Hence the variant separations by ESI-TWIMS are independent of the source and kinetic factors, likely reflecting the equilibrium ion geometries formed in the desolvation region. Then overcoming the generally insufficient variant resolution requires instruments with higher IMS resolving power, such as TIMS.

TIMS Separations of Proteoforms

Figure 24:
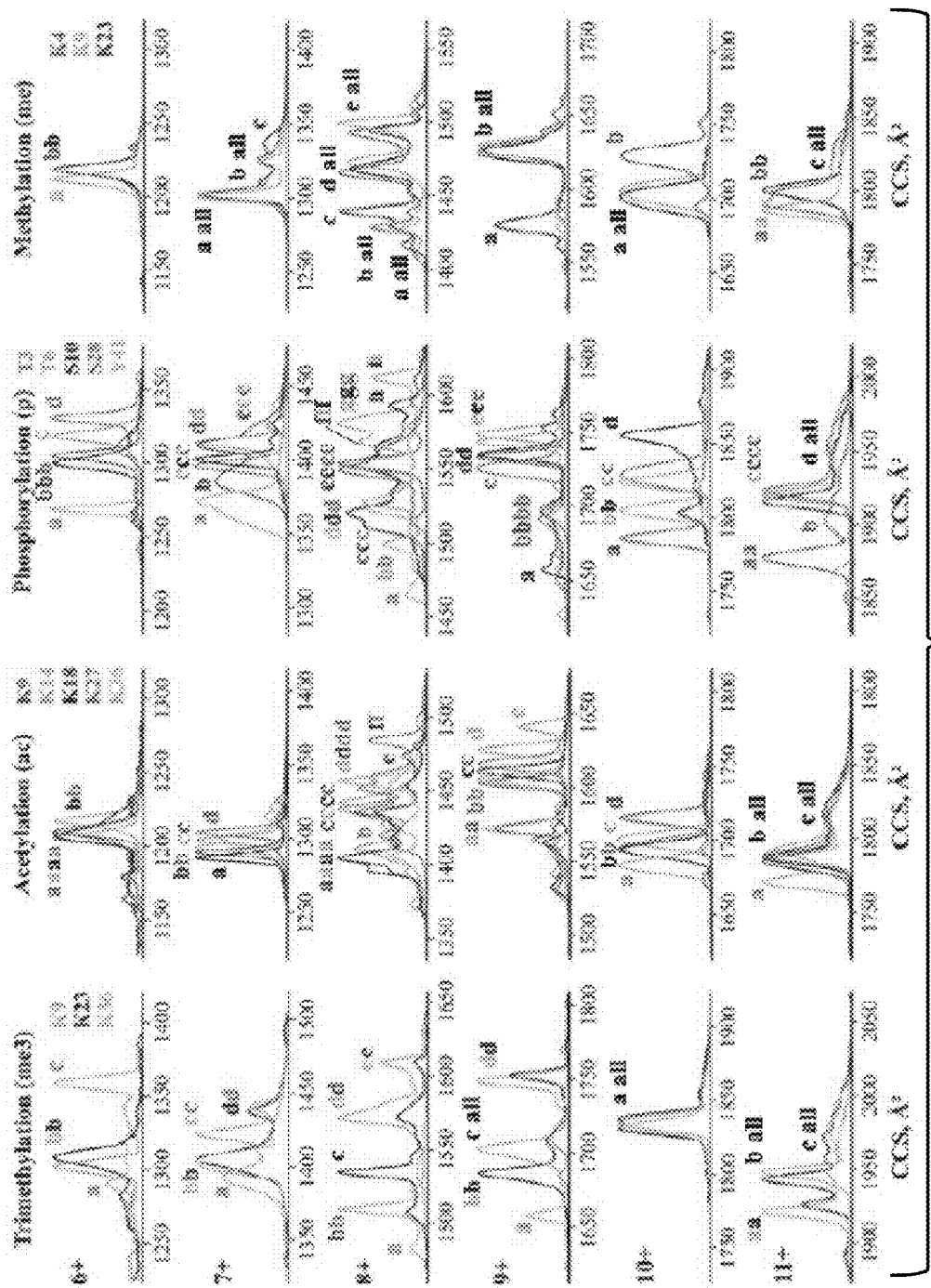
FIG. 24 shows TIMS analysis of histone tail variants: spectra for z=6-11 (with MeOH/$H_2O$ solution, $t_{ramp}$=500 ms, cross section scale), with substantial features labeled.
Figure 25A:
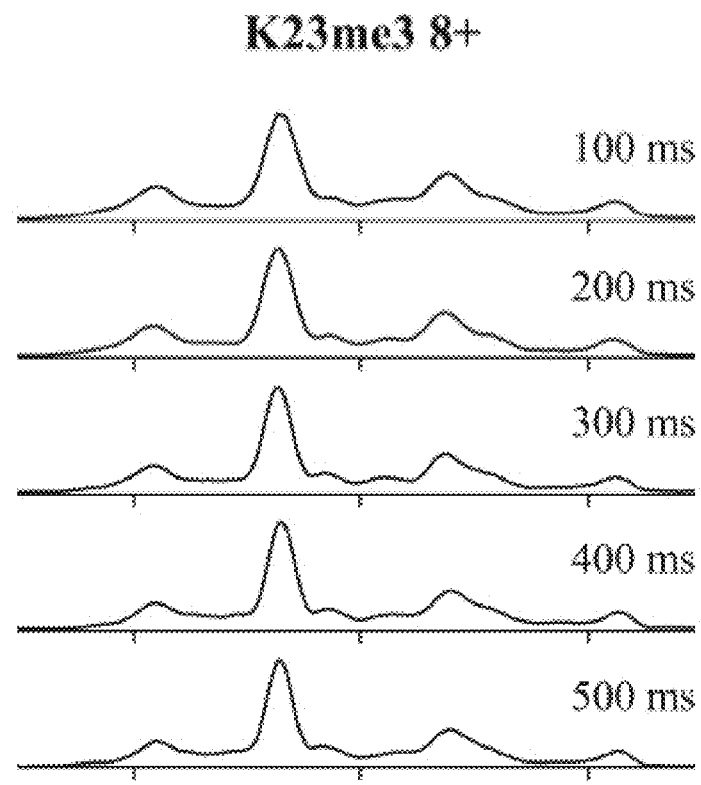
FIGS. 25A-25B show TIMS spectra (cross section scale) for K23me3 8+ measured at (A) $t_{ramp}$=100-500 ms from the MeOH/$H_2O$ solution and (B) $t_{ramp}$=500 ms from that and aqueous solutions. Results for some other variants and charge states are in FIG. 26.
Figure 25B:
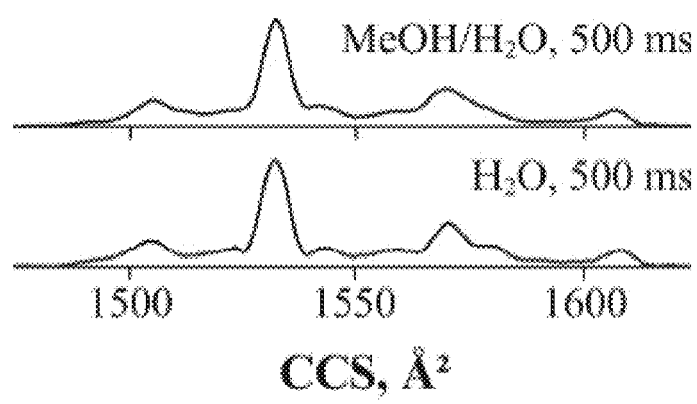
Figure 26A:
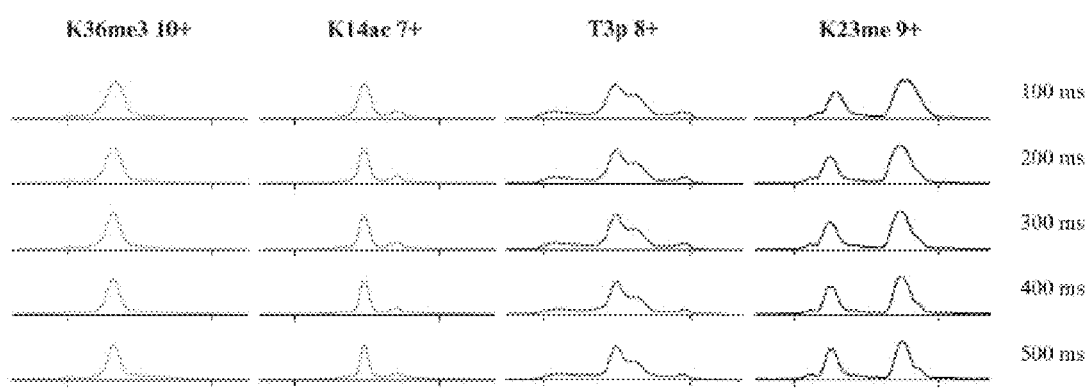
FIGS. 26A-26B show TIMS spectra (on the cross section scale) measured at: (A) $t_{ramp}$=100-500 ms for K36me3 (z=10), K14ac (z=7), pT3 (z=8) and K23me (z=9), (B) $t_{ramp}$=500 ms for K36me3 (z=10), K14ac (z=7), pT3 (z=8) and K23me (z=9) from MeOH and aqueous solutions.
Figure 26B:
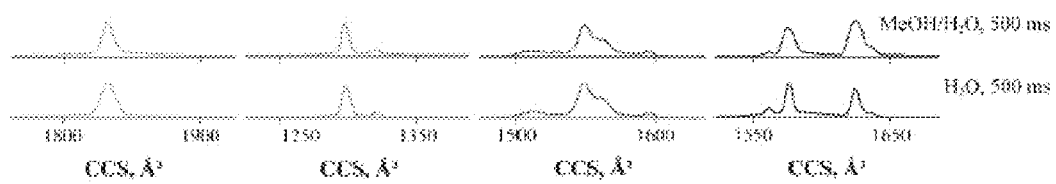

In TIMS analyses, z=6-11 were observed for all PTMs (K4me3 and K27me3 were not studied because of sample shortage). The resolving power for base peaks at Sr=0.3 V/ms is ~80-280, with mean (over variants and charge states) of ~150-170 for each PTM. The overall average (R=167) is >5× that with TWIMS (R=32), yielding multiple (up to ~10) substantial peaks for all variants in each z except 6 and 10 (FIG. 24, Table 10). These R metrics match the averages for multiply-charged unmodified peptides. No drop of R in z=8: instead of peak broadening, multiple conformers produce rich spectra for all variants. The cross sections increase at higher z due to unfolding, and relative $\Omega$ match those estimated from TWIMS data (FIG. 17). This validates the approximation to obtain the relative $\Omega$ from raw TWIMS spectra and points to similar ion geometries in the two separations.

TABLE 10

Collision cross sections (CCS, Å$^2$) and resolving power (R) values for protonated histone tails measured using TIMS.

| Peptide | Ion | CCS (Å$^2$), std. error of mean: ±0.04% | R |
|---|---|---|---|
| K9me3 | [M + 6H]$^{6+}$ | 1303 | 137 |
| | [M + 7H]$^{7+}$ | 1398/1406 | 203/180 |
| | [M + 8H]$^{8+}$ | 1574/1607 | 96/102 |
| | [M + 9H]$^{9+}$ | 1685/1710/1735/1749 | 153/119/141/211 |
| | [M + 10H]$^{10+}$ | 1835 | 170 |
| | [M + 11H]$^{11+}$ | 1921 | 201 |
| K23me3 | [M + 6H]$^{6+}$ | 1308 | 92 |
| | [M + 7H]$^{7+}$ | 1405/1437 | 82/72 |
| | [M + 8H]$^{8+}$ | 1508/1535/1574/1609 | 188/284/146/223 |
| | [M + 9H]$^{9+}$ | 1684/1707/1751 | 167/76/233 |
| | [M + 10H]$^{10+}$ | 1830/1839 | 218/236 |
| | [M + 11H]$^{11+}$ | 1926/1943 | 244/183 |
| K36me3 | [M + 6H]$^{6+}$ | 1291/1357 | 128/137 |
| | [M + 7H]$^{7+}$ | 1394/1422/1441 | 59/133/119 |
| | [M + 8H]$^{8+}$ | 1483/1510 | 215/265 |
| | [M + 9H]$^{9+}$ | 1658/1702 | 240/122 |
| | [M + 10H]$^{10+}$ | 1833 | 176 |
| | [M + 11H]$^{11+}$ | 1948 | 229 |
| K9ac | [M + 6H]$^{6+}$ | 1209 | 105 |
| | [M + 7H]$^{7+}$ | 1290 | 145 |
| | [M + 8H]$^{8+}$ | 1395/1404/1420/1435/1447/1473 | 199/187/202/144/90/184 |
| | [M + 9H]$^{9+}$ | 1529/1563/1572/1603 | 191/223/197/255 |
| | [M + 10H]$^{10+}$ | 1673/1694/1715 | 222/121/159 |
| | [M + 11H]$^{11+}$ | 1784 | 133 |
| K14ac | [M + 6H]$^{6+}$ | 1205 | 120 |
| | [M + 7H]$^{7+}$ | 1298/1322 | 137/85 |
| | [M + 8H]$^{8+}$ | 1404/1411/1427/1434/1442/1451 | 134/168/153/163/170/45 |
| | [M + 9H]$^{9+}$ | 1541/1562/1572/1587/1625/1640 | 220/112/210/122/216/262 |
| | [M + 10H]$^{10+}$ | 1701 | 150 |
| | [M + 11H]$^{11+}$ | 1785/1814 | 223/151 |
| K18ac | [M + 6H]$^{6+}$ | 1207 | 72 |
| | [M + 7H]$^{7+}$ | 1287/1310 | 239/218 |
| | [M + 8H]$^{8+}$ | 1396/1405/1418/1428/1435/1454/1480 | 208/156/153/111/197/117/159 |
| | [M + 9H]$^{9+}$ | 1531/1563/1579/1611 | 247/223/198/201 |
| | [M + 10H]$^{10+}$ | 1694 | 179 |
| | [M + 11H]$^{11+}$ | 1786 | 192 |
| K27ac | [M + 6H]$^{6+}$ | 1210 | 145 |
| | [M + 7H]$^{7+}$ | 1294/1304/1326 | 223/215/221 |
| | [M + 8H]$^{8+}$ | 1412/1420/1438/1452/1459/1484/1498 | 157/144/150/190/131/206/156 |
| | [M + 9H]$^{9+}$ | 1558/1572/1616 | 180/194/171 |
| | [M + 10H]$^{10+}$ | 1695 | 131 |
| | [M + 11H]$^{11+}$ | 1789 | 145 |
| K36ac | [M + 6H]$^{6+}$ | 1217 | 124 |
| | [M + 7H]$^{7+}$ | 1294/1301/1315 | 193/239/198 |
| | [M + 8H]$^{8+}$ | 1373/1396/1406/1425/1444/1456/1475 | 177/47/201/88/79/209/88 |
| | [M + 9H]$^{9+}$ | 1526/1555/1575/1605/1621 | 209/216/108/189/80 |
| | [M + 10H]$^{10+}$ | 1683 | 155 |
| | [M + 11H]$^{11+}$ | 1770/1792 | 197/201 |
| T3p | [M + 6H]$^{6+}$ | 1305 | 161 |
| | [M + 7H]$^{7+}$ | 1386/1412 | 75/150 |
| | [M + 8H]$^{8+}$ | 1556/1571/1596 | 134/118/114 |
| | [M + 9H]$^{9+}$ | 1653/1691/1734 | 221/72/73 |
| | [M + 10H]$^{10+}$ | 1786 | 194 |
| | [M + 11H]$^{11+}$ | 1878 | 146 |
| T6p | [M + 6H]$^{6+}$ | 1319 | 134 |
| | [M + 7H]$^{7+}$ | 1412 | 159 |
| | [M + 8H]$^{8+}$ | 1500/1523/1532/1568/1581/1612 | 70/206/174/204/144/269 |
| | [M + 9H]$^{9+}$ | 1669/1714/1749 | 121/163/192 |
| | [M + 10H]$^{10+}$ | 1805 | 160 |
| | [M + 11H]$^{11+}$ | 1921 | 209 |
| S10p | [M + 6H]$^{6+}$ | 1300 | 122 |
| | [M + 7H]$^{7}$ | 1401/1414/1425 | 246/267/285 |
| | [M + 8H]$^{8+}$ | 1511/1520/1534/1553/1565/1582/1593/1611 | 232/179/197/219/142/115/306/298 |
| | [M + 9H]$^{9+}$ | 1665/1706/1736/1753/1767 | 86/74/235/428/89 |
| | [M + 10H]$^{10+}$ | 1783/1800/1852 | 244/243/197 |
| | [M + 11H]$^{11+}$ | 1917 | 167 |
| S28p | [M + 6H]$^{6+}$ | 1307/1327 | 82/140 |
| | [M + 7H]$^{7+}$ | 1380/1396/1423 | 88/170/169 |
| | [M + 8H]$^{8+}$ | 1515/1554/1579 | 205/187/106 |
| | [M + 9H]$^{9+}$ | 1695/1726 | 138/149 |
| | [M + 10H]$^{10+}$ | 1829 | 116 |
| | [M + 11H]$^{11+}$ | 1924 | 163 |
| Y41p | [M + 6H]$^{6+}$ | 1270 | 155 |
| | [M + 7H]$^{7+}$ | 1362/1379 | 91/136 |
| | [M + 8H]$^{8+}$ | 1464/1499/1529/1553 | 229/259/118/174 |
| | [M + 9H]$^{9+}$ | 1627/1691/1659/1744 | 258/148/210/208 |
| | [M + 10H]$^{10+}$ | 1824 | 182 |
| | [M + 11H]$^{11+}$ | 1922/1869 | 180/228 |
| K4me | [M + 6H]$^{6+}$ | 1218 | 129 |
| | [M + 7H]$^{7+}$ | 1303/1315/1326 | 200/146/199 |
| | [M + 8H]$^{8+}$ | 1414/1428/1439/1452/1465/1493/1506/1517 | 89/291/175/278/144/138/232/124 |
| | [M + 9H]$^{9+}$ | 1627/1638/1651 | 148/252/229 |
| | [M + 10H]$^{10+}$ | 1695/1730/1750 | 213/122/221 |
| | [M + 11H]$^{11+}$ | 1791/1799 | 167/189 |
| K9me | [M + 6H]$^{6+}$ | 1212 | 135 |
| | [M + 7H]$^{7+}$ | 1301/1324 | 190/221 |
| | [M + 8H]$^{8+}$ | 1426/1438/1473/1499/1511 | 247/173/142/180/140 |
| | [M + 9H]$^{9+}$ | 1574/1591/1628/1640 | 237/175/119/149 |
| | [M + 10H]$^{10+}$ | 1704 | 97 |
| | [M + 11H]$^{11+}$ | 1787 | 167 |
| K23me | [M + 6H]$^{6+}$ | 1218 | 151 |
| | [M + 7H]$^{7+}$ | 1302/1309/1326/1336 | 193/73/165/69 |
| | [M + 8H]$^{8+}$ | 1416/1430/1439/1453/1468/1494/1507 | 153/164/212/153/120/199/260 |
| | [M + 9H]$^{9+}$ | 1561/1576/1625/1635 | 244/146/140/178 |
| | [M + 10H]$^{10+}$ | 1700 | 90 |
| | [M + 11H]$^{11+}$ | 1800 | 143 |

With ions accumulated for 10 ms before the ramp, our $t_{ramp}$=100-500 ms means total residence time of ~50-300 ms. Hence even the shortest time in TIMS is much beyond the longest in TWIMS. Gas-phase protein conformations may evolve over time, specifically on the ~10-500 ms scale relevant here. Present TIMS experiments employed "soft" ion injection without activation. However, the IMS spectra for all variants and charge states do not significantly depend on $t_{ramp}$ (FIG. 5a, S7a). The spectra from MeOH/H$_2$O and H$_2$O solutions are also close (FIG. 5b, S7b). Perhaps field heating of ions in the source and/or TIMS cell anneals these peptides to equilibrium conformers prior to ~50 ms, which would be easier for histone tails compared to larger intact proteins. With that, the spectra obtained at maximum resolution ($t_{ramp}$=500 ms) using MeOH/H$_2$O solutions that provide a higher and more stable ion signal were studied.

Figure 27:
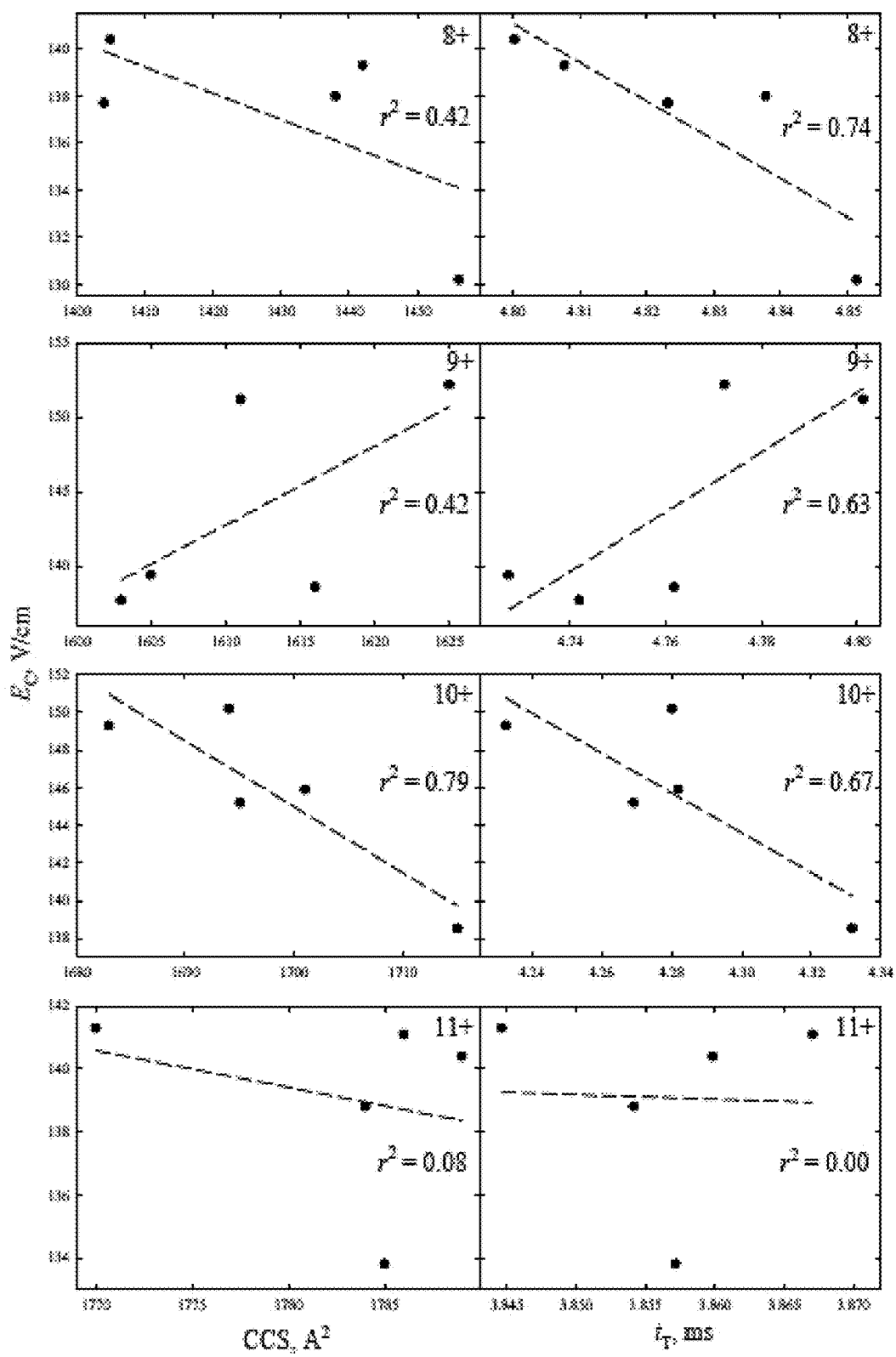
FIG. 27 shows linear correlations between differential or field asymmetric waveform ion mobility spectrometry (FAIMS) and TIMS (left) or TWIMS (right) separations with $r^2$ marked, for ac variants. The plots for p variants are in FIG. 38.

The three me3 variants can be largely separated using z=6-9 and 11 (FIG. 24). One can filter K36me3 from K9me3 and K23me3 best at the major peak c in 6+ and lesser a in 9+, largely K23me3 from others at the major peaks c in 8+ and b in 9+, and readily K9me3 from K36me3 in z=6, 8, 9, 11. Resolving K9me3 from K23me3 is difficult: the best outcome is a ~3× enhancement in 8+ at the major peak d or e. However, separation to the binary mixtures (by resolving the K9me3/K23me3 mix and K36me3) is trivial. As seen in DTIMS and FAIMS analyses, the spectra are "quantized": most variants exhibit features at discrete $\Omega$ bands (letter labels in FIG. 27) in different proportions. This suggests a set of energetically competitive folds persisting across variants, with relative energies and thus populations dependent on the PTM position.

Despite many more features, these separations track the order and often the relative spread of cross sections found in TWIMS (FIG. 16): K9me3≤K23me3<K36me3 in 6+, similar $\Omega$ for leftmost peaks with features c, d for K36me3 and (with higher 0) d for K23me3 in 7+, K36me3<K23me3<K9me3 for major peaks in 8+, and K9me3<K23me3≤K36me3 for those in 11+. The starkest similarity is in 9+: here K9me3 has one major peak d with feet b and c, K23me3 has three peaks (largest b, smallest c, and medium d); K36me3 has two intense peaks (a and larger c), and the overall order is K36a<K23b~K9b<K36c≤K23c<K9d<K23d. The only difference is that in 10+ all variants coincide in FIG. 27 but K9me3 lies to the left of other two in FIG. 16.

The results for other PTMs are similar. With ac variants (FIG. 24), there is modest separation in 6+, but K9ac and K18ac are well-resolved from K14ac and K27ac (and vice versa) at the peak apexes in 7+. The blow-up of conformational multiplicity in 8+ obstructs separations, but K27ac is filtered from others at f. The 9+ state permits excellent resolution of K14ac from others at the major peak d and intense e (and vice versa at the major peaks for others a, b, c), and of K9ac at b from K14ac and K27ac. Each variant exhibits one major peak in 10+ as with me3 case, but here those are dispersed enough to resolve K9ac and K36ac from others at the apexes. In 11+, all variants are similar except K36ac filtered at the major peak a. These properties permit multiple protocols to quantify all variants in a mixture. The optimum may be to isolate K9ac in 10+, K14ac in 9+, K27ac in 8+, and K36ac in 10+ or 11+ (not truly necessary for the bookend K9ac and K36ac). The K18ac is not resolved in any state individually, but is to binary mixtures (K9ac/K18ac at the peak apex in 7+ and K18ac/K27ac right of the c apex in 9+) allowing redundant quantification by ETD. The order of peaks across charge states also correlates with TWIMS data. For example, that in 10+ is K36ac<K18ac≤K27ac<K14ac<K9ac in TIMS and similar K36ac<K27ac≤K18ac=K14ac<K9ac in TWIMS (FIG. 16).

Figure 28:
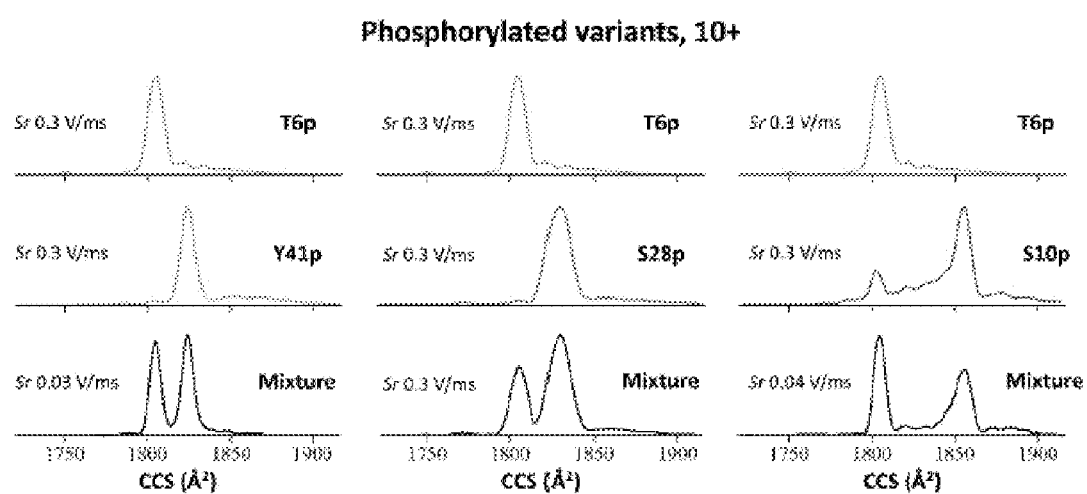
FIG. 28 shows TIMS spectra for selected mixtures of p variants and traces for the two components.

With phosphorylated variants (FIG. 24), one can pull out (at apexes) S28p and Y41p in 6+, T3p in 10+ and 11+, and S10p in 10+. As with ac variants, here one (T6p) is not cleanly resolved in any z, but filtered in T6p/S28p mix at the apex in 6+ and T6p/S10p mix at the apex in 10+ (best) and peak i in 8+. Hence all variants are quantifiable employing ETD. The correlation with TWIMS data is clear, e.g., the peak order (FIG. 16) is consistently Y41p<S10p<T3p<T6p<S28p in 6+ and T3p<T6p<Y41p<S28p<S10p in 10+. As with TWIMS, the separations projected from individual spectra were confirmed using binary mixtures (FIG. 28).

With methylated variants (FIG. 24), the spectra in z=6-8 have some differences but provide limited separation. K4me can be filtered at the major peak apex in 10+ and (less cleanly) K23me at peak a in 9+. The K9me is filtered from K4me right of the apex in z=10 and (not cleanly) from K23me on the left of major peaks in 6+ or 11+. Thus each variant can be filtered individually or as a dominant component of binary mixtures. The correlation with TWIMS data is seen from the peak order K9me<K4me<K23me in 11+ or intense peaks on the left for only K23me in 8+ and 9+ (FIG. 16).

Example 4—Enhancing Separations Using Metalation

Separation of Lasso and Branched-Cyclic Topoisomers

Despite the high resolving power of the TIMS analyzer, nESI-TIMS analysis of syanodin I does not provides a clear separation of the main conformation of the doubly protonated lasso and branched-cyclic topoisomers ($\Delta\Omega_r$~025% (1.2 Å$^2$) and r~0.4, FIG. 5C). A known alternative to increase the analytical power of IMS techniques is the use of metalation. In fact, metalated species tend to differ in conformation from their protonated analogs as the metal ions may bind to different sites and/or coordinate differently because of their chemical differences, potentially leading to effective IMS separation.

Figures 29A, 29B, 29C, 29D, 29E, 29F, 29G, 29H, 29I, 29J, 29K, 29L:
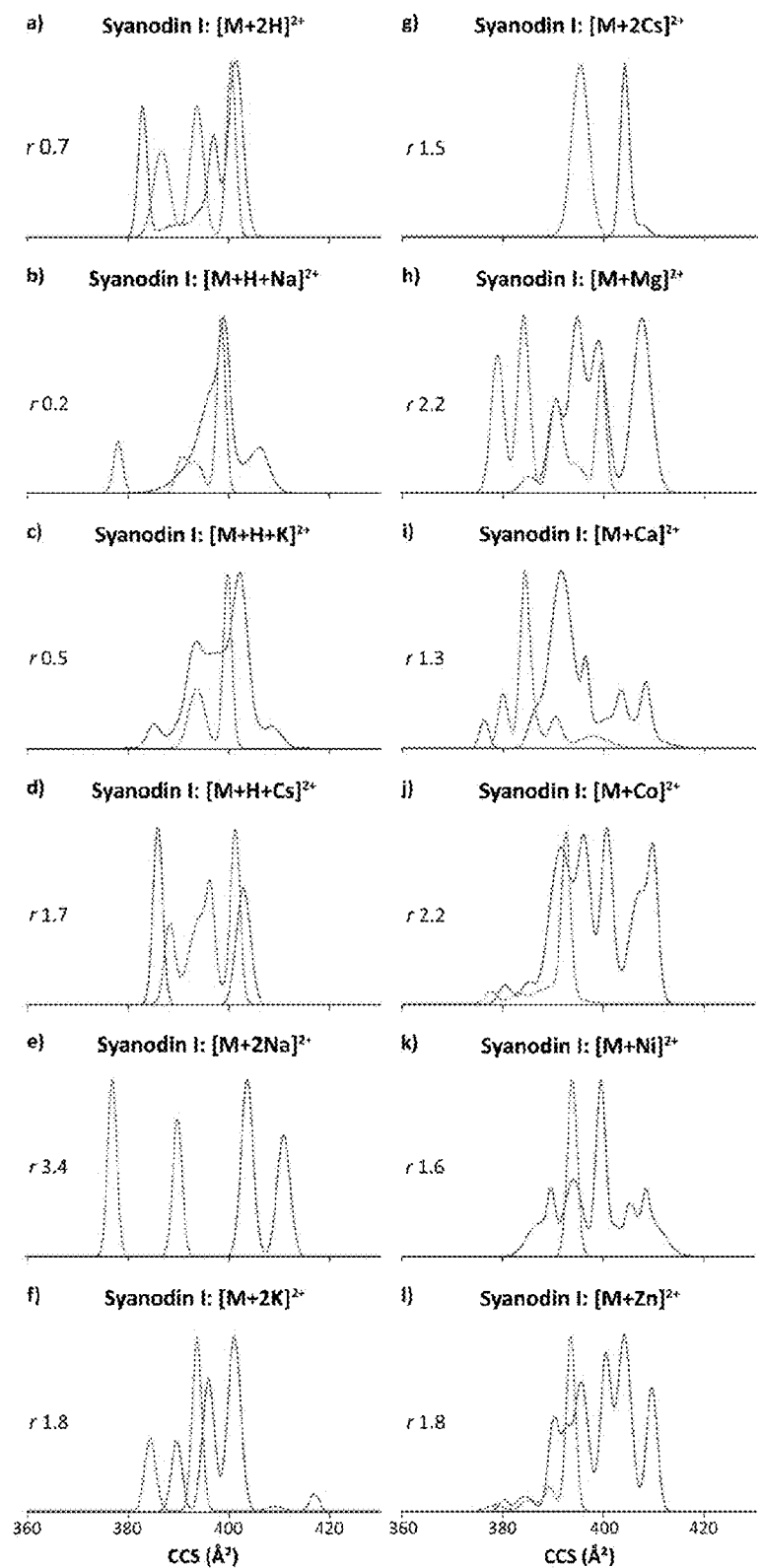
FIGS. 29A-29L show typical TIMS spectra for syanodin I (blue traces) and its branched-cyclic topoisomer (red traces) in the (A) protonated, (B, E) sodiated, (C, F) potassiated, (D, G) cesiated, (H) magnesiated, (I) calciated, (J) cobaltiated, (K) nickelated and (L) zincated form. A typical Sr of 0.56 V/ms was used and the resolution (r) values are given.
Figures 30A, 30B, 30C, 30D, 30E, 30F, 30G, 30H, 30I, 30J, 30K, 30L:
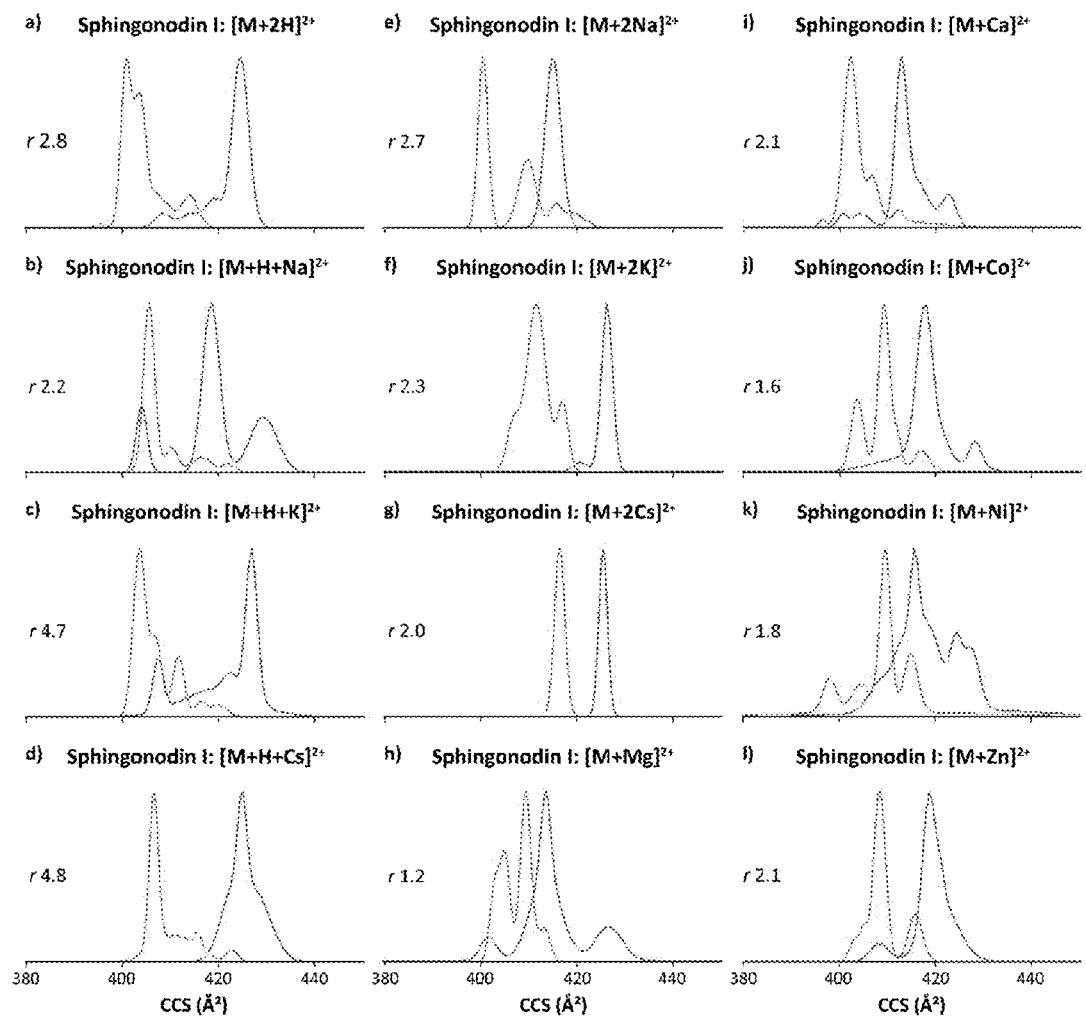
FIGS. 30A-30L show typical TIMS spectra for sphingonodin I (blue traces) and its branched-cyclic (red traces) topoisomers cationized by (A) protonated, (B, E) sodiated, (C, F) potassiated, (D, G) cesiated, (H) magnesiated, (I) calciated, (J) cobaltiated, (K) nickelated and (L) zincated species. A typical Sr of 0.56 V/ms was used and the resolution (r) values are given.
Figures 31A, 31B, 31C, 31D, 31E, 31F, 31G, 31H, 31I, 31J, 31K, 31L:
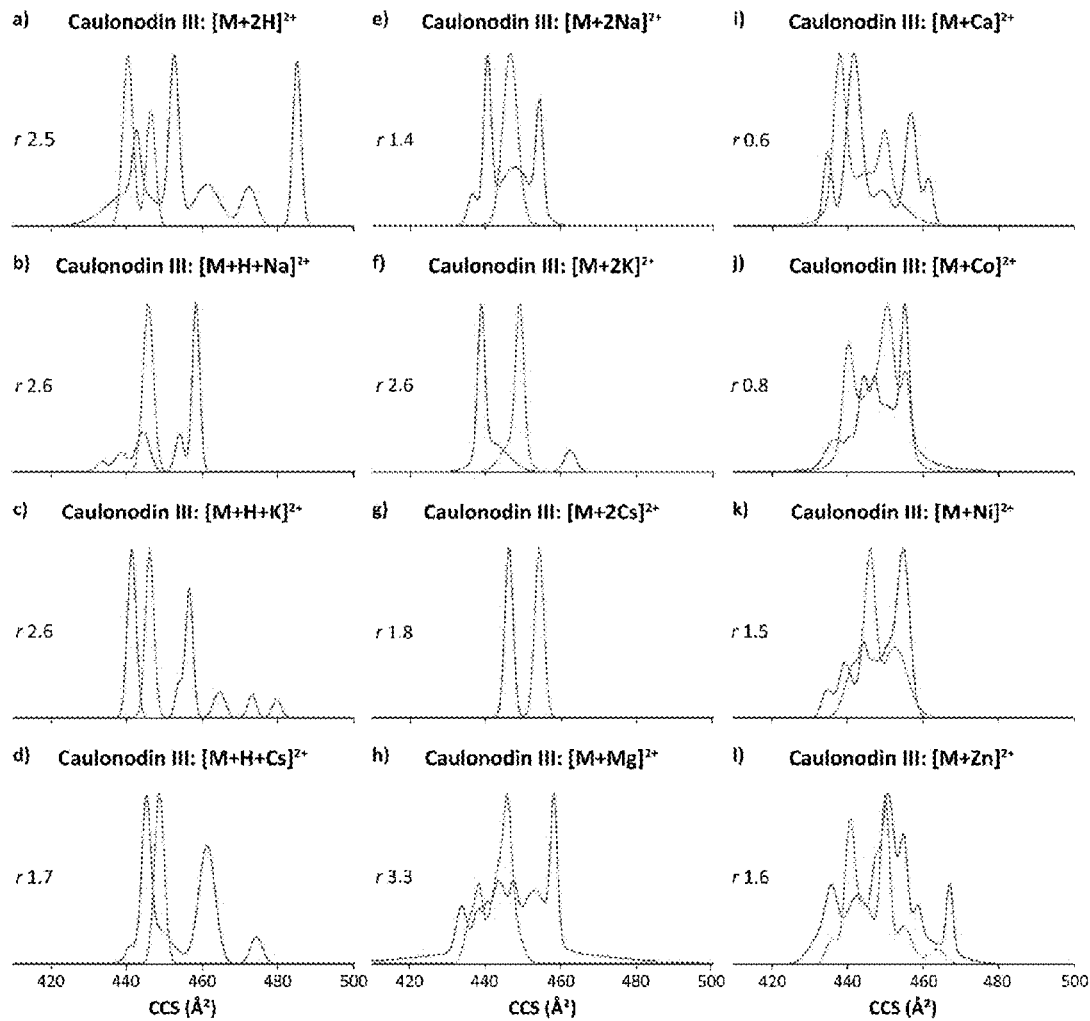
FIGS. 31A-31L show typical TIMS spectra for caulonodin III (blue traces) and its branched-cyclic (red traces) topoisomers cationized by (A) protonated, (B, E) sodiated, (C, F) potassiated, (D, G) cesiated, (H) magnesiated, (I) calciated, (J) cobaltiated, (K) nickelated and (L) zincated species. A typical Sr of 0.56 V/ms was used and the resolution (r) values are given.
Figures 32A, 32B, 32C, 32D, 32E, 32F, 32G, 32H, 32I, 32J, 32K, 32L:
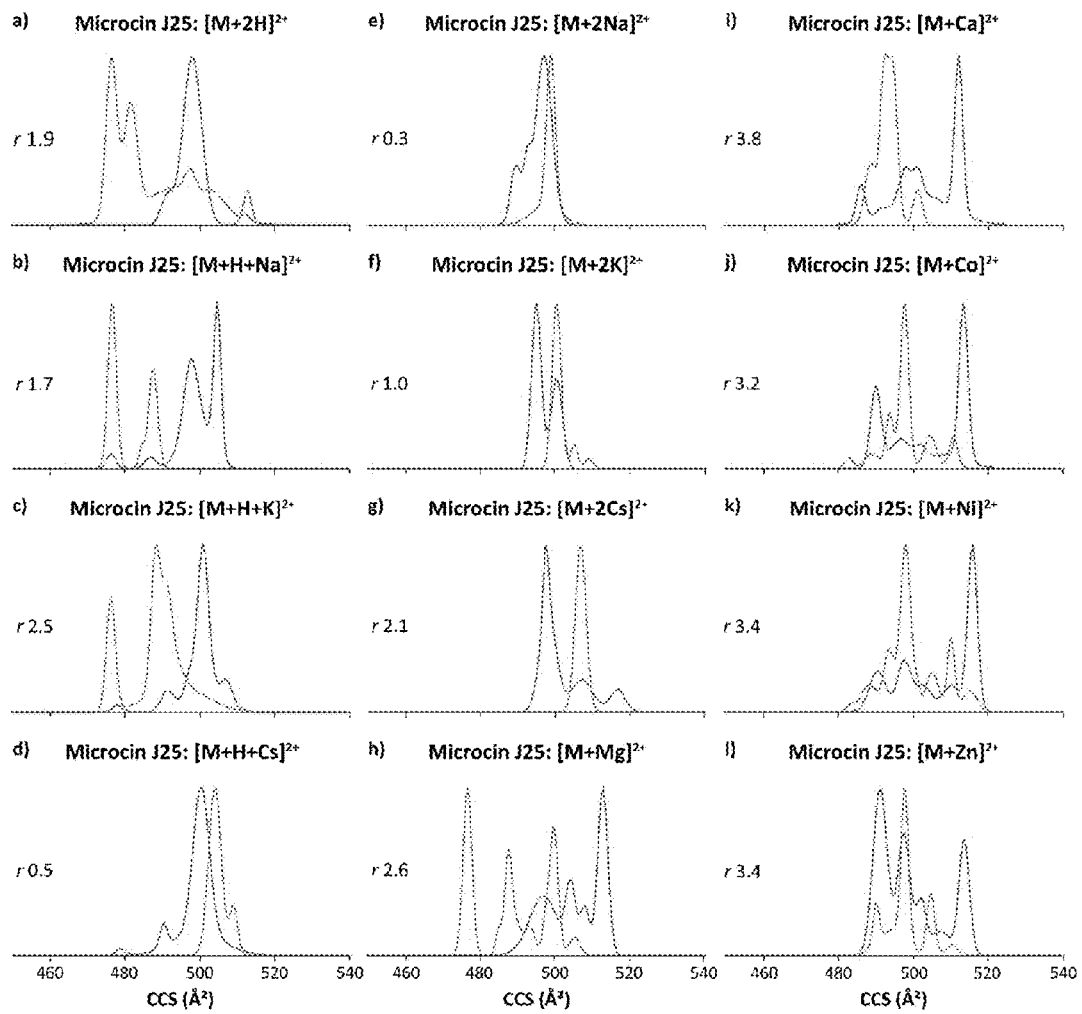
FIGS. 32A-32L show typical TIMS spectra for microcin J25 (blue traces) and its branched-cyclic (red traces) topoisomers cationized by (A) protonated, (B, E) sodiated, (C, F) potassiated, (D, G) cesiated, (H) magnesiated, (I) calciated, (J) cobaltiated, (K) nickelated and (L) zincated species. A typical Sr of 0.56 V/ms was used and the resolution (r) values are given.

The effect of alkali (Na, K and Cs), alkaline earth (Mg and Ca) and transition (Co, Ni and Zn) metal ions on the TIMS separation of lasso and branched-cyclic topoisomers is illustrated in FIGS. 29-32 for syanodin I, sphingonodin I, caulonodin III and microcin J25, respectively. Inspection of FIG. 29 shows that for all cases, except the singly sodiated (r=0.2, FIG. 29B) and potassiated (r=0.5, FIG. 29C) species, the metalated species resulted in higher IMS resolution (r, by at least a factor of 2) between the lasso and branched-cyclic topoisomers compared to the IMS resolution achieved using the protonated species, enabling their identification at fast scan rates (Table 6). Concerning sphingonodin I (FIG. 30 and Table 6), caulonodin III (FIG. 31 and Table 6) and microcin J25 (FIG. 32 and Table 6), for which protonated species are well resolved, the metalated species generally did not improve or resulted in comparable IMS resolution as compared to the protonated species. However, several metal ions allowed to obtain higher IMS resolution in the case of the singly potassiated (r=4.7, FIG. 30C) and cesiated (r=4.8, FIG. 30D) species for sphingonodin I, the magnesiated (r=3.3, FIG. 31H) species for caulonodin III and the magnesiated (r=2.6, FIG. 32H), calciated (r=3.8, FIG. 32I), cobaltiated (r=3.2, FIG. 32J), nickelated (r=3.4, FIG. 32K) and zincated (r=3.4, FIG. 32L) species for microcin J25. The most pronounced difference was observed for the [M+2Na]$^{2+}$ (r=3.4, FIG. 29E), [M+H+Cs]$^{2+}$ (r=4.8, FIG. 30D), [M+Mg]$^{2+}$ (r=3.3, FIG. 31H) and [M+Ca]$^{2+}$ (r=3.8, FIG. 32I) species of syanodin I, sphingonodin I, caulonodin III and microcin J25, respectively.

All these results did not display a general trend in term of IMS resolution and therefore suggest that metal ion binding rearrange lasso and branched-cyclic structures in different ways, which involves trying diverse metal ions to maximize resolution. However, a different number of IMS bands are observed as a function of the metal ion size for the same charge state in both topoisomers. For example, while the TIMS distribution of the metalated lasso and branched-cyclic peptide ions typically consisted of multiple bands, the TIMS distribution of the doubly cesiated species resulted in a single band for each lasso and branched-cyclic peptide couple (except for microcin J25 branched-cyclic that presents two minor IMS bands), therefore improving the discrimination between these topoisomers in the gas-phase (FIGS. 29G, 30G, 31G and 32G). The presence of the two additional minor IMS bands for the branched-cyclic form of microcin J25 (FIG. 32G) could be explained by the longer length of its C-terminal region (13 residues, Table 1), as compared to the other branched-cyclic peptides (9 residues, Table 1), which significantly increase the flexibility of this region, permitting additional interactions with the cesium ions. These results illustrate the potential of the doubly cesiated species to provide a unique conformation as an efficient analytical feature for the identification of the lasso fold and corresponding branched-cyclic topoisomers at physiological conditions, using high resolution native nESI-TIMS.

Separations of DAACP Epimers

Figure 33A:
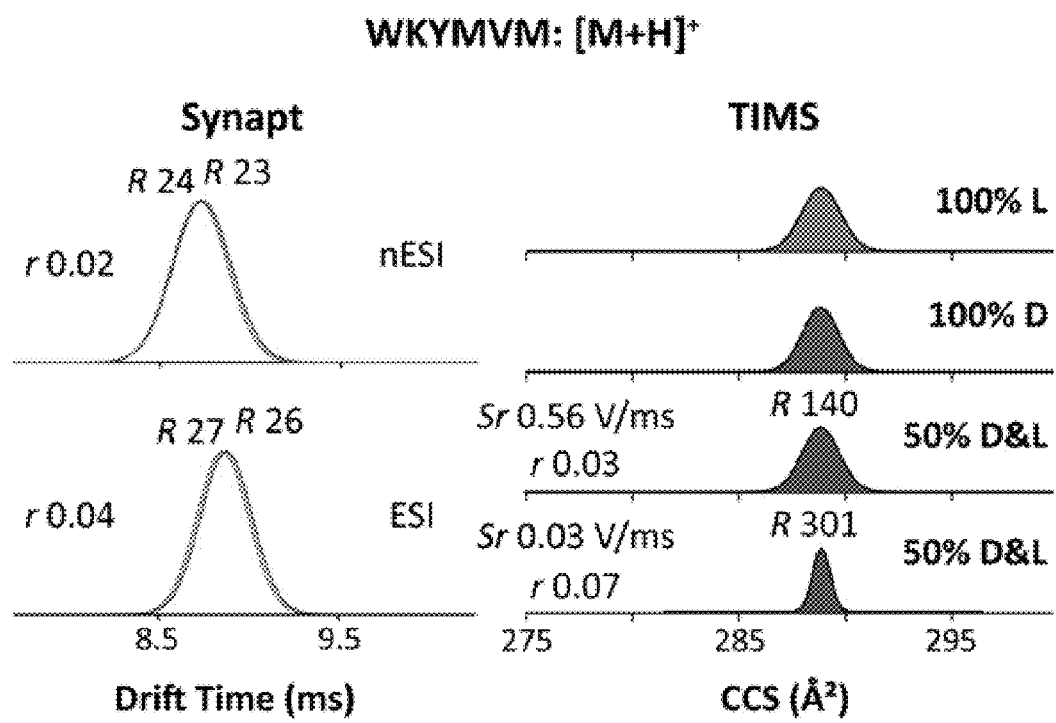
FIGS. 33A-33B show IMS spectra using Synapt (left) and TIMS (right) for WKYMVM (SEQ ID NO: 4) cationized by (A) protonated and (B) potassiated species. The epimers are colored in blue (L), red (D) and magenta (merged epimers). The TIMS spectra for mixtures employed different scan rates as marked. The R and r values are given.
Figure 33B:
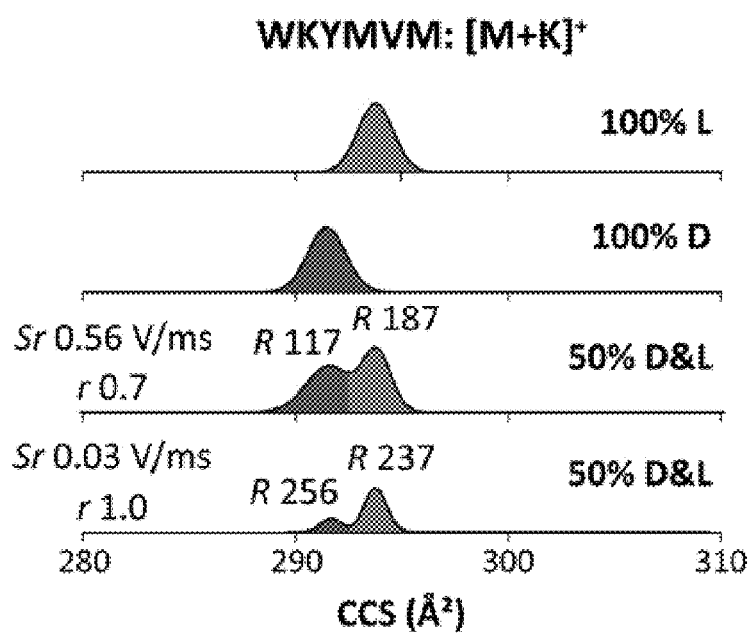

With WKYMVM (SEQ ID NO: 4), the epimers for $[M+H]^+$ and $[M+2H]^{2+}$ ions coincide in both Synapt and TIMS, with r<0.1 in TIMS even at R=300 reached at slow scan rates (FIG. 33A). In this sole case, the protonated epimers could not be disentangled. A possible solution is changing the cationization mode. For one, metalated biomolecules tend to differ in conformation from protonated analogs as the metal ion is multiply charged, binds at another site, and/or coordinates differently because of specific chemistry. If these deviations are unequal for two epimers, metalation can enhance their resolution. Single $K^+$ adducts generated by spiking the sample with $K_2CO_3$ at 70 μM (FIG. 33B) were measured. While the peak widths barely change, potassiation increases Ω by 0.9% (2.6 Å$^2$) for the D-epimer but 1.6% (4.8 Å$^2$) for the L-epimer, enabling their complete resolution (r=1.0) at slow scan rates (Table 8).

Example 5—Evaluating the Dynamic Range and Coupling to MS/MS

Figures 12A, 12B, 12C:
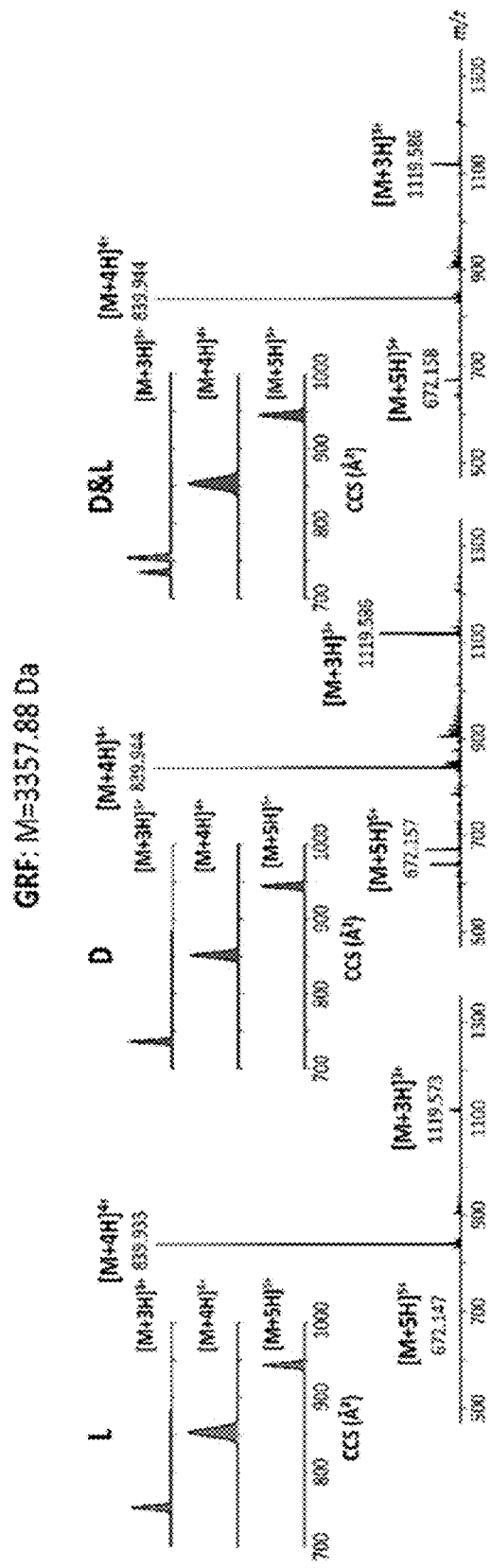
FIGS. 12A-12C show mass spectra and ion mobility profiles using TIMS of A) GRF (blue trace), B) (D-Ala2)-GRF (red trace) and C) in mixture (magenta trace).

The largest peptide examined here (GRF) exhibits multiply protonated species ranging from $[M+3H]^{3+}$ to $[M+5H]^{5+}$ (FIGS. 12A-12C). In TIMS, the D/L-epimers are resolved baseline for the $[M+3H]^{3+}$ ions [$\Delta\Omega_r$=2.2% (16.2 Å$^2$) and r=2.4 with D-isomer at lower Ω], but coincide for $[M+4H]^{4+}$ and $[M+5H]^{5+}$ ions (r<0.1).

Figure 34A:
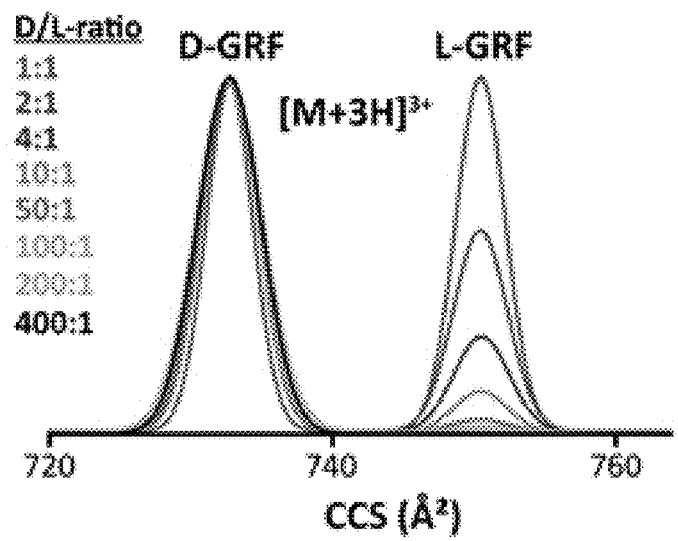
FIGS. 34A-34D show separation and CID (70 V) for the $[M+3H]^{3+}$ ions of the D/L-epimers of GRF (SEQ ID NO: 26) using TIMS: (A) IMS spectra for mixtures with various D/L-ratios obtained using Sr=0.036 V/(ms), (B) Calibration curve with MS spectra for highest and lowest ratios, (C) IMS spectrum for the 400 ratio in logarithmic scale, (D) CID spectra at L- and D-peaks with masses and assignments for significant products (also mapped onto the peptide sequence).
Figure 34B:
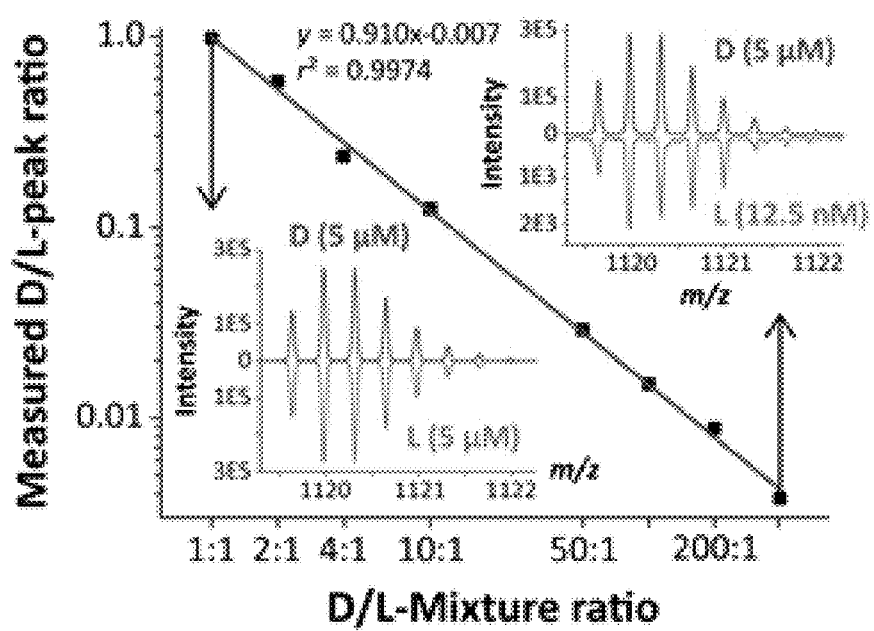
Figure 34C:
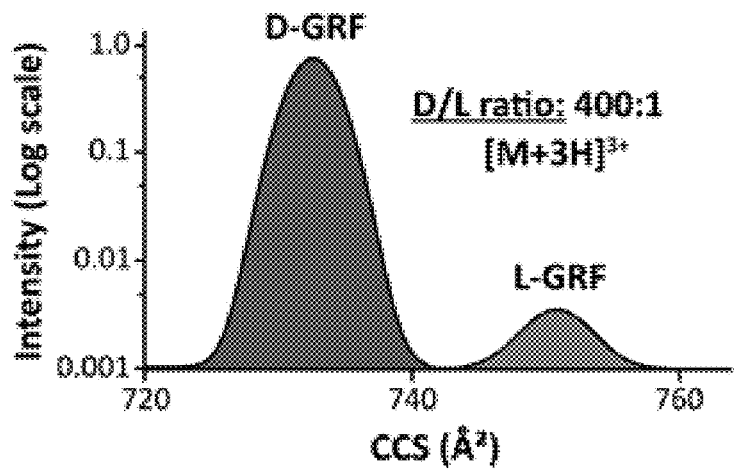

Components can be more difficult to resolve in non-isomolar mixtures of large dynamic range as the sides of (ideally Gaussian) distributions for intense peaks can subsume adjacent weaker features, particularly when most of real samples comprise unequal epimer fractions. To gauge the capability of TIMS in this scenario, mixtures with the D/L-ratio up to 400 were tested. Even at the maximum, the L-epimer was clearly resolved by IMS with s/n=10 in the MS spectrum (FIGS. 34A-34C). Good linear quantification ($r^2$=0.9974) extends down to $f_{LOQ}$=0.25% with substantially lower $f_{LOD}$. These metrics are much superior to the best benchmarks from MS/MS ($f_{LOD}$~1-10%).

The IMS-resolved epimers could be assigned based on tabulated Ω and/or fingerprint MS/MS spectra. The latter can also reduce $f_{LOQ}$ and $f_{LOD}$ by quantifying the isomer ratio at minor peaks partly covered by the wings of major peaks. In principle, an RDD analysis with $f_{LOD}$=2% after IMS separation with present $f_{LOD}$<0.25% would yield total $f_{LOD}$<50 ppm (assuming sufficient signal averaging). The methods disclosed herein can perform CID that provides some epimer discrimination.

Figure 34D:
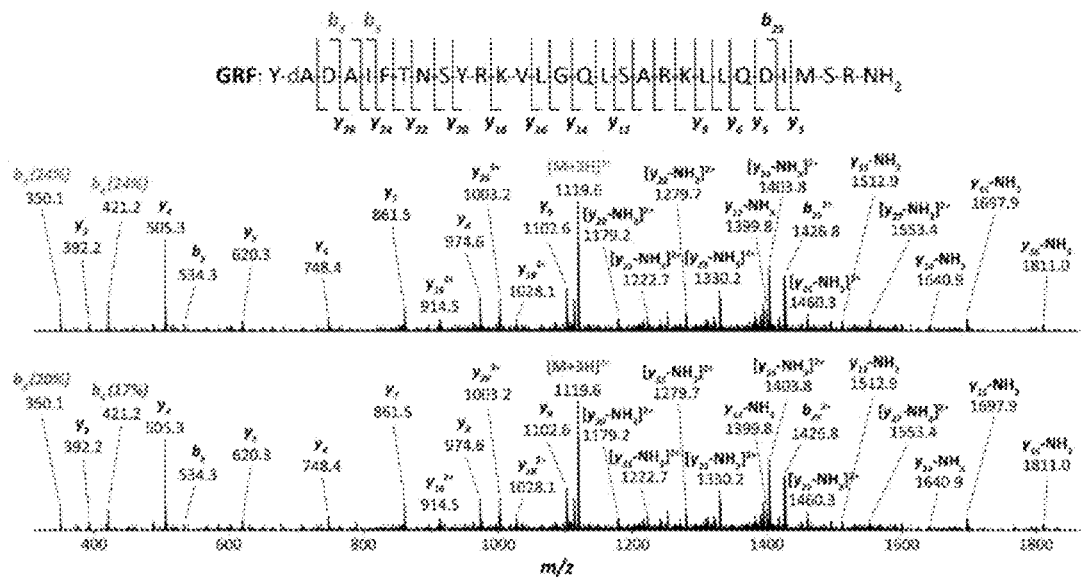

The CID spectra for D- and L-isomers are very close (FIG. 34D). Both show the classic $b_n$ and $y_n$ fragments, with $y_n$ dominant since basic residues in GRF cluster toward the C-terminus. The only reproducible distinction between two spectra is a bit lower yield of $b_3$ and $b_4$ (the smallest observed fragments comprising the D/L-Ala2) for the D-epimer (FIG. 34D). This may follow from slightly higher energy required to sever the backbone in that region for the D-epimer, in line with its lower Ω suggesting a tighter fold. ENREF_68_ENREF_64 While the MS/MS spectral difference happens to be marginal here, this example illustrates the advantages of online mobility-separated collision-induced dissociation (CID) followed by high-resolution mass spectrometry (TIMS-CID-MS) for epimer separation, sequencing, and relative quantification.

Example 6—Correlations Between TWIMS, TIMS, and FAIMS Separations of Proteoforms The analyses of same peptide set in FAIMS and two linear IMS systems allows investigating the correlations between separations within and between those dimensions, namely across charge states in (1) TWIMS and (2) TIMS, and for same species between (3) TWIMS and TIMS, (4) TWIMS and FAIMS, and (5) TIMS and FAIMS.

Figure 35:
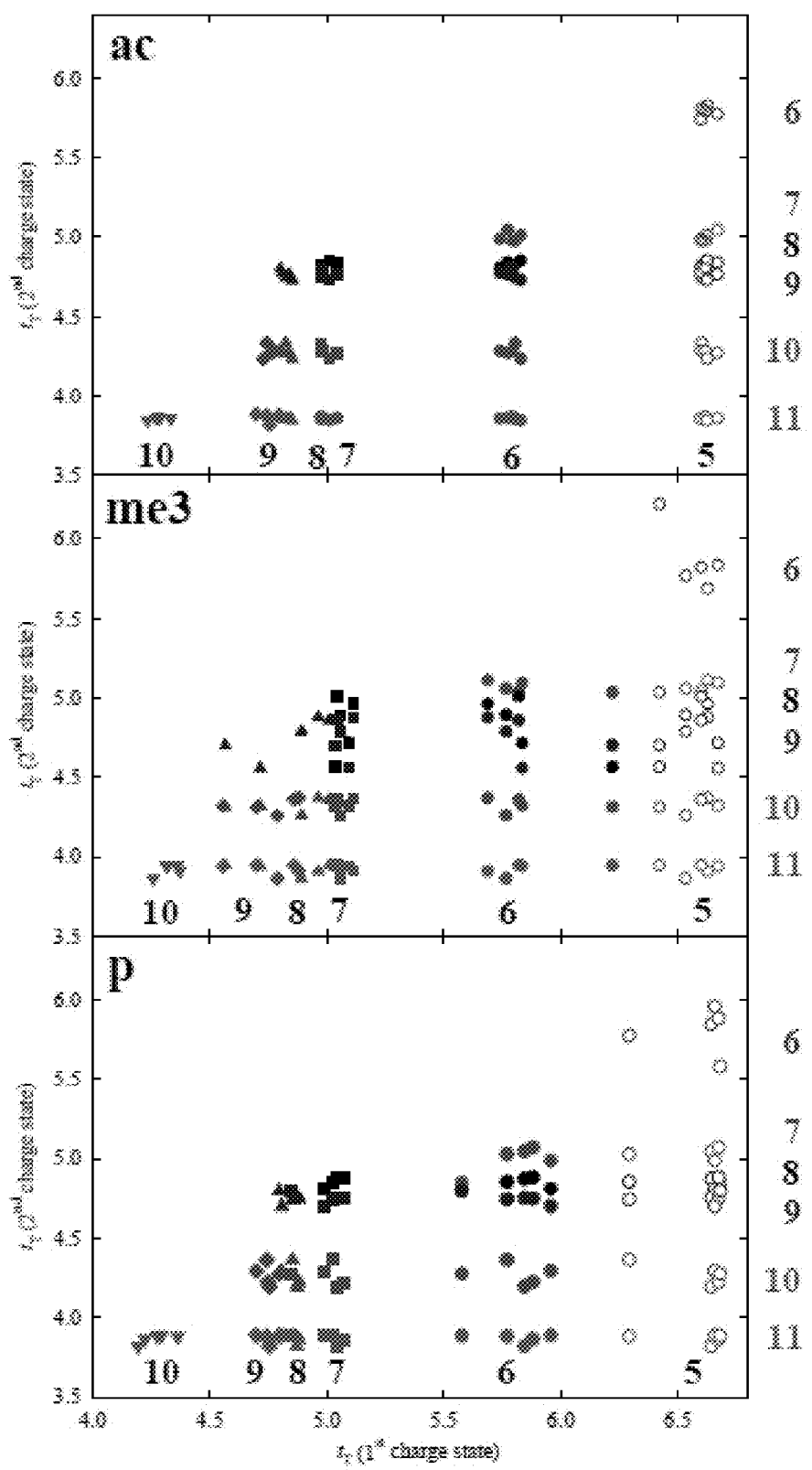
FIG. 35 shows linear correlations between transit times for me3, ac, and p variants across charge state pairs (major peaks from FIG. 16). Variants for me (with three data points) are not included.
Figure 36A:
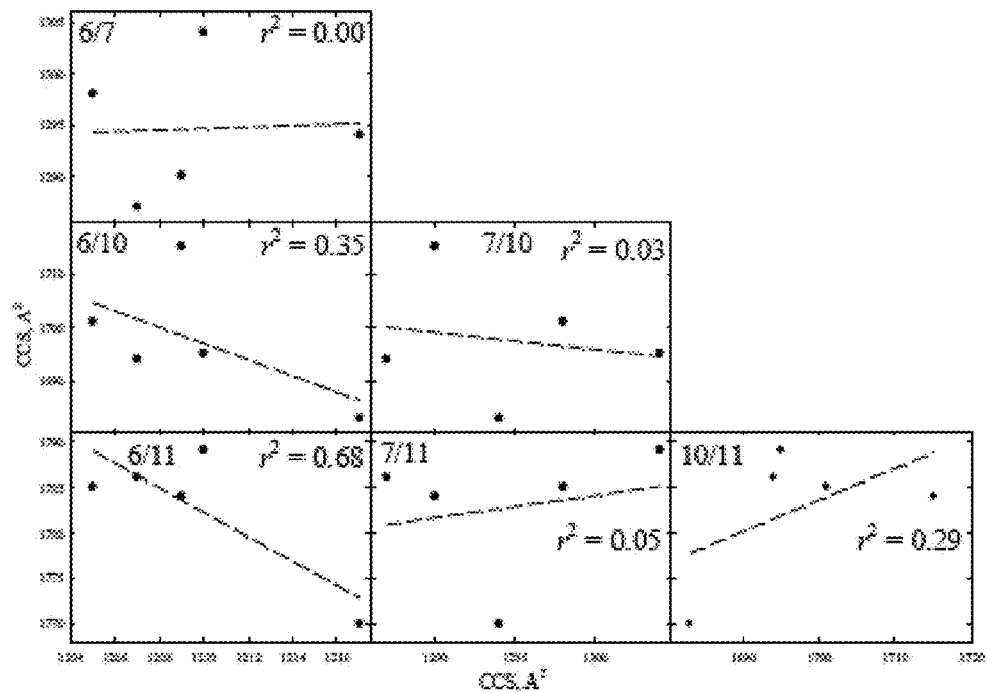
FIGS. 36A-36B show linear correlations between separation parameters in TIMS for the acetylated and phosphorylated peptide variants in different charge states.
Figure 36B:
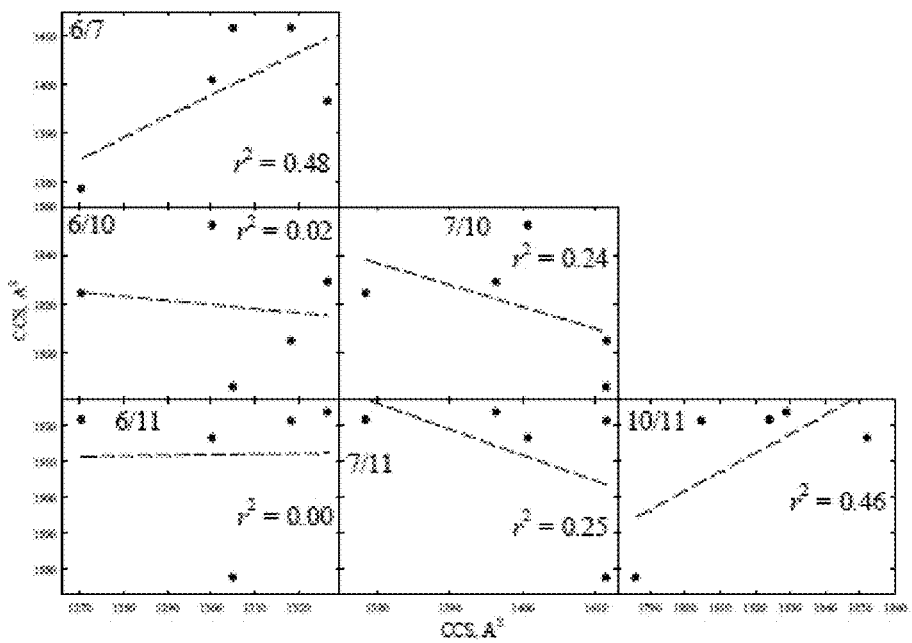

Separations of all variants in TWIMS notably differ across charge states. This may be quantified via pairwise linear correlation between separation parameter sets. Here, the mean $r^2$ for $t_T$ correlations over z=5-11 (FIG. 35) equal 0.23, 0.24, and 0.25 for me3, ac, and p variants (with 21 pairs each). The values for Ω in TIMS are same: 0.23 (ac variants) and 0.24 (p variants) for z=6, 7, 10, 11 with single dominant peaks (FIGS. 36A-36B), and 0.26 and 0.18 respectively if one adds z=8 and 9 using base peaks. The aggregate $r^2$ over all PTMs is 0.24±0.04 std. error (for 63 pairs) with Synapt and same 0.22±0.03 with TIMS, also equal to 0.25±0.05 (for 30 pairs with z=8-12 for me3, ac, and p variants) with FAIMS (Table 11). This manifests an essentially perfect orthogonality across charge states, previously demonstrated in FAIMS but not linear IMS separations of any PTM localization variants.

TABLE 11

Summary of linear correlations between separations (averaged over all PTMs and charge states): $r^2$ values with std. errors of mean

|  | Synapt (z1) | TIMS (z1) | FAIMS (z1) |
|---|---|---|---|
| Synapt (z1) | 0.91 ± 0.03[a] |  | 0.52 ± 0.10[e] |
| Synapt (z2) | 0.24 ± 0.04[b] |  | 0.22 ± 0.05[f] |
| TIMS (z1) | 0.86 ± 0.05[c] |  | 0.52 ± 0.11[g] |
| TIMS (z2) |  | 0.22 ± 0.03[d] | 0.22 ± 0.04[h] |
| FAIMS (z2) |  |  | 0.25 ± 0.05[i] |

[a] In Synapt at s = 650 vs. s = 1000 m/s
[b] In Synapt for same peptides in different z
[c] For same ion species in Synapt vs. TIMS
[d] In TIMS for same variants in different z
[e] For same ion species in Synapt vs. FAIMS (8 pairs)
[f] For variants in Synapt vs. same variants with different charge states in FAIMS (24 pairs)
[g] For same ion species in TIMS vs. FAIMS (8 pairs)
[h] For variants in TIMS vs. same variants with different charge states in FAIMS (24 pairs)
[i] In FAIMS for same variants in different z (30 pairs).

Figure 37:
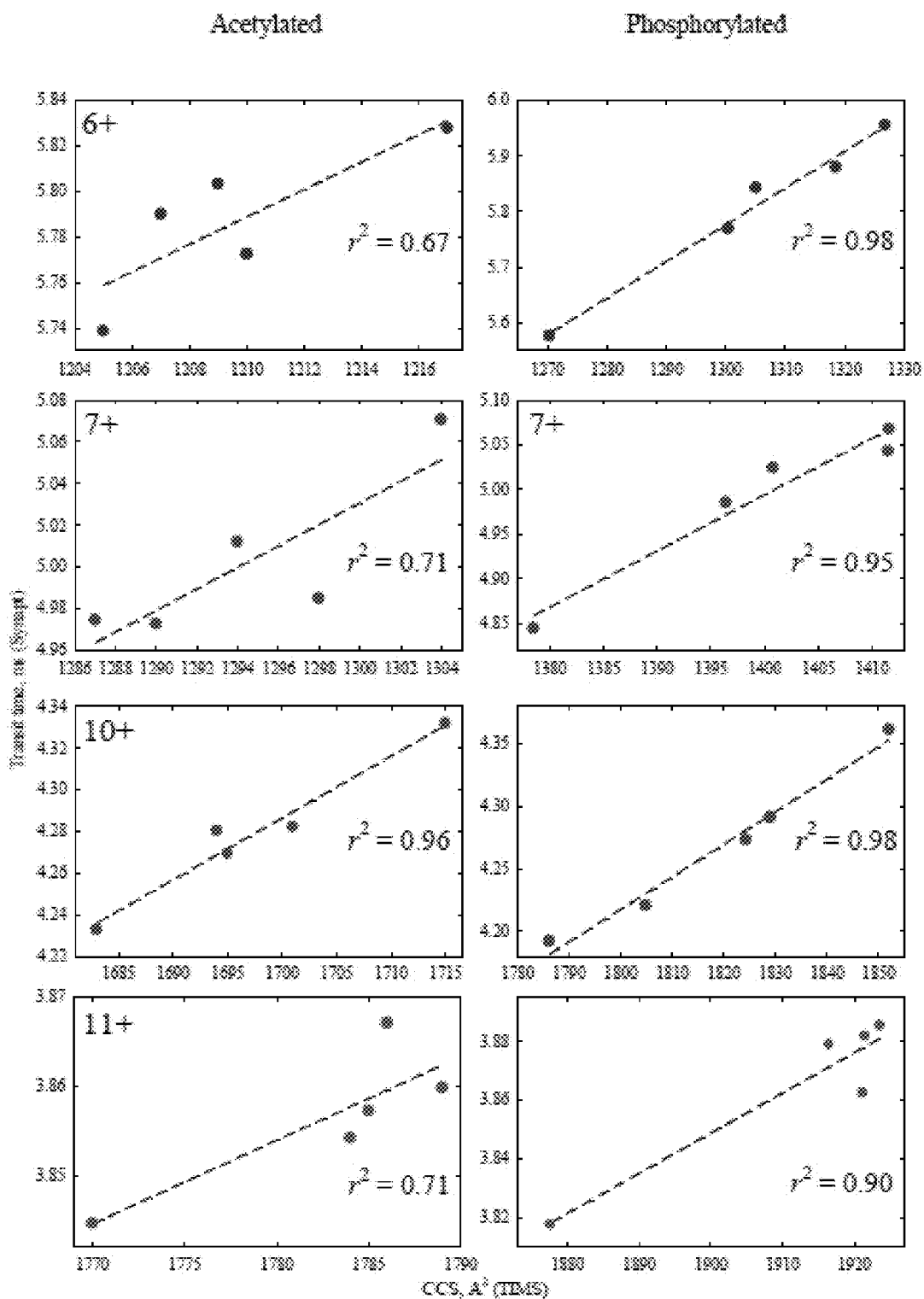
FIG. 37 shows linear correlations between separation parameters in Synapt and TIMS for the acetylated and phosphorylated peptide variants.

The correlation can be quantified between the two linear IMS separations apparent from above comparisons of cross sections (FIG. 17) and specific spectra (FIGS. 16 and 24), best for ac and p variants with five $t_T$ or Ω points in each dimension. Calculations for z=8 and 9 are complicated by multiple intense features in both data sets that need integration. Therefore, the comparison was restricted to z=6, 7, 10, 11 with at most two major peaks. The resulting $r^2$ (FIG. 37) are 0.7-1.0 (mean=0.76) for ac variants and 0.9-1.0 (mean=0.95) for p variants (higher $r^2$ for the latter reflect a greater variant separation diminishing the relative random error of peak spacings). These values with aggregate $r^2=0.86\pm0.05$ (Table 11) show strong correlation, especially as (i) the smaller features in TIMS spectra were ignored and (ii) $t_T$ is not proportional to $\Omega$. The overall accord between TWIMS and TIMS data despite dissimilar ESI and ion heating regimes and ~50× longer separation in TIMS show the peptide ion geometries conserved over ~5-300 ms and supports the formation of equilibrium conformers in the source. Present similarity between TWIMS and TIMS separations mirrors that for peptides with D- or L-amino acid in certain position, though just two variants per peptide there allowed no $r^2$ values.

This orthogonality of separations across charge states, their number generated by ESI, and impressive resolving power enable TIMS to disentangle all variants tried to at least the binary mixtures quantifiable by ETD. That said, uniform separation to individual variants would be beneficial. Also, the histone stoichiometries have up to ~50 known variants, with further less abundant likely to be discovered. Fully characterizing such complex endogenous samples involving spectral congestion requires yet greater peak capacity (pc) that could come from 2-D FAIMS/IMS separations, depending on the orthogonality between dimensions.

Figure 38:
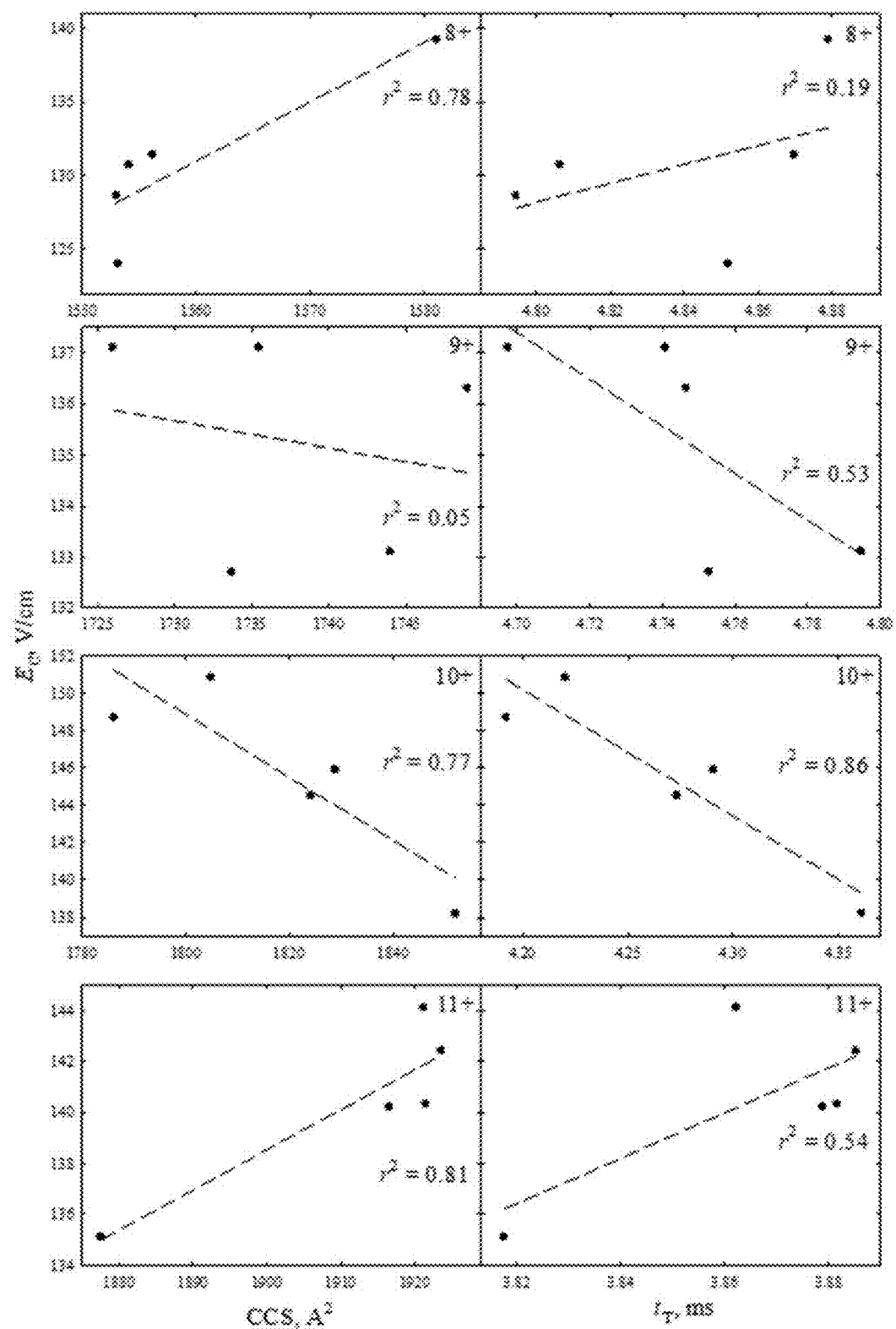
FIG. 38 shows linear correlations between FAIMS and TIMS (left) or TWIMS (right) separations with $r^2$ marked, for p variants.
Figure 39A:
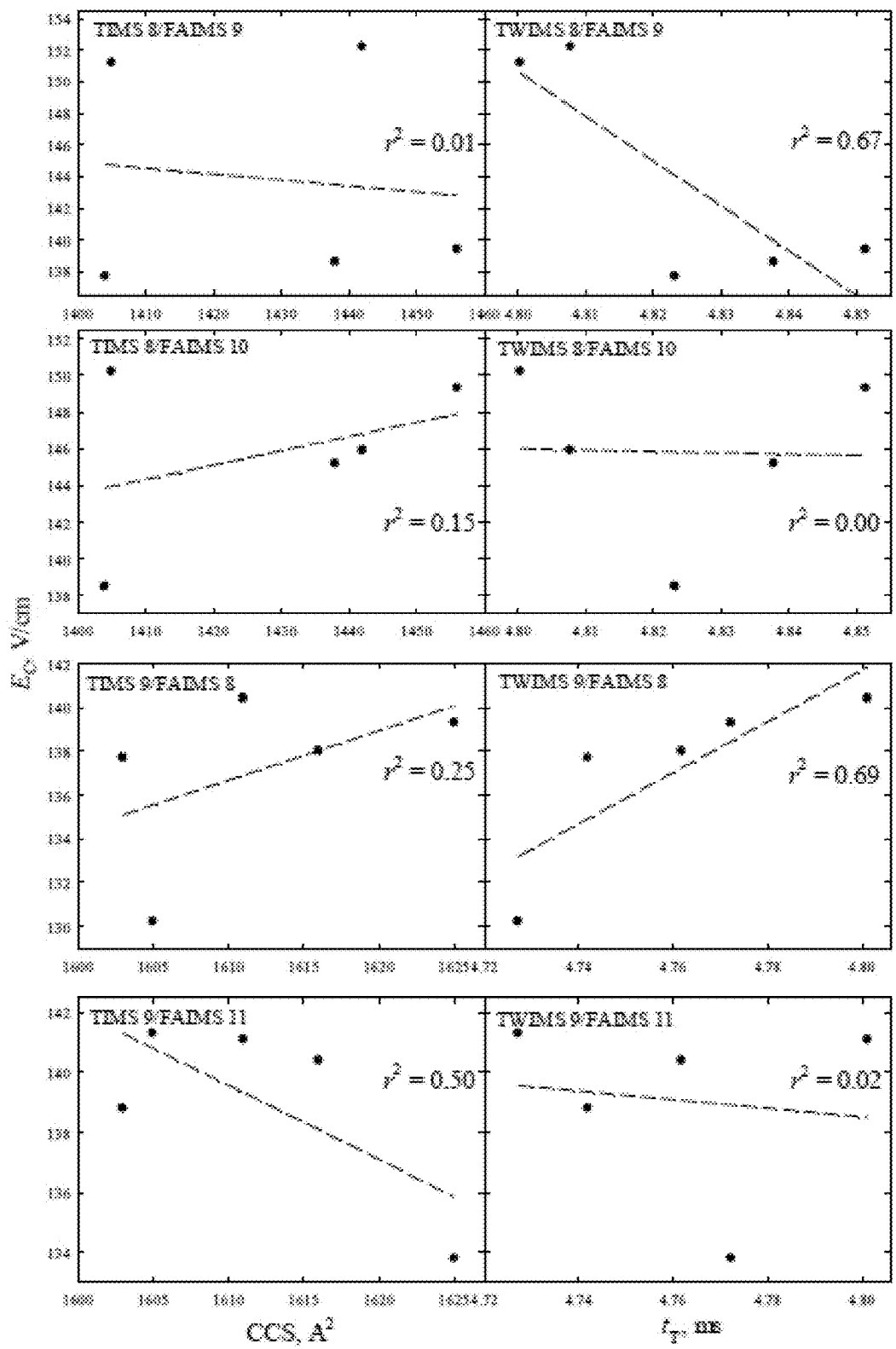
FIGS. 39A-39D show linear correlations between FAIMS and TIMS (left) or TWIMS (right) separations for acetylated (A and B) and phosphorylated (C and D) variants with different charge states selected in the two dimensions ($r^2$ marked).
Figure 39B:
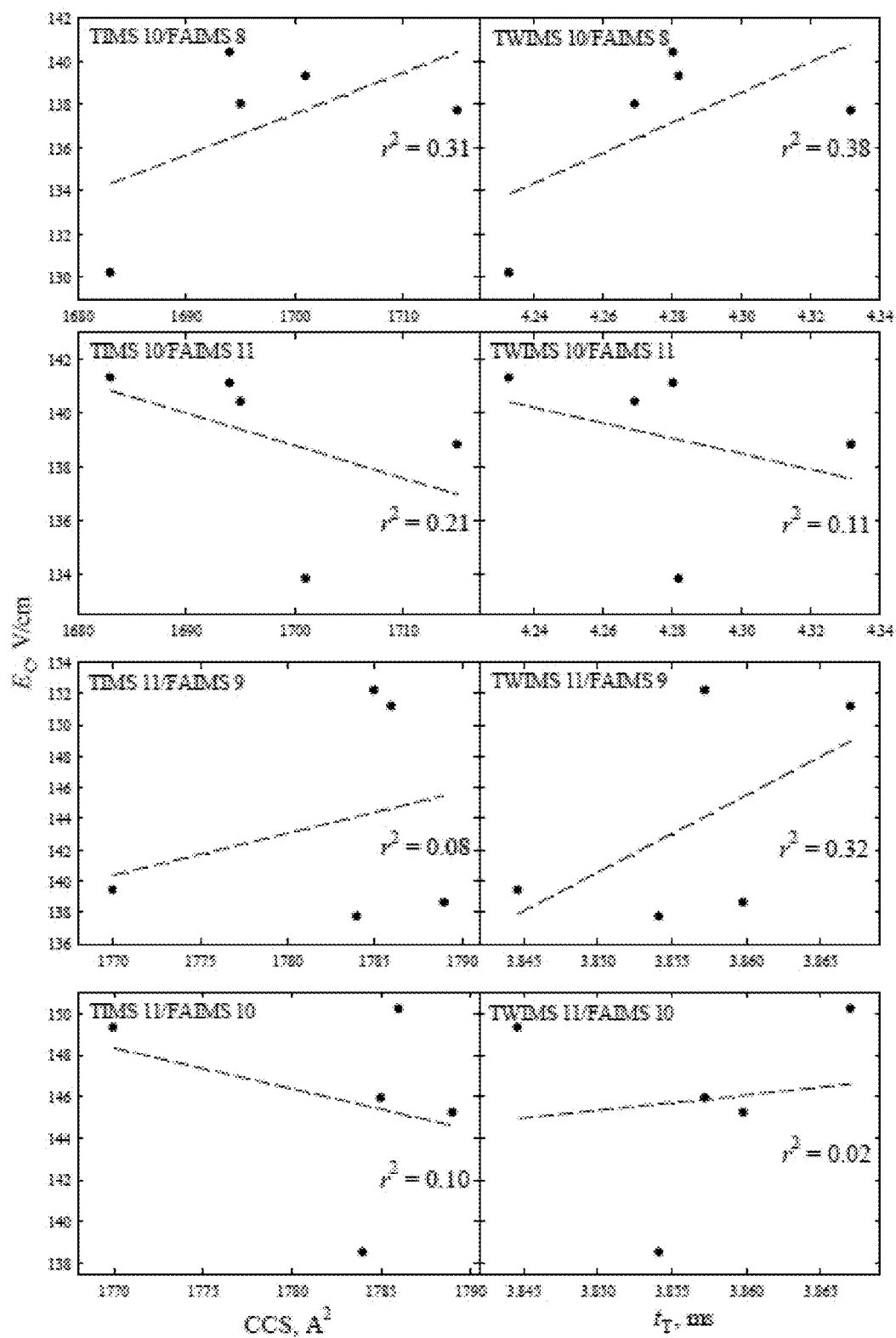
Figure 39C:
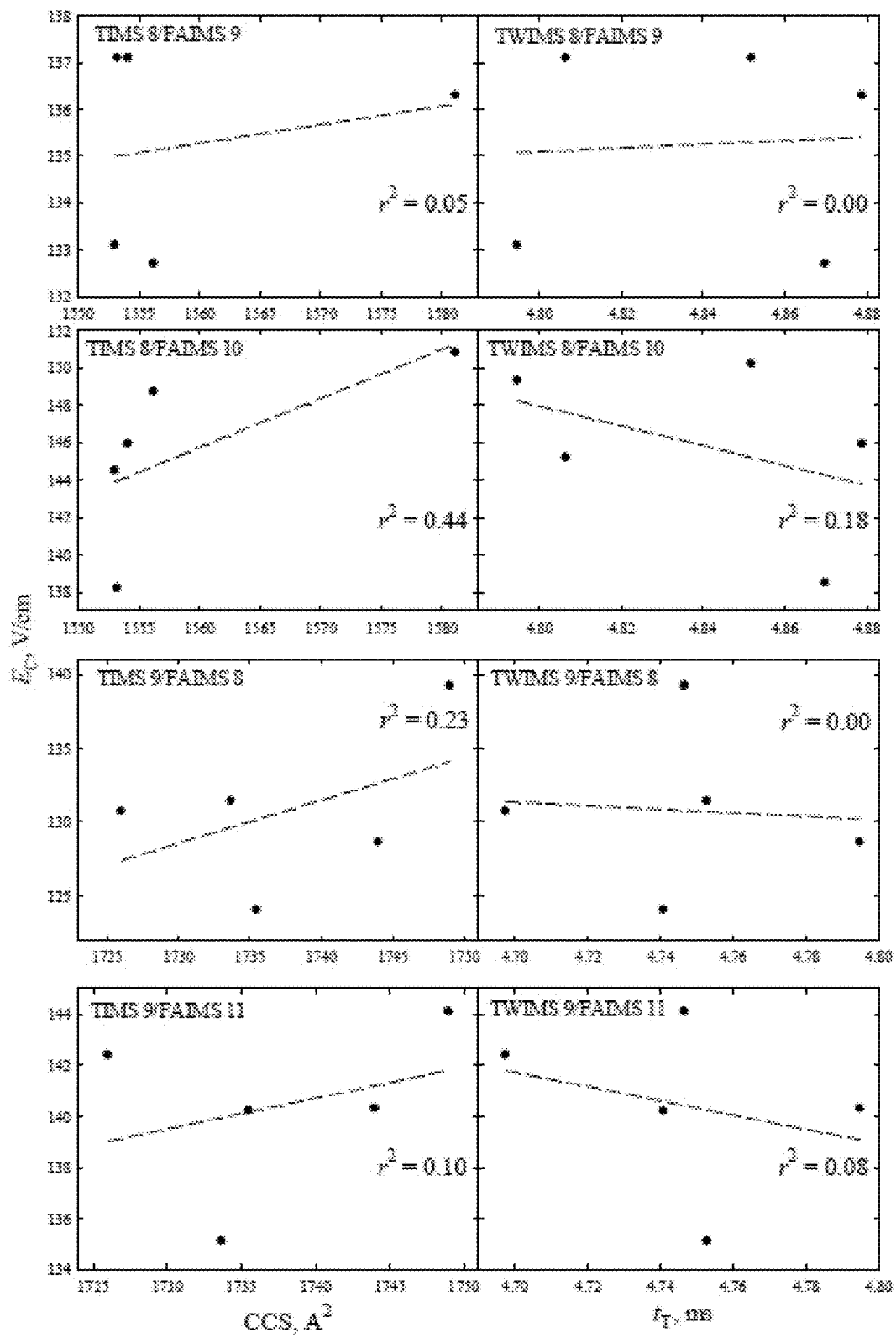
Figure 39D:
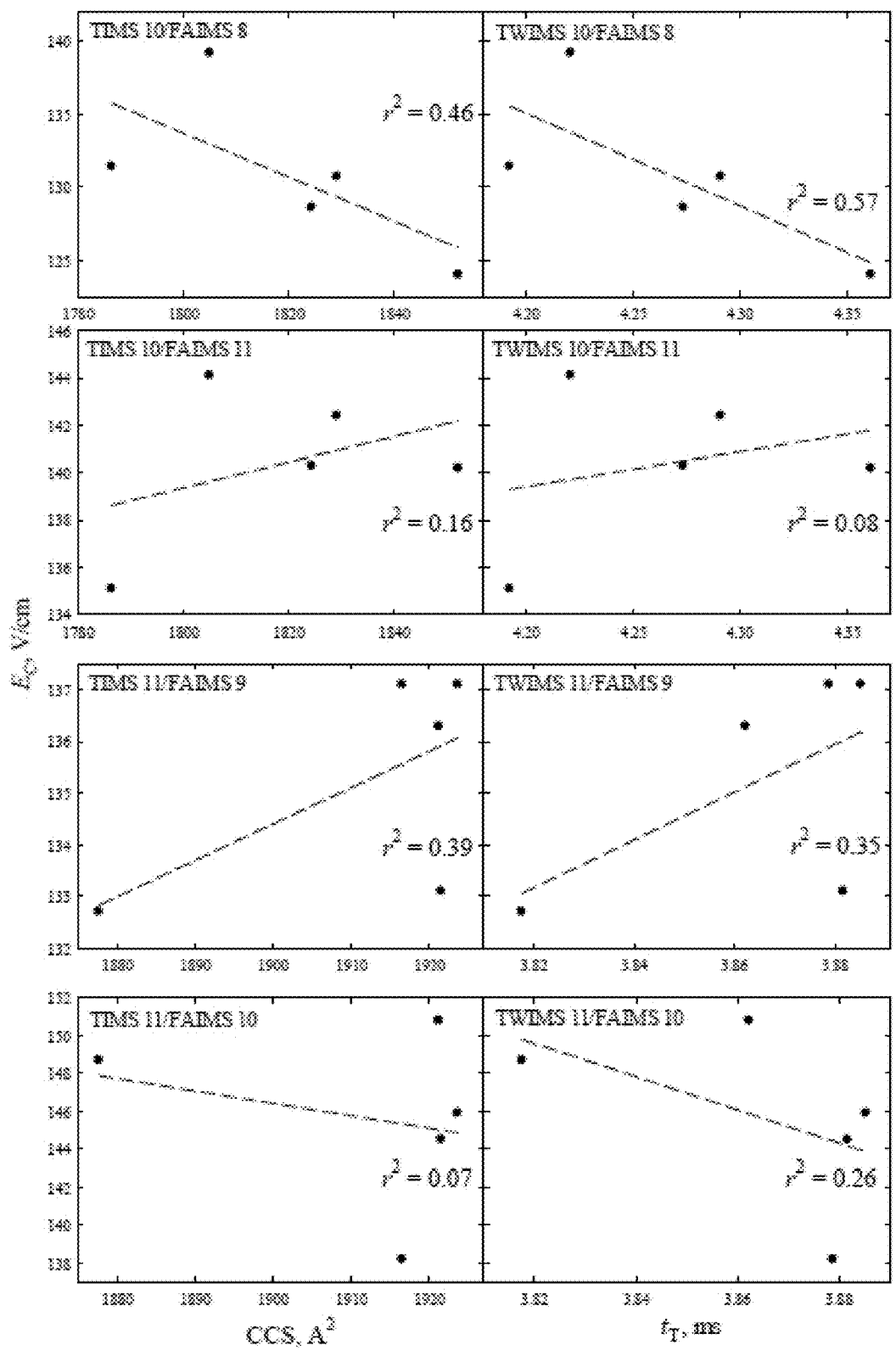
Figure 40:
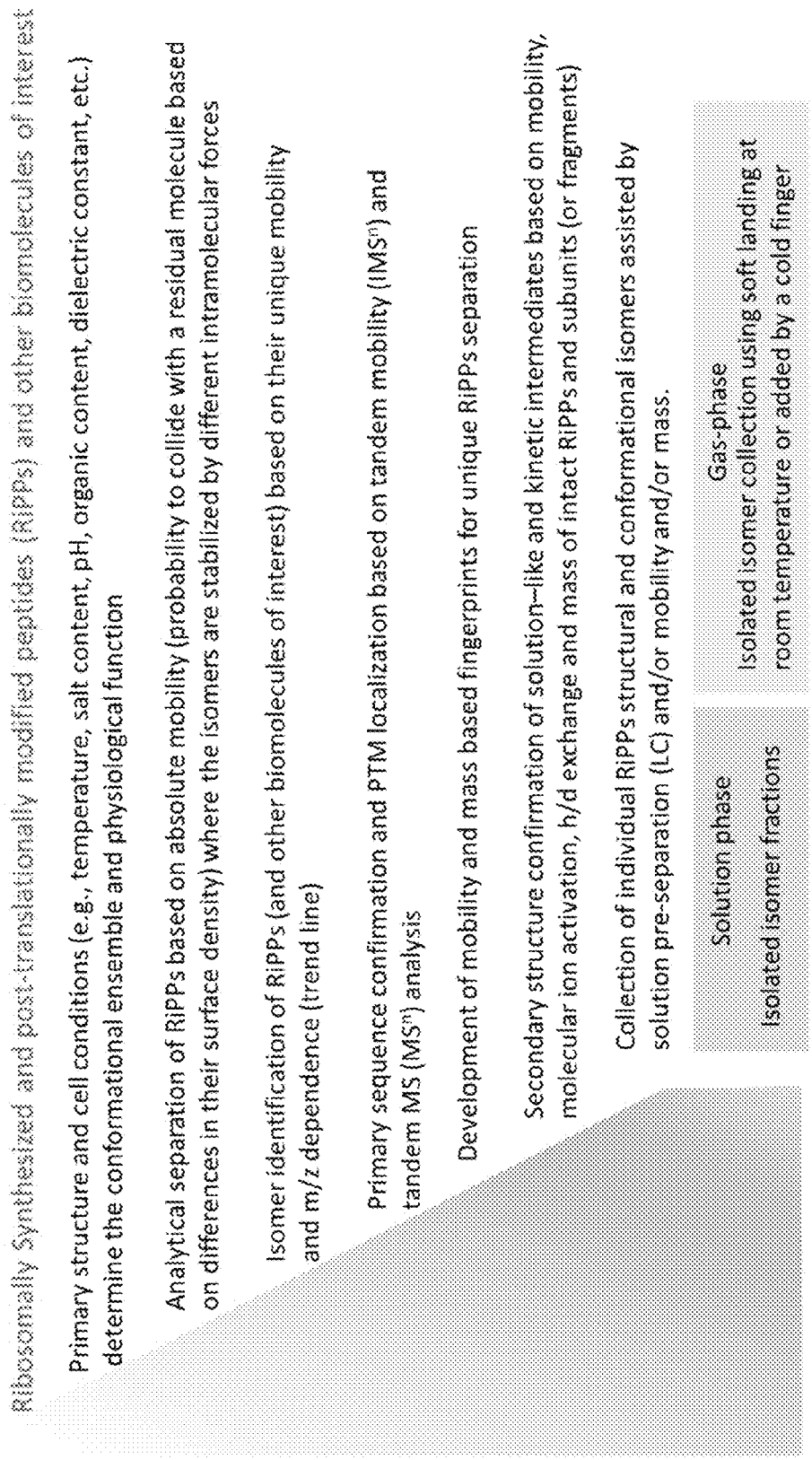
FIG. 40 shows schematic representation of an embodiment of the instant methods of identifying and/or isolating and optionally, further characterizing isomers of molecules from certain biological samples.

The complementarity of FAIMS and linear IMS separations of histone tails is evident from different loci of variant resolution across charge states. For example, that for me3 variants maximizes for z=8 and 9 in TWIMS (FIG. 16) or TIMS (FIG. 24) vs. 10 and 11 in FAIMS. Within a given state, some variants resolved by FAIMS may co-elute in TIMS and vice versa. For instance, in z=10, the K18ac and K27ac merged in TIMS are separated by FAIMS baseline, whereas TIMS partly resolves K14ac and K27ac merged in FAIMS. Broadly, the FAIMS dimension is correlated to TWIMS/TIMS with mean $r^2$ (over z=8-11) of 0.51/0.42 for ac variants and 0.53/0.60 for p variants (FIGS. 38A-38B), with the aggregate of 0.52±0.07 for 16 pairs (Table 11). Proteomic findings are often validated by negative testing of a priori false suppositions using decoy databases. Inspired by that concept, the "decoy correlations" of FAIMS to TWIMS/TIMS separations for same variants in all wrong charge states were computed (48 pairs, FIGS. 39A-39D). The associated mean $r^2$ of 0.22+0.05 (with TWIMS or TIMS) is away from the above for correct states, but matches the $r^2$ for correlations across those in TWIMS or TIMS that apparently correspond to the random baseline (Table 11). Therefore the present ~50% correlation between linear IMS and FAIMS is real, and close to that for tryptic peptides.

Accordingly, the 2-D pc of FAIMS/IMS separations for middle-down peptides must equal ~½ of the product of pc for each stage (defined as the occupied separation space, d, over mean w of present peaks). Here in TIMS, the typical d~100 Å and w~10 Å in a "good" charge state yield pc~10 (e.g., 8 for p variants in 6+ and 10+, or 14 and 11 for me3 variants in 8+ and 9+). In FAIMS, the typical pc in one state was ~25 (with d~30 V/cm and w~1.2 V/cm). Hence the pc of FAIMS/IMS would be ~125 in one state, and easily >500 in all (near-orthogonal) states. The values would be greater yet for more complex samples (as the separation space statistically widens), and the number of available charge states can be augmented (e.g., via supercharging). Despite much of this pc taken up by the conformers of each variant, it should still suffice to largely fractionate the known isomeric proteoform sets at least into binary mixtures.

All patents, patent applications, provisional applications, and publications referred to or cited herein are incorporated by reference in their entirety, including all figures and tables, to the extent they are not inconsistent with the explicit teachings of this specification.

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. J. D. Hegemann, M. Zimmermann, X. Xie and M. A. Marahiel, Lasso peptides: an intriguing class of bacterial natural products, *Acc. Chem. Res.*, 2015, 48, 1909-1919.
2. C. Lapthorn, F. Pullen and B. Z. Chowdhry, Ion mobility spectrometry-mass spectrometry (IMS-MS) of small molecules: separating and assigning structures to ions, *Mass Spectrom. Rev.*, 2013, 32, 43-71.
3. G. Paglia, M. Kliman, E. Claude, S. Geromanos and G. Astarita, Applications of ion-mobility mass spectrometry for lipid analysis, *Anal. Bioanal. Chem.*, 2015, 407, 4995-5007.
4. Y. Zhong, S. J. Hyung and B. T. Ruotolo, Ion mobility-mass spectrometry for structural proteomics, *Expert Rev. Proteomics*, 2012, 9, 47-58.
5. F. Lanucara, S. W. Holman, C. J. Gray and C. E. Eyers, The power of ion mobility-mass spectrometry for structural characterization and the study of conformational dynamics, *Nat. Chem.*, 2014, 6, 281-294.
6. S. D. Pringle, K. Giles, J. L. Wildgoose, J. P. Williams, S. E. Slade, K. Thalassinos, R. H. Bateman, M. T. Bowers and J. H. Scrivens, An investigation of the mobility separation of some peptide and protein ions using a new hybrid quadrupole/travelling wave IMS/oa-ToF instrument, *Int. J. Mass Spectrom.*, 2007, 261, 1-12.
7. K. Giles, J. P. Williams and I. Campuzano, Enhancements in travelling wave ion mobility resolution, *Rapid Commun. Mass Spectrom.*, 2011, 25, 1559-1566.
8. K. Jeanne Dit Fouque, C. Afonso, S. Zirah, J. D. Hegemann, M. Zimmermann, M. A. Marahiel, S. Rebuffat and H. Lavanant, Ion mobility-mass spectrometry of lasso peptides: signature of a rotaxane topology, *Anal. Chem.*, 2015, 87, 1166-1172.
9. K. Jeanne Dit Fouque, H. Lavanant, S. Zirah, J. Lemoine, S. Rebuffat, J. C. Tabet, A. Kulesza, C. Afonso, P. Dugourd and F. Chirot, Gas-phase conformations of capistruin—comparison of lasso, branched-cyclic and linear topologies, *Rapid Commun. Mass Spectrom.*, 2015, 29, 1411-1419.
10. V. Domalain, V. Tognetti, M. Hubert-Roux, C. M. Lange, L. Joubert, J. Baudoux, J. Rouden and C. Afonso, Role of cationization and multimers formation for diastereomers differentiation by ion mobility-mass spectrometry, *J. Am. Soc. Mass Spectrom.*, 2013, 24, 1437-1445.
11. X. Pang, C. Jia, Z. Chen and L. Li, Structural Characterization of Monomers and Oligomers of D-Amino Acid-Containing Peptides Using T-Wave Ion Mobility Mass Spectrometry, *J. Am. Soc. Mass Spectrom.*, 2017, 28, 110-118.
12. H. Yang, L. Shi, X. Zhuang, R. Su, D. Wan, F. Song, J. Li and S. Liu, Identification of structurally closely related monosaccharide and disaccharide isomers by PMP labeling in conjunction with IM-MS/MS, *Sci. Rep.*, 2016, 6, 28079.
13. T. G. Flick, I. D. Campuzano and M. D. Bartberger, Structural resolution of 4-substituted proline diastereomers with ion mobility spectrometry via alkali metal ion cationization, *Anal. Chem.*, 2015, 87, 3300-3307.
14. A. A. Shvartsburg and R. D. Smith, Fundamentals of traveling wave ion mobility spectrometry, *Anal. Chem.*, 2008, 80, 9689-9699.
15. K. J. Fouque, H. Lavanant, S. Zirah, J. D. Hegemann, M. Zimmermann, M. A. Marahiel, S. Rebuffat and C. Afonso, Signatures of Mechanically Interlocked Topology of Lasso Peptides by Ion Mobility-Mass Spectrometry: Lessons from a Collection of Representatives, *J. Am. Soc. Mass Spectrom.*, 2017, 28, 315-322.
16. A. A. Shvartsburg, F. Li, K. Tang and R. D. Smith, High-resolution field asymmetric waveform ion mobility spectrometry using new planar geometry analyzers, *Anal. Chem.*, 2006, 78, 3706-3714.
17. A. V. Tolmachev, I. K. Webb, Y. M. Ibrahim, S. V. Garimella, X. Zhang, G. A. Anderson and R. D. Smith, Characterization of ion dynamics in structures for lossless ion manipulations, *Anal. Chem.*, 2014, 86, 9162-9168.
18. F. A. Fernandez-Lima, D. A. Kaplan, J. Suetering and M. A. Park, Gas-phase separation using a trapped ion mobility spectrometer, *Int. J. Ion Mobil. Spectrom.*, 2011, 14, 93-98.
19. F. A. Fernandez-Lima, D. A. Kaplan and M. A. Park, Note: Integration of trapped ion mobility spectrometry with mass spectrometry, *Rev. Sci. Instr.*, 2011, 82, 126106.
20. D. R. Hernandez, J. D. Debord, M. E. Ridgeway, D. A. Kaplan, M. A. Park and F. Fernandez-Lima, Ion dynamics in a trapped ion mobility spectrometer, *Analyst*, 2014, 139, 1913-1921.
21. P. Benigni, C. J. Thompson, M. E. Ridgeway, M. A. Park and F. Fernandez-Lima, Targeted high-resolution ion mobility separation coupled to ultrahigh-resolution mass spectrometry of endocrine disruptors in complex mixtures, *Anal. Chem.*, 2015, 87, 4321-4325.
22. P. Benigni and F. Fernandez-Lima, Oversampling Selective Accumulation Trapped Ion Mobility Spectrometry Coupled to FT-ICR MS: Fundamentals and Applications, *Anal. Chem.*, 2016, 88, 7404-7412.
23. P. Benigni, K. Sandoval, C. J. Thompson, M. E. Ridgeway, M. A. Park, P. Gardinali and F. Fernandez-Lima, Analysis of Photoirradiated Water Accommodated Fractions of Crude Oils Using Tandem TIMS and FT-ICR MS, *Environ. Sci. Technol.*, 2017, 51, 5978-5988.
24. K. J. Adams, D. Montero, D. Aga and F. Fernandez-Lima, Isomer Separation of Polybrominated Diphenyl Ether Metabolites using nanoESI-TIMS-MS, *Int. J. Ion Mobil. Spectrom.*, 2016, 19, 69-76.
25. A. Castellanos, P. Benigni, D. R. Hernandez, J. D. DeBord, M. E. Ridgeway, M. A. Park and F. A. Fernandez-Lima, Fast Screening of Polycyclic Aromatic Hydrocarbons using Trapped Ion Mobility Spectrometry-Mass Spectrometry, *Anal. Meth.*, 2014, 6, 9328-9332.
26. E. R. Schenk, V. Mendez, J. T. Landrum, M. E. Ridgeway, M. A. Park and F. Fernandez-Lima, Direct observation of differences of Carotenoid polyene chain cis/trans isomers resulting from structural topology, *Anal. Chem.*, 2014, 86, 2019-2024.
27. J. C. Molano-Arevalo, D. R. Hernandez, W. G. Gonzalez, J. Miksovska, M. E. Ridgeway, M. A. Park and F. Fernandez-Lima, Flavin Adenine Dinucleotide structural motifs: from solution to gas-phase, *Anal. Chem.*, 2014, 86, 10223-10230.
28. A. McKenzie-Coe, J. D. DeBord, M. Ridgeway, M. Park, G. Eiceman and F. Fernandez-Lima, Lifetimes and stabilities of familiar explosive molecular adduct complexes during ion mobility measurements, *Analyst*, 2015, 140, 5692-5699.
29. A. Garabedian, D. Butcher, J. L. Lippens, J. Miksovska, P. P. Chapagain, D. Fabris, M. E. Ridgeway, M. A. Park and F. Fernandez-Lima, Structures of the kinetically trapped i-motif DNA intermediates, *Phys. Chem. Chem. Phys.*, 2016, 18, 26691-26702.
30. M. E. Ridgeway, J. A. Silveira, J. E. Meier and M. A. Park, Microheterogeneity within conformational states of ubiquitin revealed by high resolution trapped ion mobility spectrometry, *Analyst*, 2015, 140, 6964-6972.
31. F. Meier, S. Beck, N. Grassl, M. Lubeck, M. A. Park, O. Raether and M. Mann, Parallel Accumulation-Serial Fragmentation (PASEF): Multiplying Sequencing Speed and Sensitivity by Synchronized Scans in a Trapped Ion Mobility Device, *J. Proteome Res.*, 2015, 14, 5378-5387.
32. J. A. Silveira, M. E. Ridgeway and M. A. Park, High resolution trapped ion mobility spectrometry of peptides, *Anal. Chem.*, 2014, 86, 5624-5627.
33. Y. Pu, M. E. Ridgeway, R. S. Glaskin, M. A. Park, C. E. Costello and C. Lin, Separation and Identification of Isomeric Glycans by Selected Accumulation-Trapped Ion Mobility Spectrometry-Electron Activated Dissociation Tandem Mass Spectrometry, *Anal. Chem.*, 2016, 88, 3440-3443.
34. F. C. Liu, S. R. Kirk and C. Bleiholder, On the structural denaturation of biological analytes in trapped ion mobility spectrometry-mass spectrometry, *Analyst*, 2016, 141, 3722-3730.
35. A. Garabedian, P. Benigni, C. E. Ramirez, E. S. Baker, T. Liu, R. D. Smith and F. Fernandez-Lima, Towards Discovery and Targeted Peptide Biomarker Detection Using nanoESI-TIMS-TOF MS, *J. Am. Soc. Mass Spectrom.*, 2017, DOI: 10.1007/s13361-017-1787-8.
36. E. R. Schenk, M. E. Ridgeway, M. A. Park, F. Leng and F. Fernandez-Lima, Isomerization Kinetics of AT Hook Decapeptide Solution Structures, *Anal. Chem.*, 2014, 86, 1210-1214.
37. E. R. Schenk, R. Almeida, J. Miksovska, M. E. Ridgeway, M. A. Park and F. Fernandez-Lima, Kinetic Intermediates of Holo- and Apo-Myoglobin Studied Using HDX-TIMS-MS and Molecular Dynamic Simulations, *J. Am. Soc. Mass Spectrom.*, 2015, 26, 555-563.
38. J. C. Molano-Arevalo, K. Jeanne Dit Fouque, K. Pham, J. Miksovska, M. E. Ridgeway, M. A. Park and F. Fernandez-Lima, Characterization of Intramolecular Interactions of Cytochrome c Using Hydrogen-Deuterium Exchange-Trapped Ion Mobility Spectrometry-Mass Spectrometry and Molecular Dynamics, *Anal. Chem.*, 2017, 89, 8757-8765.
39. P. Benigni, R. Marin, J. C. Molano-Arevalo, A. Garabedian, J. J. Wolff, M. E. Ridgeway, M. A. Park and F. Fernandez-Lima, Towards the analysis of high molecular weight proteins and protein complexes using TIMS-MS, *Int. J. Ion Mobil. Spectrom.*, 2016, 19, 95-104.
40. B. H. Clowers and H. H. Hill, Jr., Influence of cation adduction on the separation characteristics of flavonoid diglycoside isomers using dual gate-ion mobility-quadrupole ion trap mass spectrometry, *J. Mass Spectrom.*, 2006, 41, 339-351.

41. J. M. Dilger, S. J. Valentine, M. S. Glover, M. A. Ewing and D. E. Clemmer, A database of alkali metal-containing peptide cross sections: Influence of metals on size parameters for specific amino acids, *Int. J. Mass Spectrom.*, 2012, 330, 35-45.
42. V. Domalain, M. Hubert-Roux, C. M. Lange, J. Baudoux, J. Rouden and C. Afonso, Enantiomeric differentiation of aromatic amino acids using traveling wave ion mobility-mass spectrometry, *J. Mass Spectrom.*, 2014, 49, 423-427.
43. Soyez, D.; Toullec, J. Y.; Montagne, N.; Ollivaux, C. Experimental strategies for the analysis of D-amino acid containing peptides in crustaceans: a review, *J. Chromatogr. B* 2011, 879, 3102-3107.
44. Ibrahim, Y. M.; Shvartsburg, A. A.; Smith, R. D.; Belov, M. E. Ultrasensitive identification of localization variants of modified peptides using ion mobility spectrometry, *Anal. Chem.* 2011, 83, 5617-5623.
45. Jia, C.; Lietz, C. B.; Yu, Q.; Li, L. Site-specific characterization of (D)-amino acid containing peptide epimers by ion mobility spectrometry, *Anal. Chem.* 2014, 86, 2972-2981.
46. Fernandez-Lima, F. A.; Wei, H.; Gao, Y. Q.; Russell, D. H. On the structure elucidation using ion mobility spectrometry and molecular dynamics, *J. Phys. Chem. A* 2009, 113, 8221-8234.
47. Badman, E. R.; Hoaglund-Hyzer, C. S.; Clemmer, D. E. Monitoring Structural Changes of Proteins in an Ion Trap over ~10-200 ms: Unfolding Transitions in Cytochrome c Ions, *Anal. Chem.* 2001, 73, 6000-6007.
48. Shliaha, P. V.; Baird, M. A.; Nielsen, M. M.; Gorshkov, V.; Bowman, A. P.; Kaszycki, J. L.; Jensen, O. N.; Shvartsburg, A. A. Characterization of Complete Histone Tail Proteoforms Using Differential Ion Mobility Spectrometry, *Anal. Chem.* 2017, 89, 5461-5466.
49. Zheng, X.; Deng, L.; Baker, E. S.; Ibrahim, Y. M.; Petyuk, V. A.; Smith, R. Distinguishing d- and l-aspartic and isoaspartic acids in amyloid beta peptides with ultrahigh resolution ion mobility spectrometry, D. *Chem. Commun.* 2017, 53, 7913-7916.
50. Kaszycki, J. L.; Shvartsburg, A. A. A Priori Intrinsic PTM Size Parameters for Predicting the Ion Mobilities of Modified Peptides, *J. Am. Soc. Mass Spectrom.* 2017, 28, 294-302.
51. Baird, M. A.; Shvartsburg, A. A. Localization of Post-Translational Modifications in Peptide Mixtures via High-Resolution Differential Ion Mobility Separations Followed by Electron Transfer Dissociation, *J. Am. Soc. Mass Spectrom.* 2016, 27, 2064.
52. Shvartsburg, A. A.; Isaac, G.; Leveque, N.; Smith, R. D.; Metz, T. O. Separation and classification of lipids using differential ion mobility spectrometry, *J. Am. Soc. Mass Spectrom.* 2011, 22, 1146.
53. Shvartsburg, A. A.; Creese, A. J.; Smith, R. D.; Cooper, H. J. Separation of a set of peptide sequence isomers using differential ion mobility spectrometry, *Anal. Chem.* 2011, 83, 6918.
54. Shvartsburg, A. A.; Zheng, Y.; Smith, R. D.; Kelleher, N. L. Ion mobility separation of variant histone tails extending to the "middle-down" range, *Anal. Chem.* 2012, 84, 4271.
55. Dodds, J. N.; May, J. C.; McLean, J. A. Correlating Resolving Power, Resolution, and Collision Cross Section: Unifying Cross-Platform Assessment of Separation Efficiency in Ion Mobility Spectrometry, *Anal. Chem.* 2017, 89, 12176.

---

What is claimed is:

1. A method of identifying two or more isomers of a molecule in a sample, the method comprising subjecting the sample to a step of ionization comprising a step of metalation comprising the formation of an ionic complex between the molecule and one or more transition metal(s) having one or more oxidation state(s), following the step of ionization by a step of ion mobility spectrometry (IMS), the step of IMS comprising a step of tandem non-linear IMS and a step of linear high resolution IMS, and following the step of IMS by a step of mass spectrometry (MS), the step of IMS followed by the step of MS separating the two or more isomers of the molecule based on unique collision cross sections of the ionic complexes formed between the two or more isomers of the molecule and the one or more transition metal(s).

2. The method of claim 1, wherein the sample includes an extract from an animal or a plant or a microorganism.

3. The method of claim 2, wherein the molecule is a ribosomally synthesized and post-translationally modified peptide having a molecular weight between 400 Da to 1000 kDa.

4. The method of claim 3, wherein the two or more isomers of the ribosomally synthesized and post-translationally modified peptide are epimers, topoisomers, or proteoforms.

5. The method of claim 1, wherein the linear high resolution IMS is a linear ultra-high resolution trapped IMS having high resolution power of more than 250.

6. The method of claim 1, wherein the non-linear IMS is a field asymmetric waveform ion mobility spectrometry (FAIMS).

7. The method of claim 1, wherein the step of ionization includes electrospray ionization (ESI), desorption electrospray ionization (DESI), matrix-assisted laser desorption ionization (MALDI), laser ablation electrospray ionization (LAESI), electrostatic spray ionization (ESTASI), paper spray ionization, laser desorption ionization (LDI), chemical ionization (CI), or electron impact (EI).

8. The method of claim 1, wherein the step of MS includes the use of quadrupole (Q), time-of-flight (TOF), ion trap (IT), Orbitrap and Fourier transform ion cyclotron resonance (FT-ICR).

9. The method of claim 1, wherein the step of MS comprises tandem mass spectrometry (MS/MS).

10. The method of claim 9, wherein the step of MS/MS comprises collision induced dissociation (CID), electron capture/detachment/transfer (ExD), or infrared multiphoton dissociation (IRMPD).

11. The method of claim 1, wherein the metalation further comprises the formation an ionic complex between the molecule and one or more alkali metal(s) and/or one or more alkaline earth metal(s).

12. The method of claim 11, wherein the alkali metal is lithium (Li), sodium (Na), potassium (K), rubidium (Rb), cesium (Cs), or francium (Fr) and/or the alkaline earth metal is beryllium (Be), magnesium (Mg), calcium (Ca), strontium (Sr), barium (Ba), or radium (Ra).

13. The method of claim 1, wherein the one or more transition metal(s) having one or more oxidation state(s) is/are $Fe^{+2}$, $Fe^{3+}$, $Co^{+2}$, $Co^{+4}$, $Ni^{+2}$, $Ni^{+3}$, $Cu^{+1}$, $Cu^{+2}$, $Mn^{+2}$, $Mn^{+3}$, $Mn^{+4}$, $Mn^{+5}$, $Mn^{+6}$ and $Mn^{+7}$, $Cr^{+2}$, $Cr^{+3}$, $Cr^{+6}$, $Pb^{+2}$, $Pb^{+3}$, $Ti^{+2}$, $Ti^{+3}$, $Ti^{+4}$, or $Zn^{+2}$.

14. A method of identifying in a biological sample an unknown isomer of a known biomolecule, the method comprising the steps of:
   i) subjecting the biological sample to a step of ionization comprising subjecting the biological sample to a step of metalation with ions of one or more transition metal(s) having one or more oxidation state(s) and optionally, further with ions of one or more alkali metal(s) and/or one or more alkaline earth metal(s),
   ii) after step i), subjecting the sample to a step of IMS comprising a step of tandem non-linear IMS and a step of linear high resolution IMS,
   iii) after step ii), subjecting the sample to a step of MS, and
   iv) identifying and optionally, isolating, molecules from the biological sample that have similar but not identical behavior to the known biomolecule in the IMS and MS steps, the step of IMS followed by the step of MS separating the known and unknown isomers of the known biomolecule based on unique collision cross sections of the ionic complexes formed between the known and unknown isomers of the known biomolecule and the one or more transition metal(s).

15. The method of claim 14, wherein the known biomolecule is a ribosomally synthesized and post-translationally modified peptide.

16. The method of claim 4, wherein the ribosomally synthesized and post-translationally modified peptide is a lasso peptide.

17. The method of claim 15, wherein the ribosomally synthesized and post-translationally modified peptide is a lasso peptide, and wherein the two or more isomers of the lasso peptide are epimers, topoisomers, or proteoforms.

18. The method of claim 14, wherein the linear high resolution IMS is a linear ultra-high resolution trapped IMS having high resolution power of more than 250, the non-linear IMS is FAIMS, and the step of MS comprises MS/MS.

19. The method of claim 3, wherein the two or more isomers of the ribosomally synthesized and post-transitionally modified peptide are topoisomers.

20. The method of claim 14, wherein the one or more transition metal(s) having one or more oxidation state(s) is/are $Fe^{+2}$, $Fe^{3+}$, $Co^{+2}$, $Co^{+4}$, $Ni^{+2}$, $Ni^{+3}$, $Cu^{-1}$, $Cu^{+2}$, $Mn^{+2}$, $Mn^{+3}$, $Mn^{+4}$, $Mn^{+5}$, $Mn^{+6}$ and $Mn^{+7}$, $Cr^{+2}$, $Cr^{+3}$, $Cr^{+6}$, $Pb^{+2}$, $Pb^{+3}$, $Ti^{+2}$, $Ti^{+3}$, $Ti^{+4}$, or $Zn^{+2}$.

* * * * *

```
SEQUENCE LISTING

<160> NUMBER OF SEQ ID NOS: 27

<210> SEQ ID NO 1
<211> LENGTH: 4
<212> TYPE: PRT
<213> ORGANISM: Achatina fulica

<400> SEQUENCE: 1

Gly Phe Ala Asp
1

<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Tyr Arg Phe Gly
1

<210> SEQ ID NO 3
<211> LENGTH: 7
<212> TYPE: PRT
<213> ORGANISM: Phyllomedusa sp.

<400> SEQUENCE: 3

Tyr Ala Phe Asp Val Val Gly
1               5
```

```
<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Trp Lys Tyr Met Val Met
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: D-isomer
<222> LOCATION: (5)..(5)

<400> SEQUENCE: 5

Trp Lys Tyr Met Val Met
1               5

<210> SEQ ID NO 6
<211> LENGTH: 20
<212> TYPE: PRT
<213> ORGANISM: Streptomyces sviceus

<400> SEQUENCE: 6

Cys Val Trp Gly Gly Asp Cys Thr Asp Phe Leu Gly Cys Gly Thr Ala
1               5                   10                  15

Trp Ile Cys Val
            20

<210> SEQ ID NO 7
<211> LENGTH: 21
<212> TYPE: PRT
<213> ORGANISM: Streptomyces sp. AA6532

<400> SEQUENCE: 7

Cys Leu Gly Val Gly Ser Cys Asn Asp Phe Ala Gly Cys Gly Tyr Ala
1               5                   10                  15

Ile Val Cys Phe Trp
            20

<210> SEQ ID NO 8
<211> LENGTH: 14
<212> TYPE: PRT
<213> ORGANISM: Xanthomonas gardneri

<400> SEQUENCE: 8

Gly Gly Pro Leu Ala Gly Glu Glu Met Gly Gly Ile Thr Thr
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Synthetic

<400> SEQUENCE: 9

Gly Ile Ser Gly Gly Thr Val Asp Ala Pro Ala Gly Gln Gly Leu Ala
```

```
1               5                   10                  15

Gly

<210> SEQ ID NO 10
<211> LENGTH: 16
<212> TYPE: PRT
<213> ORGANISM: Xanthomonas gardneri

<400> SEQUENCE: 10

Gly Gly Pro Leu Ala Gly Glu Glu Ile Gly Gly Phe Asn Val Pro Gly
1               5                   10                  15

<210> SEQ ID NO 11
<211> LENGTH: 17
<212> TYPE: PRT
<213> ORGANISM: Sphingobium japonicum

<400> SEQUENCE: 11

Gly Pro Gly Gly Ile Thr Gly Asp Val Gly Leu Gly Glu Asn Asn Phe
1               5                   10                  15

Gly

<210> SEQ ID NO 12
<211> LENGTH: 17
<212> TYPE: PRT
<213> ORGANISM: Caulobacter sp. K31

<400> SEQUENCE: 12

Gly Asp Val Leu Asn Ala Pro Glu Pro Gly Ile Gly Arg Glu Pro Thr
1               5                   10                  15

Gly

<210> SEQ ID NO 13
<211> LENGTH: 17
<212> TYPE: PRT
<213> ORGANISM: Caulobacter sp. K31

<400> SEQUENCE: 13

Gly Asp Val Leu Phe Ala Pro Glu Pro Gly Val Gly Arg Pro Pro Met
1               5                   10                  15

Gly

<210> SEQ ID NO 14
<211> LENGTH: 17
<212> TYPE: PRT
<213> ORGANISM: Caulobacter sp. K31

<400> SEQUENCE: 14

Gly Gln Ile Tyr Asp His Pro Glu Val Gly Ile Gly Ala Tyr Gly Cys
1               5                   10                  15

Glu

<210> SEQ ID NO 15
<211> LENGTH: 17
<212> TYPE: PRT
<213> ORGANISM: Streptomyces coerulescens

<400> SEQUENCE: 15

Gly Phe Ile Gly Trp Gly Asn Asp Ile Phe Gly His Tyr Ser Gly Asp
1               5                   10                  15

Phe
```

```
<210> SEQ ID NO 16
<211> LENGTH: 19
<212> TYPE: PRT
<213> ORGANISM: Burkholderia thailandensis E264

<400> SEQUENCE: 16

Gly Thr Pro Gly Phe Gln Thr Pro Asp Ala Arg Val Ile Ser Arg Phe
1               5                   10                  15

Gly Phe Asn

<210> SEQ ID NO 17
<211> LENGTH: 21
<212> TYPE: PRT
<213> ORGANISM: Escherichia coli

<400> SEQUENCE: 17

Gly Gly Ala Gly His Val Pro Glu Tyr Phe Val Gly Ile Gly Thr Pro
1               5                   10                  15

Ile Ser Phe Tyr Gly
            20

<210> SEQ ID NO 18
<211> LENGTH: 19
<212> TYPE: PRT
<213> ORGANISM: Streptomyces sp.

<400> SEQUENCE: 18

Gly Leu Pro Trp Gly Cys Pro Ser Asp Ile Pro Gly Trp Asn Thr Pro
1               5                   10                  15

Trp Ala Cys

<210> SEQ ID NO 19
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: D-isomer
<222> LOCATION: (3)..(3)
<220> FEATURE:
<221> NAME/KEY: D-isomer
<222> LOCATION: (5)..(5)

<400> SEQUENCE: 19

Glu His Trp Ser Tyr Trp Leu Arg Pro Gly
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: D-isomer
<222> LOCATION: (4)..(5)

<400> SEQUENCE: 20

Glu His Trp Ser Tyr Trp Leu Arg Pro Gly
1               5                   10

<210> SEQ ID NO 21
<211> LENGTH: 10
```

```
<212> TYPE: PRT
<213> ORGANISM: Artificial Sequence
<220> FEATURE:
<223> OTHER INFORMATION: Synthetic
<220> FEATURE:
<221> NAME/KEY: D-isomer
<222> LOCATION: (5)..(5)

<400> SEQUENCE: 21

Glu His Trp Ser Tyr Trp Leu Arg Pro Gly
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic

<400> SEQUENCE: 22

Tyr Val Met Gly His Phe Arg Trp Asp Arg Phe Gly
1               5                   10

<210> SEQ ID NO 23
<211> LENGTH: 14
<212> TYPE: PRT
<213> ORGANISM: Homo sapiens

<400> SEQUENCE: 23

Ala Gly Cys Lys Asn Phe Phe Trp Lys Thr Phe Thr Ser Cys
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic

<400> SEQUENCE: 24

Glu Leu Tyr Glu Asn Lys Pro Arg Arg Pro Tyr Ile Leu
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic

<400> SEQUENCE: 25

Glu Leu Tyr Glu Asn Lys Pro Arg Arg Pro Trp Ile Leu
1               5                   10

<210> SEQ ID NO 26
<211> LENGTH: 29
<212> TYPE: PRT
<213> ORGANISM: Artificial Sequence
<220> FEATURE:
<223> OTHER INFORMATION: Synthetic

<400> SEQUENCE: 26

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25
```

```
<210> SEQ ID NO 27
<211> LENGTH: 50
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Phosphorylation
<220> FEATURE:
<221> NAME/KEY: MISC_FEATURE
<222> LOCATION: (4)..(4)
<223> OTHER INFORMATION: Monomethylation or trimethylation
<220> FEATURE:
<221> NAME/KEY: MISC_FEATURE
<222> LOCATION: (6)..(6)
<223> OTHER INFORMATION: Phosphorylation
<220> FEATURE:
<221> NAME/KEY: MISC_FEATURE
<222> LOCATION: (9)..(9)
<223> OTHER INFORMATION: Monomethylation, trimethylation, or acetylation
<220> FEATURE:
<221> NAME/KEY: MISC_FEATURE
<222> LOCATION: (10)..(10)
<223> OTHER INFORMATION: Phosphorylation
<220> FEATURE:
<221> NAME/KEY: MISC_FEATURE
<222> LOCATION: (14)..(14)
<223> OTHER INFORMATION: Acetylation
<220> FEATURE:
<221> NAME/KEY: MISC_FEATURE
<222> LOCATION: (18)..(18)
<223> OTHER INFORMATION: Acetylation
<220> FEATURE:
<221> NAME/KEY: MISC_FEATURE
<222> LOCATION: (23)..(23)
<223> OTHER INFORMATION: Monomethylation or trimethylation
<220> FEATURE:
<221> NAME/KEY: MISC_FEATURE
<222> LOCATION: (27)..(27)
<223> OTHER INFORMATION: Trimethylation or acetylation
<220> FEATURE:
<221> NAME/KEY: MISC_FEATURE
<222> LOCATION: (28)..(28)
<223> OTHER INFORMATION: Phosphorylation
<220> FEATURE:
<221> NAME/KEY: MISC_FEATURE
<222> LOCATION: (36)..(36)
<223> OTHER INFORMATION: Trimethylation or acetylation
<220> FEATURE:
<221> NAME/KEY: MISC_FEATURE
<222> LOCATION: (41)..(41)
<223> OTHER INFORMATION: Phosphorylation

<400> SEQUENCE: 27

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg Tyr Arg Pro Gly Thr Val Ala Leu
        35                  40                  45

Arg Glu
    50
```